US012746359B2

(12) United States Patent
Eves et al.

(10) Patent No.: US 12,746,359 B2
(45) Date of Patent: Sep. 29, 2026

(54) PATIENT INTERFACE

(71) Applicant: RESMED PTY LTD, Bella Vista (AU)

(72) Inventors: Matthew Eves, Sydney (AU); Ryan Michael Kirkpatrick, Sydney (AU); Rahul Khera, Sydney (AU); Adam Francis Barlow, Sydney (AU); Andrew James Bate, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 384 days.

(21) Appl. No.: 18/205,123

(22) Filed: Jun. 2, 2023

(65) Prior Publication Data

US 2023/0321382 A1 Oct. 12, 2023

Related U.S. Application Data

(63) Continuation of application No. 17/599,420, filed as application No. PCT/AU2020/050313 on Mar. 30, 2020, now Pat. No. 11,707,589.

(30) Foreign Application Priority Data

| | | |
|---|---|---|
| May 3, 2019 | (AU) | 2019901516 |
| Sep. 10, 2019 | (AU) | 2019903360 |
| Oct. 21, 2019 | (AU) | 2019903948 |

(51) Int. Cl.
*A61M 16/06* (2006.01)

(52) U.S. Cl.
CPC ........ *A61M 16/0605* (2014.02); *A61M 16/06* (2013.01); *A61M 16/0683* (2013.01)

(58) Field of Classification Search
CPC .............. A61M 16/06; A61M 16/0605; A61M 16/0616
See application file for complete search history.

(56) References Cited

U.S. PATENT DOCUMENTS

| | | | |
|---|---|---|---|
| 4,782,832 | A | 11/1988 | Trimble et al. |
| 4,944,310 | A | 7/1990 | Sullivan |
| 5,560,354 | A | 10/1996 | Berthon-Jones |
| 5,570,689 | A | 11/1996 | Starr |
| 6,412,488 | B1 | 7/2002 | Barnett |
| 6,467,483 | B1 | 10/2002 | Kopacko |
| 6,532,959 | B1 | 3/2003 | Berthon-Jones |
| 6,581,594 | B1 | 6/2003 | Drew et al. |

(Continued)

FOREIGN PATENT DOCUMENTS

| | | |
|---|---|---|
| CN | 106413788 A | 2/2017 |
| CN | 108434575 | 8/2018 |

(Continued)

OTHER PUBLICATIONS

Extended European Search Report issued in related EP Application No. 20862176.3, nine pages, dated Oct. 12, 2023.

(Continued)

*Primary Examiner* — Margaret M Luarca
(74) *Attorney, Agent, or Firm* — Nixon & Vanderhye P.C.

(57) ABSTRACT

A patient interface may include a plenum chamber and a positioning and stabilising structure. The plenum chamber may include a seal-forming structure and a fascia portion. At least a medial portion of the fascia portion is flexible. In embodiments, the patient interface may include a rigidiser to control flexing of the fascia portion.

21 Claims, 57 Drawing Sheets

(56) References Cited

U.S. PATENT DOCUMENTS

| | | | | |
|---|---|---|---|---|
| 7,866,944 | B2 | 1/2011 | Kenyon et al. | |
| 8,636,479 | B2 | 1/2014 | Kenyon et al. | |
| 8,638,014 | B2 | 1/2014 | Sears et al. | |
| 8,733,349 | B2 | 5/2014 | Bath et al. | |
| 9,095,673 | B2 | 8/2015 | Barlow et al. | |
| 9,737,678 | B2 | 8/2017 | Formica et al. | |
| 10,188,820 | B2 | 1/2019 | Edwards et al. | |
| 10,603,461 | B2 | 3/2020 | Skipper et al. | |
| 11,065,413 | B2 | 7/2021 | Barlow et al. | |
| 11,077,274 | B2 | 8/2021 | Ng et al. | |
| 2003/0196656 | A1* | 10/2003 | Moore | A61M 16/0622 128/201.22 |
| 2007/0125385 | A1 | 6/2007 | Ho et al. | |
| 2009/0044808 | A1 | 2/2009 | Guney et al. | |
| 2009/0050156 | A1 | 2/2009 | Ng et al. | |
| 2010/0000534 | A1 | 1/2010 | Kooij et al. | |
| 2013/0213400 | A1 | 8/2013 | Barlow | |
| 2015/0128954 | A1 | 5/2015 | Smith | |
| 2016/0022944 | A1 | 1/2016 | Chodkowski | |
| 2016/0082214 | A1* | 3/2016 | Barlow | A61M 16/0622 128/206.24 |
| 2016/0158474 | A1 | 6/2016 | Harrison | |
| 2016/0184544 | A1* | 6/2016 | Patel | A61M 16/06 128/206.24 |
| 2017/0007795 | A1 | 1/2017 | Pedro et al. | |
| 2017/0024611 | A1 | 1/2017 | Bourdev et al. | |
| 2017/0246411 | A1 | 8/2017 | Mashal et al. | |
| 2018/0177965 | A1 | 6/2018 | Patel | |
| 2018/0339123 | A1 | 11/2018 | Smith et al. | |
| 2019/0374738 | A1 | 12/2019 | Scheiner et al. | |
| 2020/0360640 | A1 | 11/2020 | Formica et al. | |
| 2021/0008317 | A1 | 1/2021 | Davidson | |
| 2021/0038848 | A1 | 2/2021 | Eves et al. | |
| 2021/0275768 | A1 | 9/2021 | Barlow et al. | |
| 2022/0143343 | A1 | 5/2022 | Eves et al. | |

FOREIGN PATENT DOCUMENTS

| | | | |
|---|---|---|---|
| CN | 215916038 | U | 3/2022 |
| JP | 2013-538631 | A | 10/2013 |
| JP | 2016-509934 | A | 4/2016 |
| JP | 2016-518207 | A | 6/2016 |
| JP | 2016-531665 | A | 10/2016 |
| JP | 2017-518113 | A | 7/2017 |
| JP | 2017-531489 | A | 10/2017 |
| JP | 2018-527154 | A | 9/2018 |
| WO | 98/004310 | A1 | 2/1998 |
| WO | 98/034665 | A1 | 8/1998 |
| WO | 2000/078381 | A1 | 12/2000 |
| WO | 2004/073778 | A1 | 9/2004 |
| WO | 2005/063328 | A1 | 7/2005 |
| WO | 2006/074513 | A1 | 7/2006 |
| WO | 2006/130903 | A1 | 12/2006 |
| WO | 2007/133332 | | 11/2007 |
| WO | 2009/052560 | A1 | 4/2009 |
| WO | 2010/135785 | A1 | 12/2010 |
| WO | 2012/171072 | A1 | 12/2012 |
| WO | 2013/020167 | A1 | 2/2013 |
| WO | 2013/066195 | | 5/2013 |
| WO | 2014/183167 | | 11/2014 |
| WO | 2015/020535 | A1 | 2/2015 |
| WO | 2017/049359 | | 3/2017 |
| WO | 2017/124152 | | 7/2017 |
| WO | 2017/185140 | A1 | 11/2017 |
| WO | 2018/065926 | A1 | 4/2018 |
| WO | 2019/119058 | A1 | 6/2019 |
| WO | 2021/046599 | | 3/2021 |

OTHER PUBLICATIONS

"Respiratory Physiology", by John B. West, Lippincott Williams & Wilkins, 9th edition published 2012 (8 pages).

Australian Provisional Application No. 2021902143, filed Jul. 14, 2021, with Specification, Drawings, and Official Filing Receipt thereof (309 pages).

International Search Report dated Jun. 29, 2020 issued in PCT/AU2020/050313 (17 pages).

Written Opinion dated Jun. 29, 2020 issued in PCT/AU2020/050313 (12 pages).

Written Opinion dated May 4, 2021 issued in PCT/AU2020/050313 (12 pages).

International Preliminary Report on Patentability dated Jul. 12, 2021 issued in PCT/AU2020/050313 (99 pages).

Office Action dated Feb. 6, 2023 issued in related U.S. Appl. No. 17/641,751 (26 pages).

Supplementary European Search Report mailed Dec. 5, 2022 in corresponding EP Application 20778814.2 (8 pages).

Notice of Reasons for Refusal with English Translation issue in related JP Application No. 2022-515738, nine pages, dated Oct. 15, 2024.

Notice of Reasons for Refusal in related Japanese Application No. 2022-515738, nine pages, dated Apr. 15, 2024.

Decision of Rejection in corresponding Japanese Application No. 2021-557414, 11 pages, dated Mar. 18, 2024.

Notice of Reasons for Rejection in corresponding Japanese Application No. 2021-557414, five pages, dated Nov. 27, 2023.

First Office Action with English Translation issued in related CN Application No. 202080061928.4, 25 pages, dated May 30, 2025.

Extended European Search Report issued in related EP Application 25176737.2, dated Oct. 29, 2025 (9 pages).

Extended European Search Report issued in corresponding EP Application 20778814.2, dated May 12, 2022 (8 pages).

Notice of Reasons for Rejection issued in corresponding JP Application No. 2021-557414 dated Nov. 27, 2023 (10 pages).

Notice of Reasons for Rejection with English Translation in corresponding JP Application No. 2024-114896, nine pages, dated Apr. 15, 2025.

* cited by examiner

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Relatively Large
Positive Curvature

Relatively Small
Positive Curvature

Zero Curvature

Relatively Small
Negative Curvature

Relatively Large
Negative Curvature

Copyright 2015 ResMed Limited

Copyright 2015 ResMed Limited

Copyright 2015 ResMed Limited

Copyright 2015 ResMed Limited

PATIENT INTERFACE

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

1 CROSS-REFERENCE TO RELATED APPLICATIONS

This application is a continuation of U.S. application Ser. No. 17/599,420, filed Sep. 28, 2021, which is the U.S. national phase of International Application No. PCT/AU2020/050313, filed 30 Mar. 2020 which designated the U.S. and claims priority to Patent Cooperation Treaty Application No. PCT/AU2019/050278 dated 28 Mar. 2019, Australian Patent Application No. 2019901516 dated 3 May 2019, Australian Patent Application No. 2019903360 dated 10 Sep. 2019, and Australian Patent Application No. 2019903948 dated 21 Oct. 2019, the entire contents of each of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 DESCRIPTION OF THE RELATED ART

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH2O).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers.

While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 $cmH_2O$ pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 $cmH_2O$)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

An aspect of the present technology is directed to a patient interface comprising: a plenum chamber comprising: a seal-forming structure; and a fascia portion; and a positioning and stabilising structure, wherein at least a medial portion of the fascia portion is flexible.

An aspect of the present technology us directed to patient interface for use in delivering breathable gas to a patient in positive pressure therapy, comprising: a plenum chamber having a seal-forming structure having a nasal portion which in use engages at least a lower portion of a wearer's nose, and an oral portion which in use engages a lower portion of the wearer's mouth below a lower lip region, and a fascia portion; and a positioning and stabilising structure; wherein the fascia portion comprises a flexible medial portion that is flexible and orientated to facilitate the plenum chamber flexing about a substantially vertical axis when the patient interface is held in an upright position.

A patient interface for use in delivering breathable gas to a patient in positive pressure therapy, comprising: a plenum chamber comprising at least two areas having different stiffnesses to each other, the plenum chamber having a first inlet port located on a first lateral side of the plenum chamber and a second inlet port located on a second lateral side of the plenum chamber; a seal-forming structure, and a fascia portion at least a portion of which is flexible; and a positioning and stabilising structure, wherein the positioning and stabilising structure comprises a first conduit that is configured to connect to the first inlet port and a second conduit that is configured to connect to the second inlet port. A patient interface for use in delivering breathable gas to a patient in positive pressure therapy, comprising: a plenum chamber comprising: a seal-forming structure; and a flexible fascia portion, wherein a hollow protrusion extends away from a medial region of the fascia portion in an inferior-anterior direction, wherein the hollow protrusion has an inlet port which is sized and structured to facilitate provision of a flow of the breathable gas into the plenum chamber; and a positioning and stabilising structure.

A patient interface for use in delivering breathable gas to a patient in positive pressure therapy, comprising: a plenum chamber comprising: a seal-forming structure having a nasal portion structured to seal against at least inferior surfaces of the patient's nose; and a flexible fascia portion; and a positioning and stabilising structure.

An aspect of the present technology is directed to a patient interface comprising: a plenum chamber pressurisable to a therapeutic pressure of at least 6 cmH2O above ambient air pressure throughout a patient's respiratory cycle in use, the plenum chamber comprising: a seal-forming structure constructed and arranged to form a seal with a region of the patient's face surrounding an entrance to the patient's airways, said seal-forming structure having at least one hole configured to deliver a flow of air at said therapeutic pressure to an entrance to the patient's nares in use, the seal-forming structure constructed and arranged to maintain said therapeutic pressure in the plenum chamber throughout the patient's respiratory cycle in use; and a fascia portion having one or more plenum chamber inlet ports sized and structured to receive the flow of air at the therapeutic pressure for breathing by a patient throughout the patient's respiratory cycle in use; and a positioning and stabilising structure configured to generate a force to hold the seal-forming structure in a therapeutically effective position on the patient's head, wherein the fascia portion includes a flexible medial portion.

An aspect of the present technology is directed to a patient interface comprising: a plenum chamber comprising: a seal-forming structure having an oral portion and a nasal portion; and a fascia portion; and a positioning and stabilising structure, wherein at least a medial portion of the fascia portion is flexible.

An aspect of the present technology is directed to a patient interface comprising: a plenum chamber having a seal-forming structure having an oral portion and a nasal portion; and a fascia portion; and a positioning and stabilising structure; wherein at least a medial portion of the fascia portion is flexible, wherein the patient interface includes a rigidiser which in use controls flexing of the fascia portion.

In an embodiment, the rigidiser is structured and/or arranged to allow flexing of the fascia portion towards a patient's face in use. In a preferred form the rigidiser may limit or substantially prevent flexing of the fascia portion outwardly and away from a patient's face in use beyond a pre-determined amount. The rigidiser may have relatively greater flexibility when flexed in a first direction and relatively less flexibility when flexed in a second direction.

In an embodiment, the rigidiser is structured to twist about an axis e.g. an axis oriented parallel to a plane of the patient's face.

An aspect of the present technology is directed to a patient interface comprising: a plenum chamber pressurisable to a therapeutic pressure of at least 6 cmH2O above ambient air pressure throughout a patient's respiratory cycle in use, the plenum chamber having an oral portion and a nasal portion, the plenum chamber comprising: a seal-forming structure constructed and arranged to form a seal with a region of the patient's face surrounding an entrance to the patient's airways, said nasal portion of the seal-forming structure having at least one nasal hole configured to deliver a flow of air at said therapeutic pressure to an entrance to the patient's nares in use, said oral portion of the seal-forming structure having an oral hole configured to deliver the flow of air at said therapeutic pressure to an entrance to the patient's mouth in use, the seal-forming structure constructed and arranged to maintain said therapeutic pressure in the plenum chamber throughout the patient's respiratory cycle in use; and a fascia portion having one or more plenum chamber inlet ports sized and structured to receive the flow of air at the therapeutic pressure for breathing by a patient throughout the patient's respiratory cycle in use; and a positioning and stabilising structure configured to generate a force to hold the seal-forming structure in a therapeutically effective position on the patient's head, wherein the fascia portion is joined to the oral portion and includes at least a medial portion between the nasal portion and an inferior portion of the oral portion, wherein the medial portion is flexible.

In examples of the preceding aspects: substantially the entire fascia portion may be flexible; only the medial portion of the fascia portion may be flexible material; the fascia portion may include at least one insert of greater stiffness than the medial portion; the flexible medial portion may surround a rim of the at least one insert; the fascia portion may include a first lateral insert and a second lateral insert, and the flexible medial portion may be provided between the first lateral insert and the second lateral insert.

In yet further examples, the plenum chamber includes a rigidiser which in use controls the range of movement for the flexible portion. For instance, the rigidiser may not prevent or affect inward flexing of the fascia portion of the interface.

However, in examples, the rigidiser may limit or substantially prevent flexing of the flexible fascia portion outwardly and away from the patient's face in use beyond a pre-determined amount. The rigidiser may have relatively greater flexibility when flexed in a first direction and relatively less flexibility when flexed in a second direction.

In examples of the preceding aspects: at least the medial portion of the fascia portion is made of a flexible material; the flexible material may be one or more of: a silicone, a thermoplastic elastomer (TPE), a foam, or similar.

Alternatively, the medial portion of the fascia portion may be provided by a rigidiser component which can control flexing of the fascia portion in use. In these embodiments, the rigidiser forms part of the plenum chamber of a patient interface according to the present technology. In these embodiments, the rigidiser allows flexing of the fascia portion towards a patient's face in use. In a preferred form the rigidiser may limit or substantially prevent flexing of the fascia portion outwardly and away from a patient's face in use beyond a pre-determined amount. The rigidiser may have relatively greater flexibility when flexed in a first direction and relatively less flexibility when flexed in a second direction.

In examples of the preceding aspects: the seal-forming structure and the fascia portion may be integrally formed; the seal-forming structure may be overmoulded to the fascia portion; the seal-forming structure may be formed separately from the fascia portion and be configured to be permanently or removably connected to the fascia portion. In these embodiments, a rigidiser may be provided such as by being overmoulded to the fascia portion or the fascia portion being overmoulded to the rigidiser. Alternatively, the rigidiser may be permanently or releasably attached to the fascia portion such as by adhesive or other means.

In examples of the preceding aspects: at least a portion of the fascia portion may have a greater stiffness than the seal-forming structure; the plenum chamber includes at least one reinforcing portion at a base of the nasal portion, the at least one reinforcing portion may have a greater stiffness than the nasal portion; the nasal portion of the seal-forming structure may include two lateral portions, wherein the at least one reinforcing portion is provided inferior to the lateral portions.

In examples of the preceding aspects: medial portions of the seal-forming structure may have a lower stiffness than adjacent lateral portions of the seal-forming structure; posterior facing medial portions of the seal-forming structure may have a lower stiffness than adjacent lateral portions of the seal-forming structure; the posterior facing medial portions may include one or more of a lip inferior portion which contacts the chin region of the patient in use, and a lip superior portion which contacts the lip superior of the patient in use; the medial portions of the seal-forming structure having a lower stiffness than adjacent lateral portions of the seal-forming structure may include one or more of: a medial portion of the nasal portion extending from an anterior facing portion of the nasal portion to the lip superior portion which contacts the lip superior of the patient in use, and a medial portion of the oral portion extending from an anterior facing portion of the oral portion to the lip inferior portion which contacts the chin region of the patient in use.

In examples of the preceding aspects: the plenum chamber may include a hollow protrusion extending from the facia portion and having a plenum chamber inlet port; the hollow protrusion may extend from a medial and inferior position on the fascia portion; the hollow protrusion may extend in an inferior-anterior direction; the hollow protrusion may extend in a substantially inferior and partially anterior direction; the hollow protrusion is integrally formed with the fascia portion; the stiffness of the hollow protrusion may be lower than a superior portion of the fascia portion adjacent the hollow protrusion; the thickness of the superior portion of the fascia portion may taper down to the hollow protrusion; a medial portion of the seal-forming structure in the chin region inferior to the hollow protrusion may have a lower stiffness than the superior portion of the fascia portion.

In examples of the preceding aspects, differences in stiffness may be provided by one or more of: wall thickness; stiffer materials (e.g. the same material with a different durometer hardness, or another material), and a reinforcing structure (e.g. a tie or a rib, an undercushion, portion or a chassis, or the like). In examples, one or more reinforcing structures may be selectively provided to the plenum chamber.

In examples of the preceding aspects: the plenum chamber may include at least a first headgear connection point and a second headgear connection point, each of the first headgear connection point and the second headgear connection point provided laterally from the medial portion of the fascia portion; the plenum chamber may include a first headgear connection support and a second headgear connection support, each of the headgear connection supports including at least one headgear connection point; each of the first headgear connection support and the second headgear connection support may include a superior headgear connection point and an inferior headgear connection point; the fascia portion may include a first lateral headgear support recess and a second lateral headgear support recess; the first lateral headgear support recess and a second lateral headgear support recess may be provided on an anterior side of the fascia portion; the first lateral headgear support recess and a second lateral headgear support recess may be configured to receive the first headgear connection support and the second headgear connection support respectively; each of the first headgear connection support and the second headgear connection support may have a greater stiffness than the fascia portion.

In examples of the preceding aspects: the plenum chamber may include a single plenum chamber inlet port; the plenum chamber may include at least a first plenum chamber inlet port and a second plenum chamber inlet port; the first plenum chamber inlet port may be provided to a first lateral side of the medial portion of the fascia portion, and the second plenum chamber inlet port may be provided to a second lateral side of the medial portion of the fascia portion; each plenum chamber port may be provided in an insert provided to the fascia portion; each plenum chamber port may be provided in the flexible material of the fascia portion.

In examples of the preceding aspects: the patient interface may include at least one conduit connector configured to be connected to the plenum chamber inlet port; the patient interface may include a first conduit connector configured to pneumatically connect a first conduit to the plenum chamber to provide the flow of air at the therapeutic pressure to the plenum chamber for breathing by the patient and a second conduit connector configured to pneumatically connect a second conduit to the plenum chamber to provide the flow of air at the therapeutic pressure to the patient interface chamber for breathing by the patient; each of the first conduit connector and the second conduit connector may be configured to pneumatically connect a corresponding one of the first conduit and the second conduit to a corresponding one of the first plenum inlet port and the second plenum chamber hole.

In examples, the plenum chamber may include a decoupling portion between the oral portion and the nasal portion. In examples the plenum chamber may include a decoupling portion between the nasal portion and the fascia portion. In examples the plenum chamber may include a decoupling portion between the oral portion and the fascia portion. In examples, the plenum chamber may include a decoupling portion between at least a portion of the seal forming structure and the one of more plenum chamber inlet ports. In examples, a decoupling portion may be provided by one or more of: one or more gusset portions, and one or more pleats, one or more concertina portions.

In examples, at least a portion of the seal-forming structure may have a first surface finish, and other portions of the plenum chamber may have a second surface finish different from the first surface finish. In examples: the first surface finish may be provided in portions of the seal-forming structure in contact with the patient's face in use, wherein the first surface finish provides a greater coefficient of friction than the second surface finish; the first surface finish may be a polished finish; the second surface finish may be smoother to the touch than the first surface finish; the second surface finish may be a textured surface finish; the second surface finish may be flocked; the textured surface finish may be produced by textured features in tooling used in forming the plenum chamber; the textured surface finish may be provided by etching (for example, laser etching).

In examples, the seal-forming structure may have a first surface finish in a first portion and a second surface finish in a second portion, wherein the second surface finish is different from the first surface finish. In examples: the first surface finish may provide a greater coefficient of friction than the second surface finish; the first surface finish and the second surface finish may be provided on respective ones of the oral portion and the nasal portion.

In examples of the preceding aspects: the nasal portion of the seal-forming structure may include two lateral portions; each lateral portion having a lateral support portions, wherein each of the lateral support portions having a higher resistance to deformation relative to an adjacent portion of the seal-forming structure; each of the lateral support portions may be thicker than the adjacent portion of the seal-forming structure; each of the lateral support portions may have a curved superior boundary; each of the lateral support portions may be substantially fin-shaped; the nasal portion of the seal-forming structure may include a medial portion configured to seal in use against an inferior periphery of the patent's nose surrounding the patient's nares and against the patient's lip superior; the medial portion may be less stiff than the lateral support portions; the nasal portion of the seal-forming structure may include intermediate portions provided between the medial portion and the lateral support portions; intermediate portions may be configured to contact the ala of the patient's nose in use; the intermediate portions may have greater thickness than the medial portion; the intermediate portions may be less stiff than the lateral support portions, and/or the seal-forming structure may be configured not to engage the patient's face below the chin in use.

In examples of the preceding aspects: the seal-forming structure includes lateral peripheral support portions provided at opposite lateral sides of an oral hole, the lateral peripheral support portions being adjacent to an oral hole peripheral portion, and the lateral peripheral support portions being stiffer than the oral hole peripheral portion; the lateral peripheral support portions may be thicker than the oral hole peripheral portion. In examples, the seal-forming structure may comprise posterior-facing lateral portions surrounding a majority of the oral hole peripheral portion; the posterior-facing lateral portions may be stiffer than the oral hole peripheral portion; the posterior-facing lateral portions may extend medially towards lateral-most edges of the oral hole to form the lateral peripheral support portions.

An aspect of the present technology is directed to a patient interface comprising: a plenum chamber according to any one of the preceding aspects or examples thereof; a positioning and stabilising structure configured to generate a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and a vent structure configured to allow a continuous flow of gases exhaled by the patient from an interior of the plenum chamber to ambient, said vent structure being sized and shaped to maintain the therapeutic pressure in the plenum chamber in use, wherein the patient interface is configured to allow the patient to breath from ambient through their mouth in the absence of a flow of pressurised air through the one or more plenum chamber inlet ports.

In examples, the vent structure may be provided in one or more of: the fascia portion; an insert of the fascia portion; and/or a conduit connector.

Another aspect of one form of the present technology is an oronasal patient interface configured to deliver a flow of air at a therapeutic pressure to the patient's nasal airways and oral airway in use, the oronasal patient interface sealing against at least inferior surfaces of the patient's nose. Such an arrangement may be referred to as an "under-the-nose full face" or "minimal contact full face" patient interface, providing an ultra-compact form.

In examples, the oronasal patient interface may comprise a plenum chamber according to any one of the preceding aspects or examples thereof. In examples, the oronasal patient interface may comprise a seal-forming structure according to any one of the preceding aspects or examples thereof.

In examples, the seal-forming structure may not extend over the nasal bones of the patient's nose; the seal-forming structure may not extend over the nasal ridge of the patient's nose; the seal-forming structure may not extend over a superior surface of the pronasale of the patient's nose; the seal-forming structure may not extend over an anterior surface of the pronasale of the patient's nose.

In examples, the seal-forming structure may comprise a first seal-forming portion constructed and arranged to form a seal with a region of the patient's face surrounding an entrance to the patient's mouth, said seal-forming structure configured such that the flow of air at said therapeutic pressure is delivered to the mouth, the seal-forming structure constructed and arranged to maintain said therapeutic pressure in the plenum chamber throughout the patient's respiratory cycle in use. In examples, the seal-forming structure may comprise a second seal-forming portion constructed and arranged to form a seal with a region of the patient's face surrounding an entrance to the patient's nose, said seal-forming structure configured such that the flow of air at said therapeutic pressure is delivered to the nose, the seal-forming structure constructed and arranged to maintain said therapeutic pressure in the plenum chamber throughout the patient's respiratory cycle in use. In examples, the first seal-forming portion may comprise a first hole configured to provide a supply of air to the patient's mouth, and the second seal-forming portion may comprise at least one additional hole configured to provide a supply of air to at least one of the patient's nares.

One form of the present technology comprises a patient interface comprising:

a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient;

a first seal-forming structure constructed and arranged to form a seal with a region of the patient's face surrounding an entrance to the patient's mouth such that the flow of air at said therapeutic pressure is delivered to the mouth, the first seal-forming structure constructed and arranged to maintain said therapeutic pressure in the plenum chamber throughout the patient's respiratory cycle in use;

a second seal-forming structure constructed and arranged to form a seal with a region of the patient's face surrounding an entrance to the patient's nose such that the flow of air at said therapeutic pressure is delivered to the nose, the second seal-forming structure constructed and arranged to maintain said therapeutic pressure in the plenum chamber throughout the patient's respiratory cycle in use; and a vent structure to allow a continuous flow of gases exhaled by the patient from an interior of the plenum chamber to vent to ambient, said vent structure being sized and shaped to maintain the therapeutic pressure in the plenum chamber in use;

the patent interface further comprising:

a pair of support portions provided on opposite sides of the interface between the second seal forming structure and an anterior wall of the plenum chamber, wherein the support portions are configured to oppose compression in the anterior-posterior direction.

In embodiments:

a) the support portions are connected to portions of the second seal forming structure which seal, in use, against the patient's lip superior;

b) the support portions are connected to portions of the second seal forming structure which, in use, seal to the patient's lip superior, directly inferior to the lower corners of the patient's nose;

c) the support portions are curved when viewed in cross-section parallel to a sagittal plane;

d) the support portions are curved when viewed in cross-section parallel to a frontal plane;

e) the plenum chamber comprises an oral portion and a nasal portion;

f) each support portion is connected to the oral portion of the plenum chamber adjacent a boundary of a lateral side wall portion of the oral portion and a lateral side wall portion of the nasal portion;

g) each support portion is connected to the oral portion of the shell adjacent a boundary of an anterior wall portion of the oral portion and an anterior wall portion of the nasal portion;

h) the lateral side wall portions of the plenum chamber curve inwardly adjacent the boundary with the nasal portion, wherein each support portion is substantially contiguous with an adjacent lateral side wall portion;

i) the second seal-forming structure comprises at least one nasal aperture configured to deliver a flow of air at said therapeutic pressure to an entrance to the patient's nares, wherein, in use no part of either support portion is directly inferior to the or each nasal aperture;

j) the interface further comprises a positioning and stabilising structure configured to generate a force to hold the seal-forming structure in a therapeutically effective position on the patient's head; and/or k) the plenum chamber is at least partially formed by a shell and the vent structure is provided to the shell.

Another form of the technology comprises a patient interface comprising:

a plenum chamber pressurisable to a therapeutic pressure of at least 6 $cmH_2O$ above ambient air pressure, said plenum chamber including a plenum chamber inlet port sized and structured to receive a flow of air at the therapeutic pressure for breathing by a patient;

a first seal-forming structure connected to an oral portion of the plenum chamber, the first seal-forming structure constructed and arranged to form a seal with a region of the patient's face surrounding an entrance to the patient's mouth such that the flow of air at said therapeutic pressure is delivered to the mouth, the first seal-forming structure constructed and arranged to maintain said therapeutic pressure in the plenum chamber throughout the patient's respiratory cycle in use;

a second seal-forming structure connected to a nasal portion of the plenum chamber, the second seal-forming structure constructed and arranged to form a seal with a region of the patient's face surrounding an entrance to the patient's nose such that the flow of air at said therapeutic pressure is delivered to the nose, the second seal-forming structure constructed and arranged to maintain said therapeutic pressure in the plenum chamber throughout the patient's respiratory cycle in use; and a vent structure to allow a continuous flow of gases exhaled by the patient from an interior of the plenum chamber to vent to ambient, said vent structure being sized and shaped to maintain the therapeutic pressure in the plenum chamber in use;

wherein a first anterior wall portion of the nasal portion of the plenum chamber, adjacent a boundary with the oral portion of the plenum chamber, is more flexible than an immediately adjacent region of the oral portion of the plenum chamber, and a second anterior wall portion of the nasal portion of the plenum chamber, which is immediately adjacent the first anterior wall portion and is on an opposite side of the first anterior wall portion to the boundary with the oral portion of the plenum chamber, is less flexible than the immediately adjacent portions of the anterior wall.

In examples:

a) the first anterior wall portion is thinner than the immediately adjacent portions of the plenum chamber wall;

b) the second anterior wall portion is thicker than the immediately adjacent portions of the plenum chamber wall;

c) the first and second anterior wall portions are made from the same material;

d) the first anterior wall portion extends across substantially an entire width of the nasal portion of the plenum chamber;

e) the second anterior wall portion extends across at least a majority of a width of the nasal portion of the plenum chamber;

f) the first anterior wall portion extends in a superior direction around at least one lateral edge of the second anterior wall portion;

g) the second anterior wall portion extends across substantially an entire width of the nasal portion of the plenum chamber;

h) a central portion of the first anterior wall portion extends further in the superior direction than lateral portions of the first anterior wall portion;

I) an upper boundary of the first anterior wall portion is curved;

j) a lower boundary of the first anterior wall portion is curved; and/or k) the plenum chamber is at least partially formed by a shell and the vent structure is provided to the shell.

Another form of the technology comprises a patient interface comprising:

a plenum chamber pressurisable to a therapeutic pressure of at least 6 $cmH_2O$ above ambient air pressure, said plenum chamber including a plenum chamber inlet port sized and structured to receive a flow of air at the therapeutic pressure for breathing by a patient;

a first seal-forming structure connected to an oral portion of the plenum chamber, the first seal-forming structure constructed and arranged to form a seal with a region of the patient's face surrounding an entrance to the patient's mouth such that the flow of air at said therapeutic pressure is delivered to the mouth, the first seal-forming structure constructed and arranged to maintain said therapeutic pressure in the plenum chamber throughout the patient's respiratory cycle in use;

a second seal-forming structure connected to a nasal portion of the plenum chamber, the second seal-forming structure constructed and arranged to form a seal with a region of the patient's face surrounding an entrance to the patient's nose such that the flow of air at said therapeutic pressure is delivered to the nose, the second seal-forming structure constructed and arranged to maintain said therapeutic pressure in the plenum chamber throughout the patient's respiratory cycle in use; and a vent structure to allow a continuous flow of gases exhaled by the patient from an interior of the plenum chamber to vent to ambient, said vent structure being sized and shaped to maintain the therapeutic pressure in the plenum chamber in use;

wherein posterior surfaces of the lateral portions of the second seal forming structure slope in a superior-anterior direction from a boundary of the first and second seal forming structures.

In examples:

a) the slope of each lateral portion forms an angle of between 20 degrees and 90 degrees with a mid-contact plane of the mask;

b) no part of the patent interface contacts the patient's alar crest point, in use;

c) the interface is configured to prevent occlusion of the patient's nares, or to at least reduce occlusion relative to the interfaces of the prior art; and/or d) the plenum chamber is at least partially formed by a shell and the vent structure is provided to the shell.

Another form of the technology comprises a patient interface comprising:

a plenum chamber pressurisable to a therapeutic pressure of at least 6 $cmH_2O$ above ambient air pressure, said plenum chamber including a plenum chamber inlet port sized and structured to receive a flow of air at the therapeutic pressure for breathing by a patient;

a first seal-forming structure connected to an oral portion of the plenum chamber, the first seal-forming structure constructed and arranged to form a seal with a region of the patient's face surrounding an entrance to the patient's mouth such that the flow of air at said therapeutic pressure is delivered to the mouth, the first seal-forming structure constructed and arranged to maintain said therapeutic pressure in the plenum chamber throughout the patient's respiratory cycle in use;

a second seal-forming structure connected to a nasal portion of the plenum chamber, the second seal-forming structure constructed and arranged to form a seal with a region of the patient's face surrounding an entrance to the patient's nose such that the flow of air at said therapeutic pressure is delivered to the nose, the second seal-forming structure constructed and arranged to maintain said therapeutic pressure in the plenum chamber throughout the patient's respiratory cycle in use; and a vent structure to allow a continuous flow of gases exhaled by the patient from an interior of the plenum chamber to vent to ambient, said vent structure being sized and shaped to maintain the therapeutic pressure in the plenum chamber in use;

wherein a boundary between the first seal-forming structure and the second seal-forming structure comprises a ridge.

In examples:

a) the ridge has a radius of curvature of less than 2 mm;

b) the ridge extends across substantially an entire boundary between the first seal forming structure and the second seal forming structure;

c) in use, the ridge engages a patient's face proximate the entrances to the nares where the ala meets the face above the lip superior;

d) the ridge resists creases forming in the first and/or second seal forming structure adjacent the ridge; and/or e) in use the plenum chamber is at least partially formed by a shell and the vent structure is provided to the shell.

Another form of the technology comprises a patient interface comprising:

a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient;

a first seal-forming structure connected to an oral portion of the plenum chamber, the first seal-forming structure constructed and arranged to form a seal with a region of the patient's face surrounding an entrance to the patient's mouth such that the flow of air at said therapeutic pressure is delivered to the mouth, the first seal-forming structure constructed and arranged to maintain said therapeutic pressure in the plenum chamber throughout the patient's respiratory cycle in use;

a second seal-forming structure connected to a nasal portion of the plenum chamber, the second seal-forming structure constructed and arranged to form a seal with a region of the patient's face surrounding an entrance to the patient's nose such that the flow of air at said therapeutic pressure is delivered to the nose, the second seal-forming structure constructed and arranged to maintain said therapeutic pressure in the plenum chamber throughout the patient's respiratory cycle in use; and a vent structure to allow a continuous flow of gases exhaled by the patient from an interior of the plenum chamber to vent to ambient, said vent structure being sized and shaped to maintain the therapeutic pressure in the plenum chamber in use;

wherein, at least a portion of the oral portion of plenum chamber comprises a flexible shell, wherein the flexible shell is formed from a material having a Young's modulus of less than 0.4 GPa.

In examples:

a) the flexible shell is formed from a material having a Young's modulus less than 0.1 GPa, preferably between 0.3-0.7 MPa.

b) at least one component is connected to the flexible shell, wherein the at least one component is stiffer than a portion of the flexible shell adjacent the component;

c) the at least one component comprises one or more of: a vent module; a headgear connector; a headgear connector connected to a rigidizing arm; a rigidizing member; a less flexible shell portion;

d) the at least one component is releasably connectable to the flexible shell;

e) the at least one component is permanently connected to the flexible shell;

f) the at least one component is overmoulded to the flexible shell;

g) the flexible shell comprises stiffening portions having greater thickness than immediately adjacent portions of the flexible shell;

h) the at least one component is configured as stiffening ribs or bands;

i) a central portion of the oral portion of the plenum chamber has a greater stiffness than the remainder of the plenum chamber; and/or j) the plenum chamber is at least partially formed by a shell and the vent structure is provided to the shell.

An aspect of one form of the present technology is a patient interface having the ability to be fitted to a wide range of patient face shapes and sizes.

An aspect of one form of the present technology is a patient interface having the ability to be fitted to a wide range variety of facial shapes and/or features.

An aspect of one form of the present technology is a patient interface having greater comfort levels, e.g. by requiring a lower headgear tension to achieve a seal, meaning less force may be exerted on the face and/or head of the patient.

An aspect of one form of the present technology is a patient interface having improved seal stability by reducing transfer of disruptive forces to the seal-forming structure, e.g. from lateral forces resulting from the patient sleeping on their side with the side of their face against a pillow.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
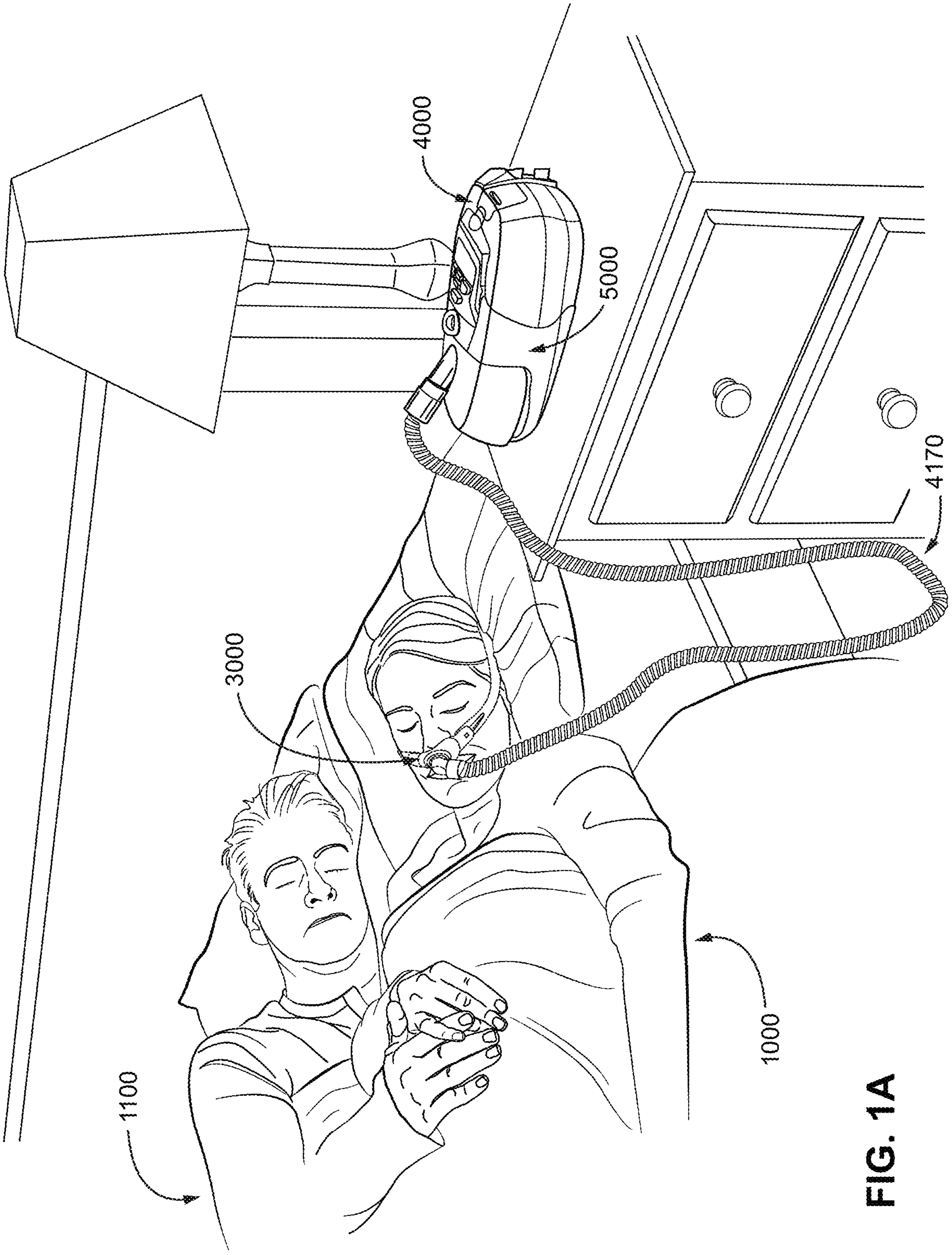
Figure 1B:
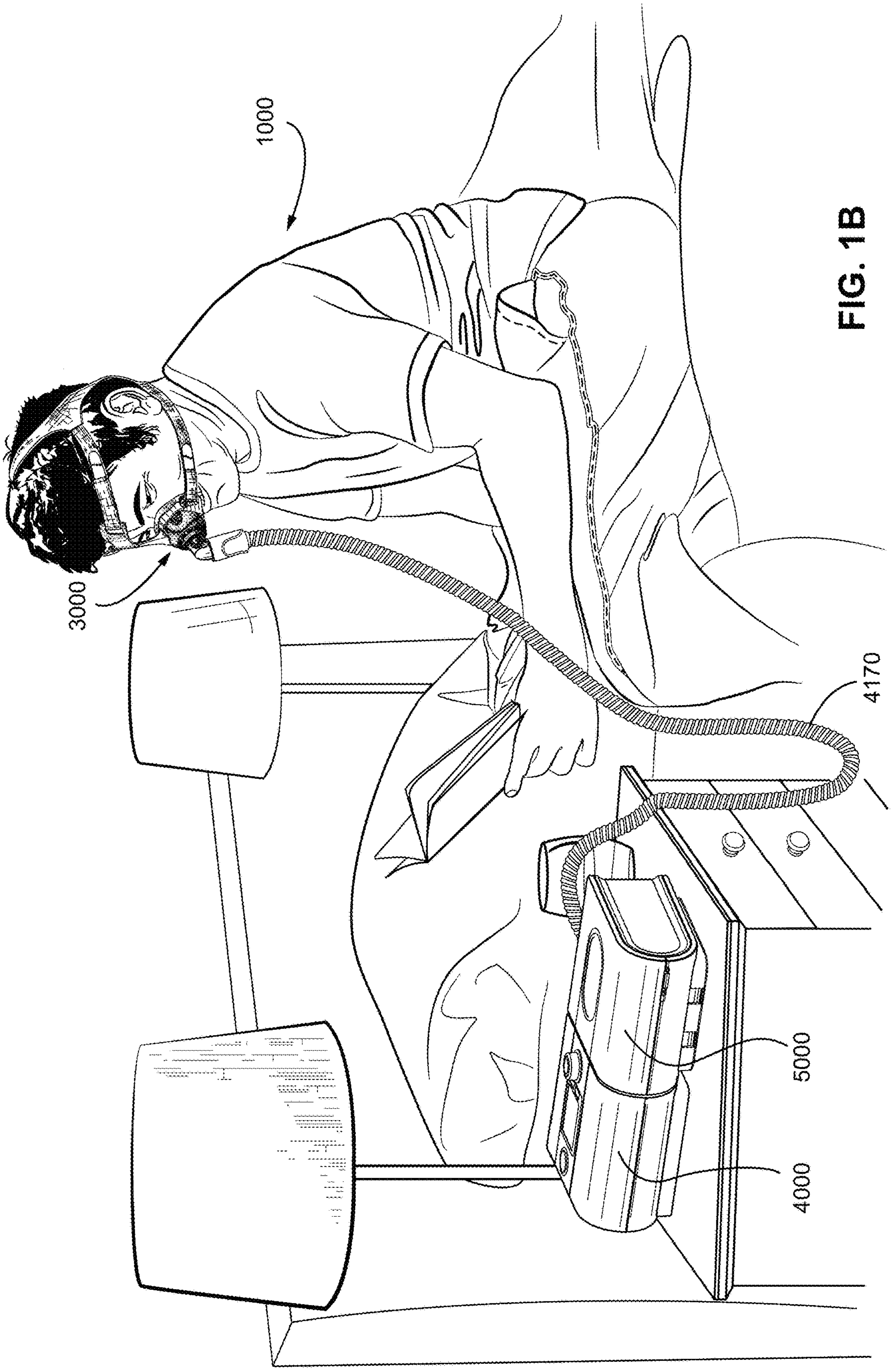
Figure 1C:
Figure 2A:
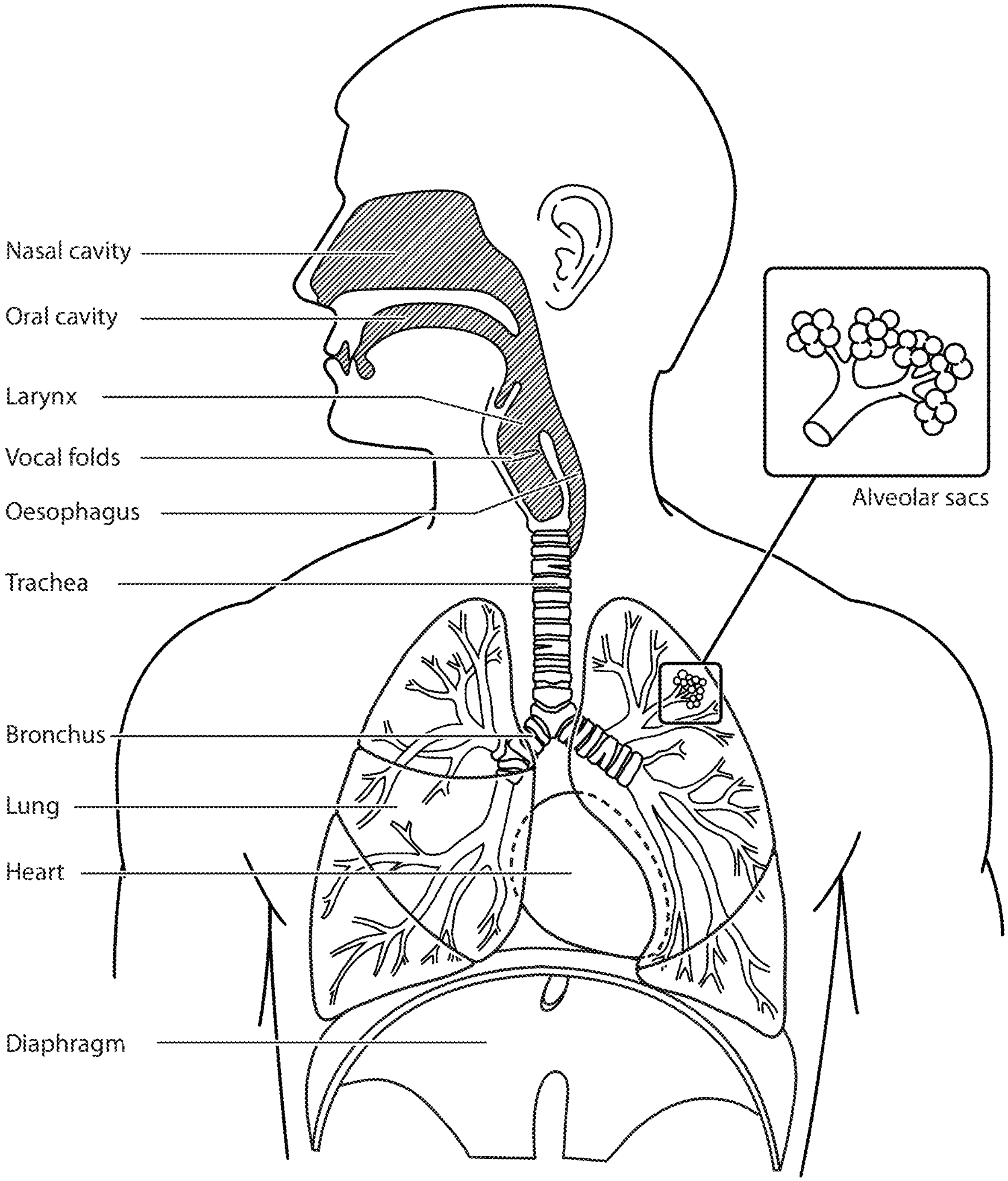
FIG. 2A shows an overview of a human respiratory system including the nasal and oral cavities, the larynx, vocal folds, oesophagus, trachea, bronchus, lung, alveolar sacs, heart and diaphragm.
Figure 2B:
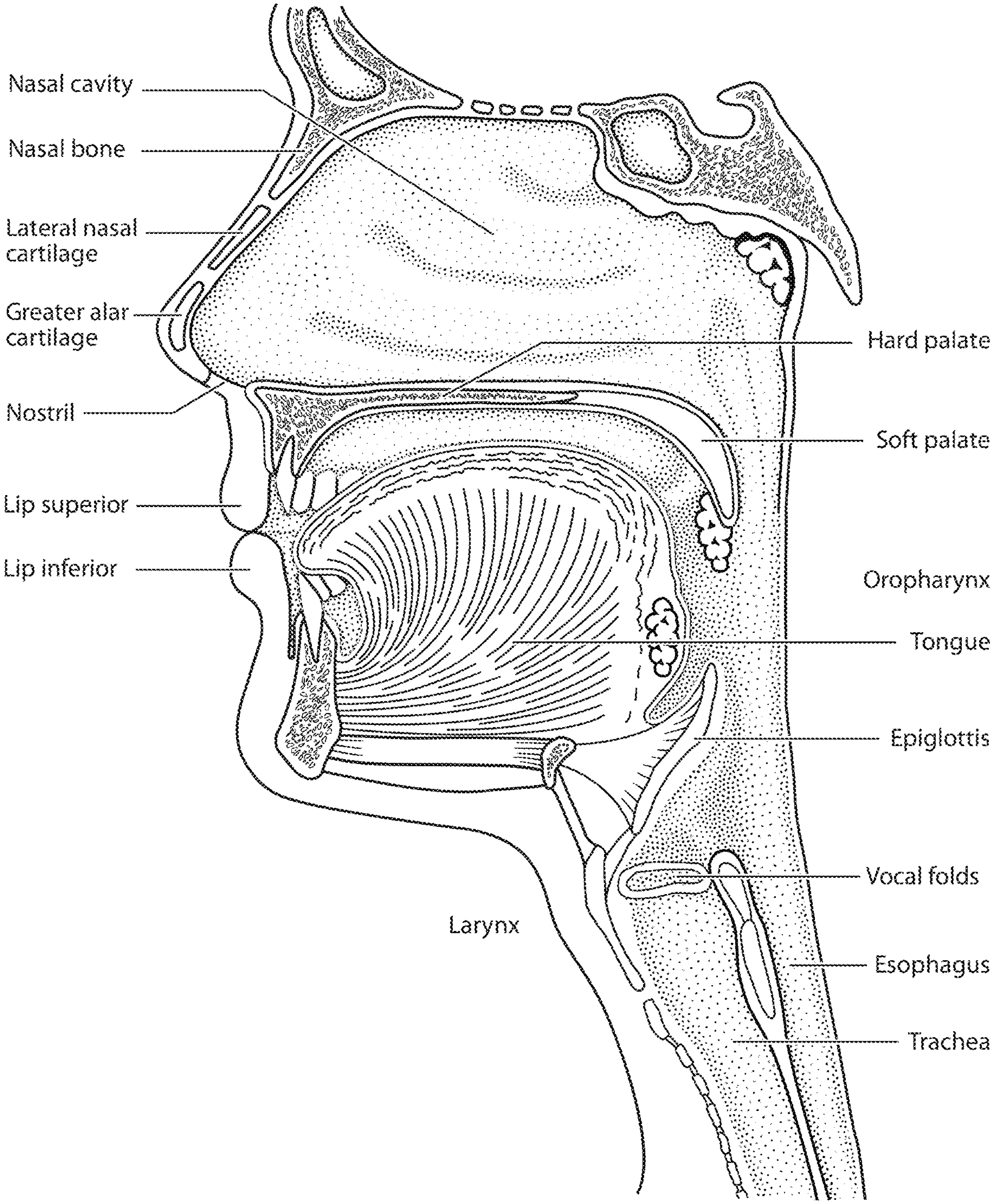
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
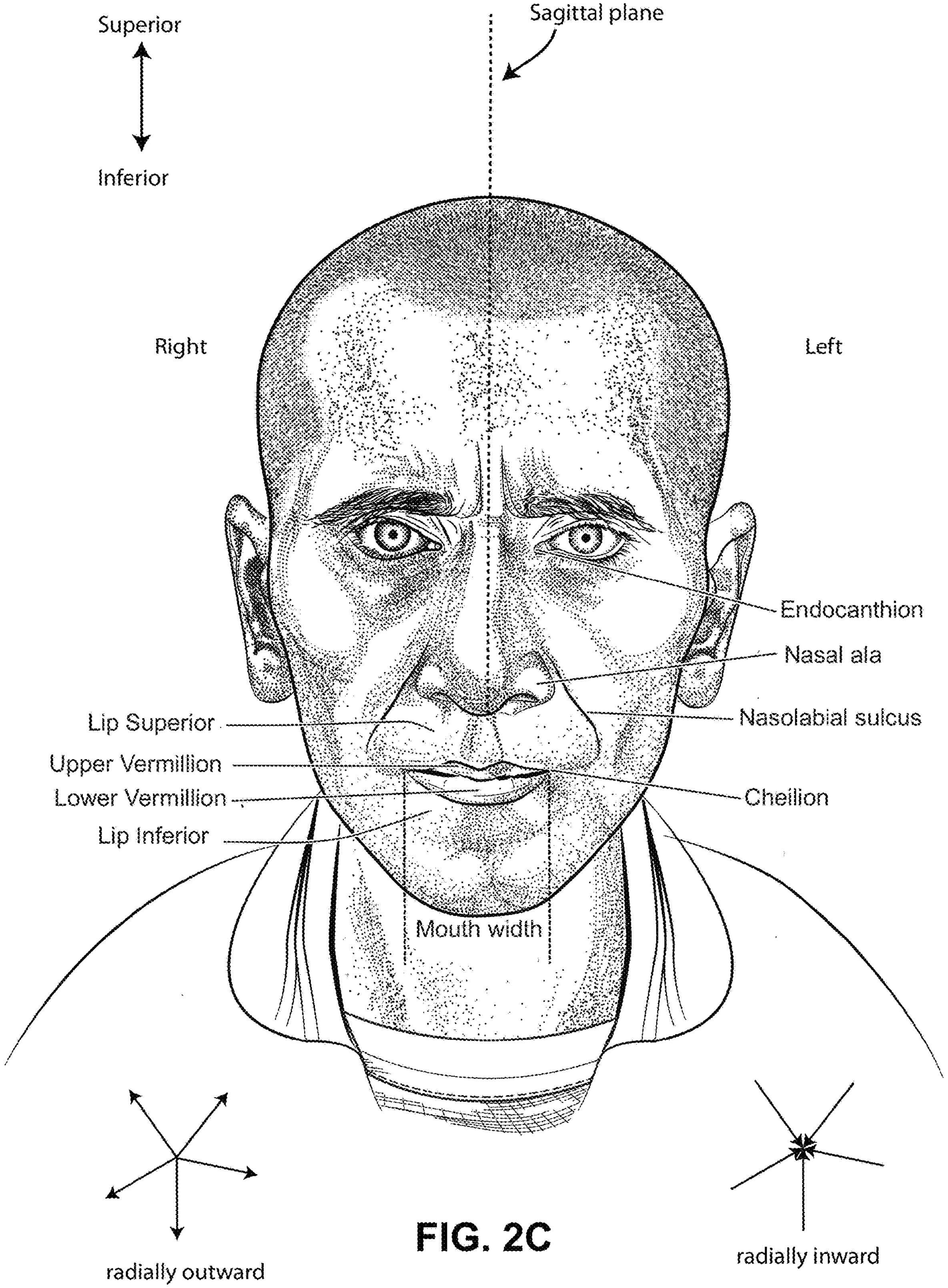
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
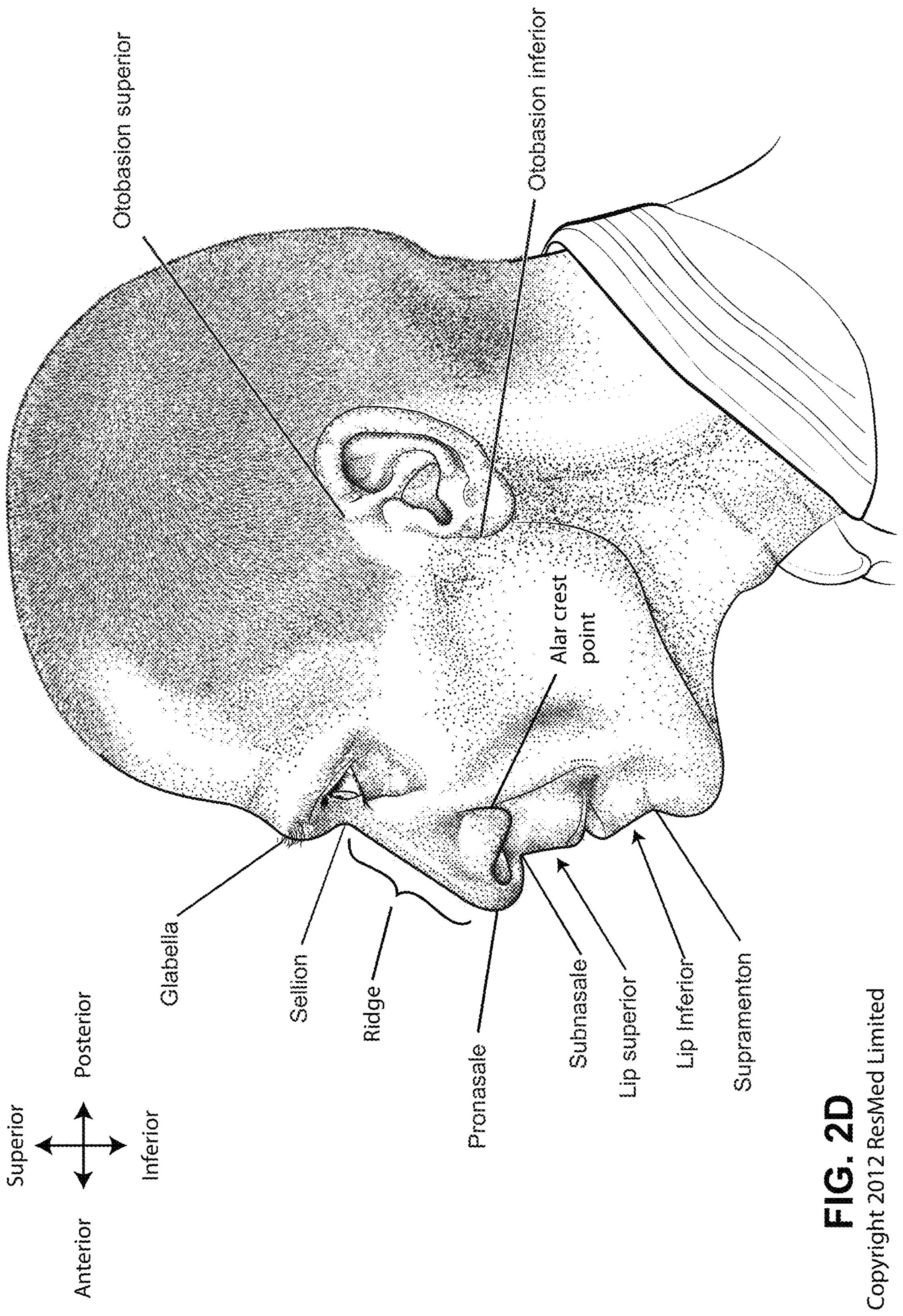
FIG. 2D is a side view of a head with several features of surface anatomy identified including *glabella*, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
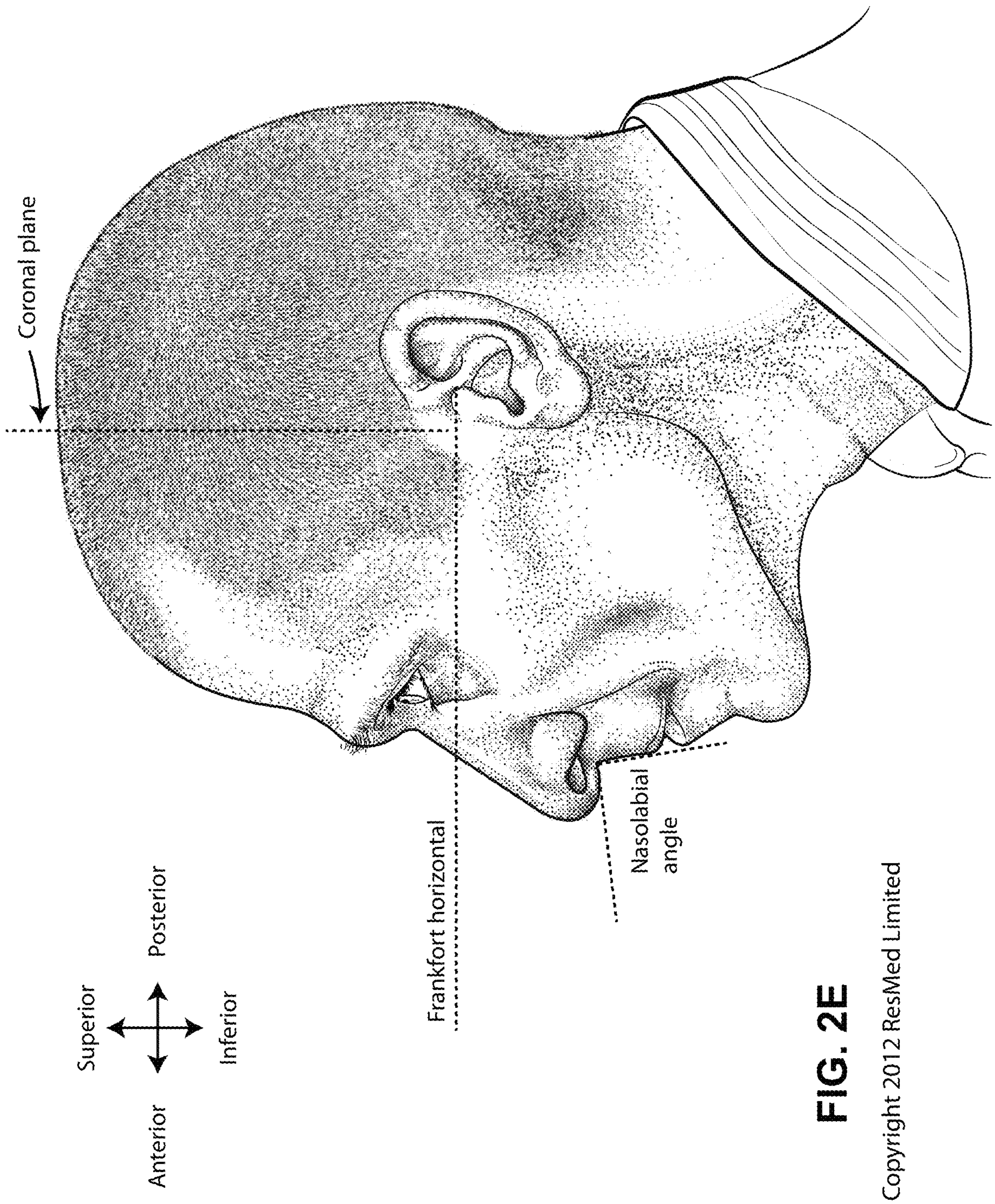

FIG. 2E is a further side view of a head. The approximate locations of the Frankfort horizontal and nasolabial angle are indicated. The coronal plane is also indicated.

Figure 2F:
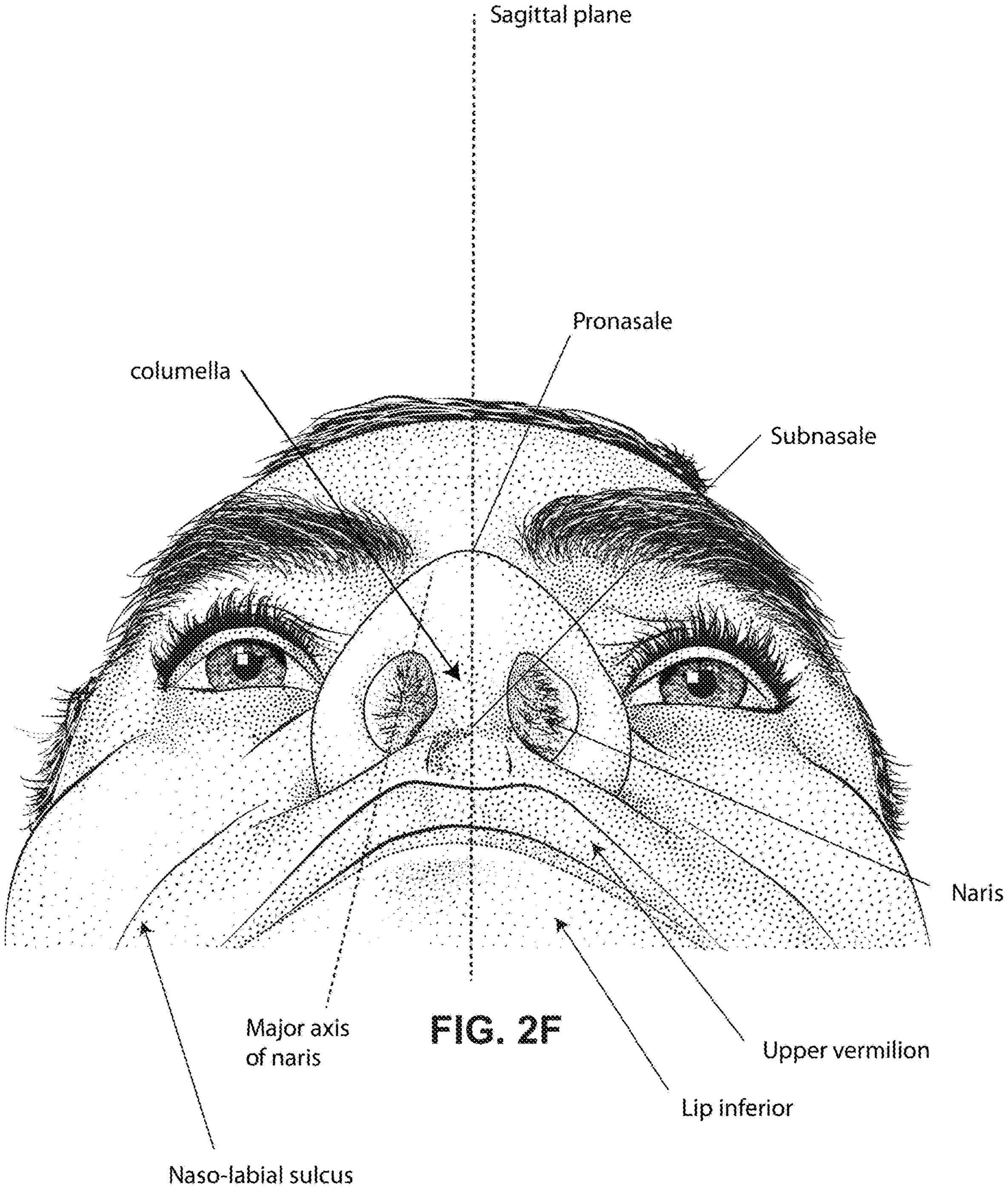

FIG. 2F shows a base view of a nose with several features identified including naso-labial sulcus, lip inferior, upper Vermilion, naris, subnasale, columella, pronasale, the major axis of a naris and the midsagittal plane.

Figure 2G:
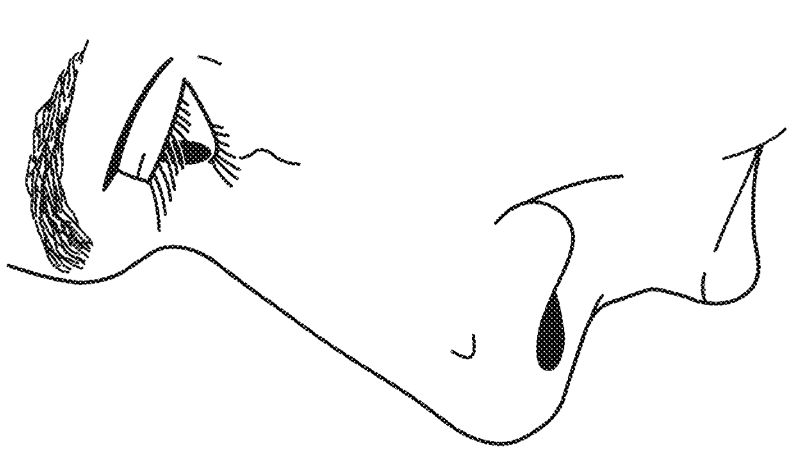

FIG. 2G shows a side view of the superficial features of a nose.

Figure 2H:
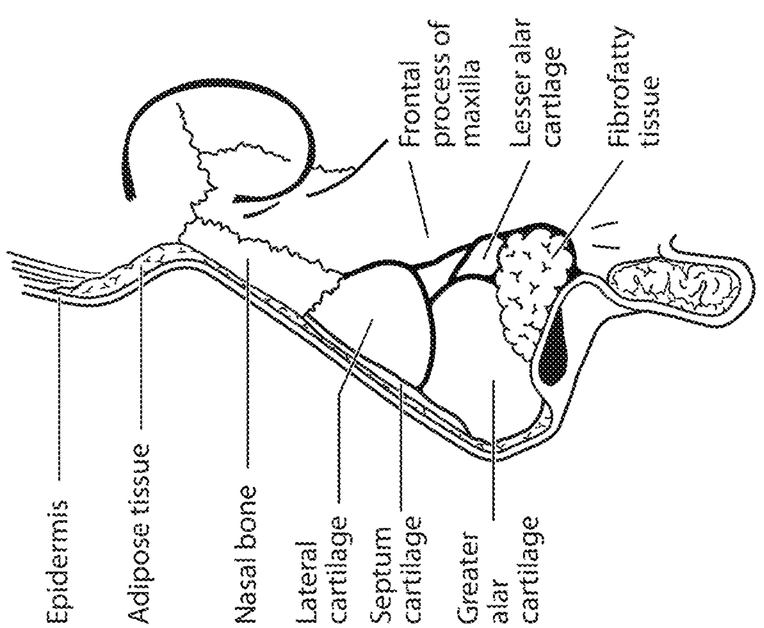

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

Figure 2I:
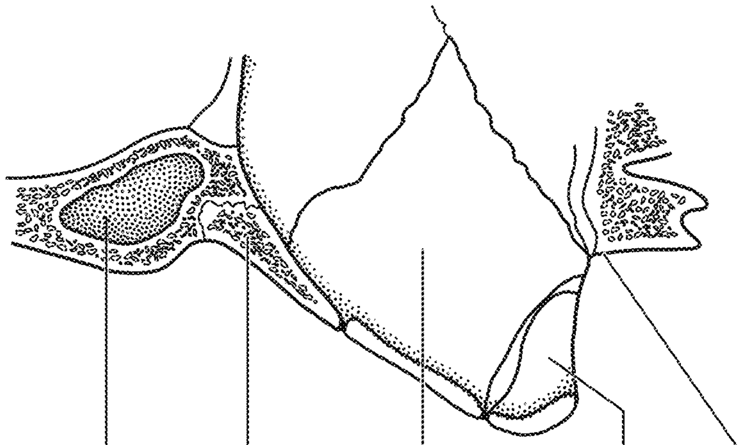

FIG. 2I shows a medial dissection of a nose, approximately several millimeters from the midsagittal plane, amongst other things showing the septum cartilage and medial crus of greater alar cartilage.

Figures 2J, 2K:
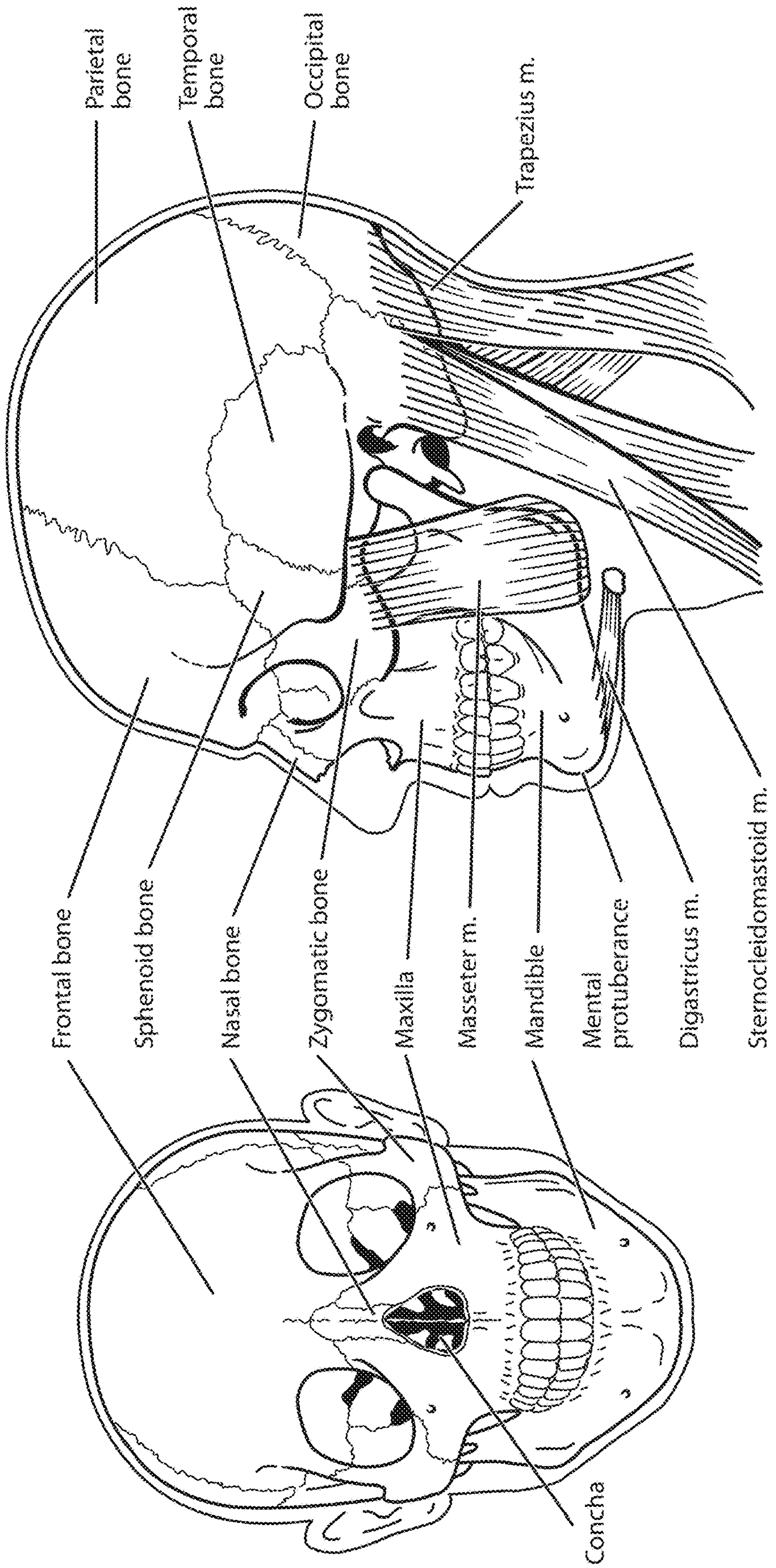

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
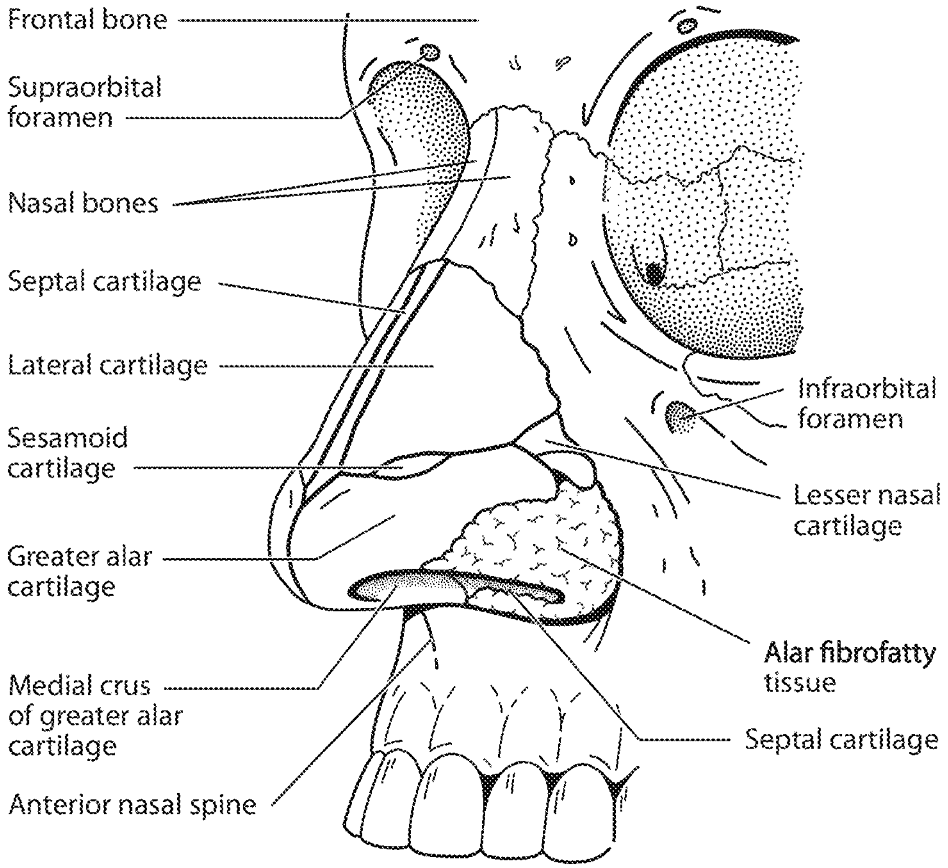

FIG. 2L shows an anterolateral view of a nose.

4.3 Patient Interface

Figure 3A:
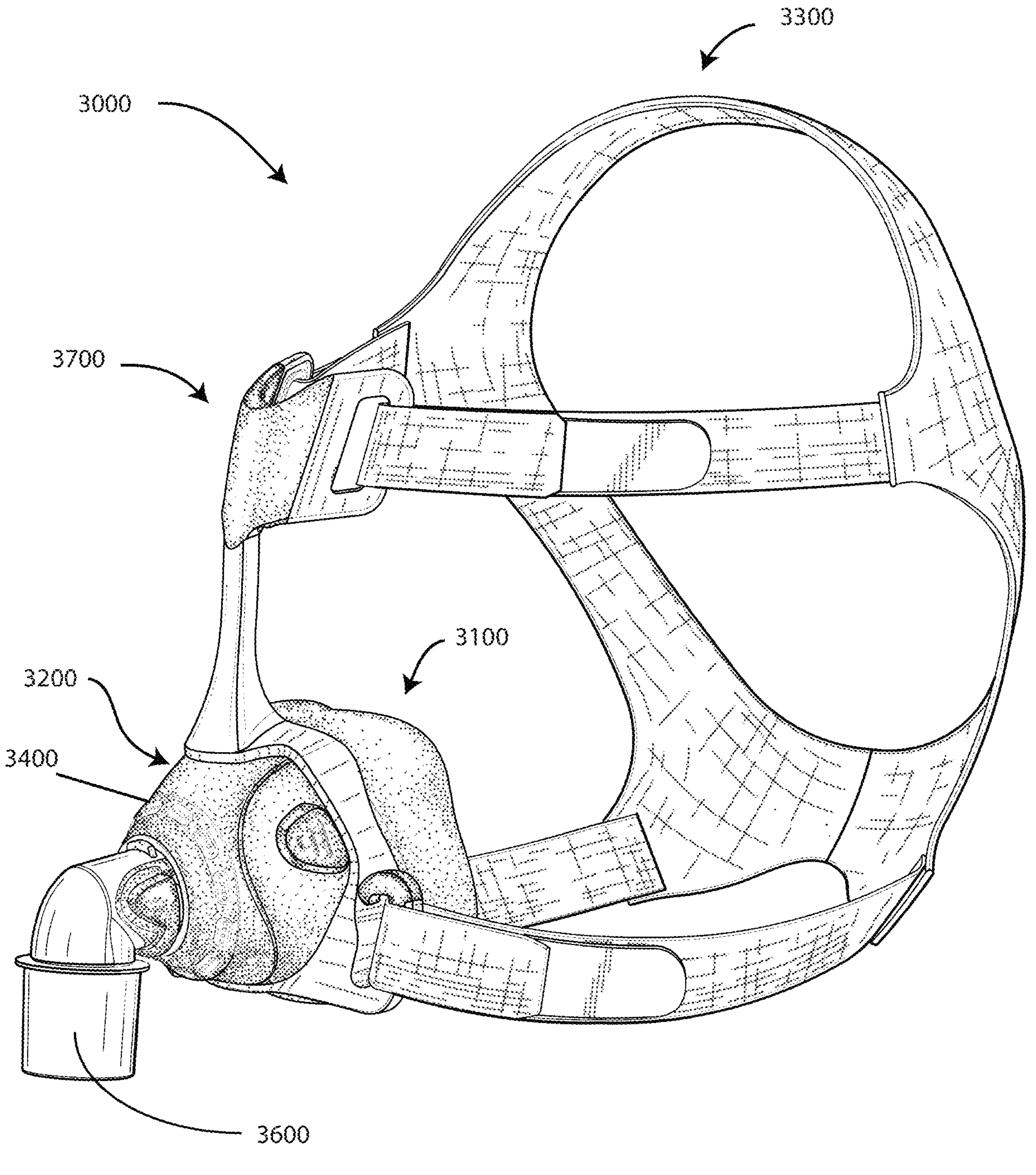

FIG. 3A shows a patient interface in the form of a nasal mask in accordance with one form of the present technology.

Figure 3B:
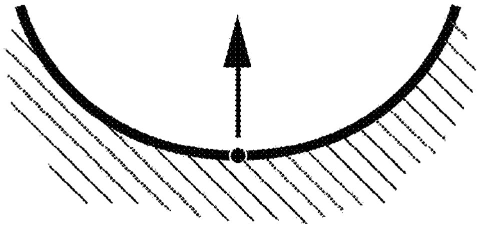

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
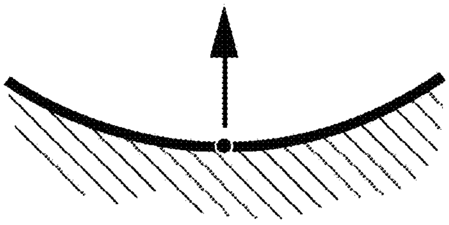

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
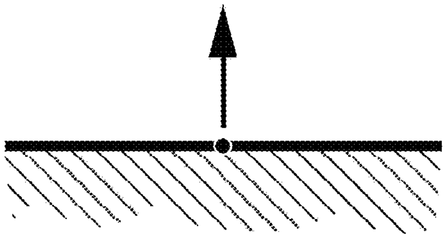

FIG. 3D shows a schematic of a cross-section through a structure at a point. An outward normal at the point is indicated. The curvature at the point has a value of zero.

Figure 3E:
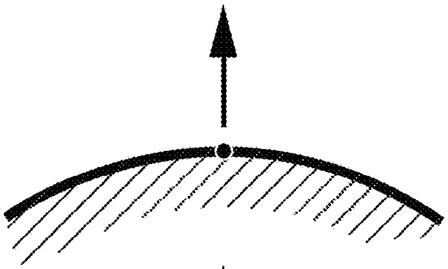

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
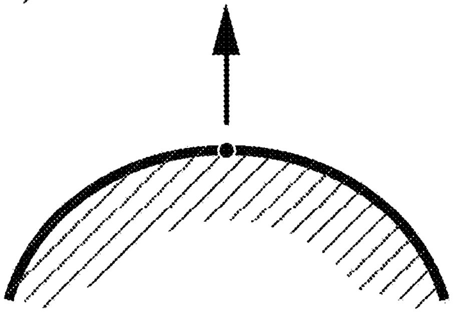

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
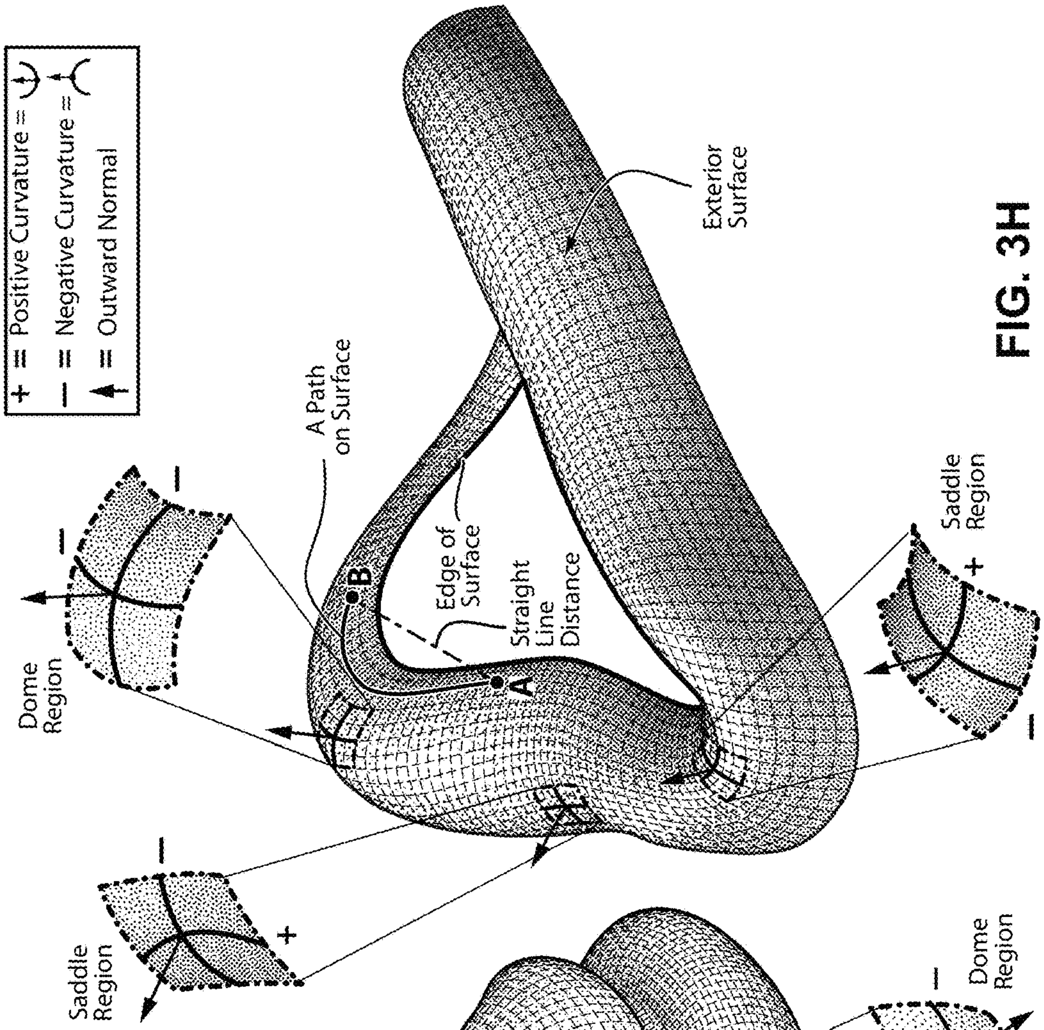
Figure 3G:
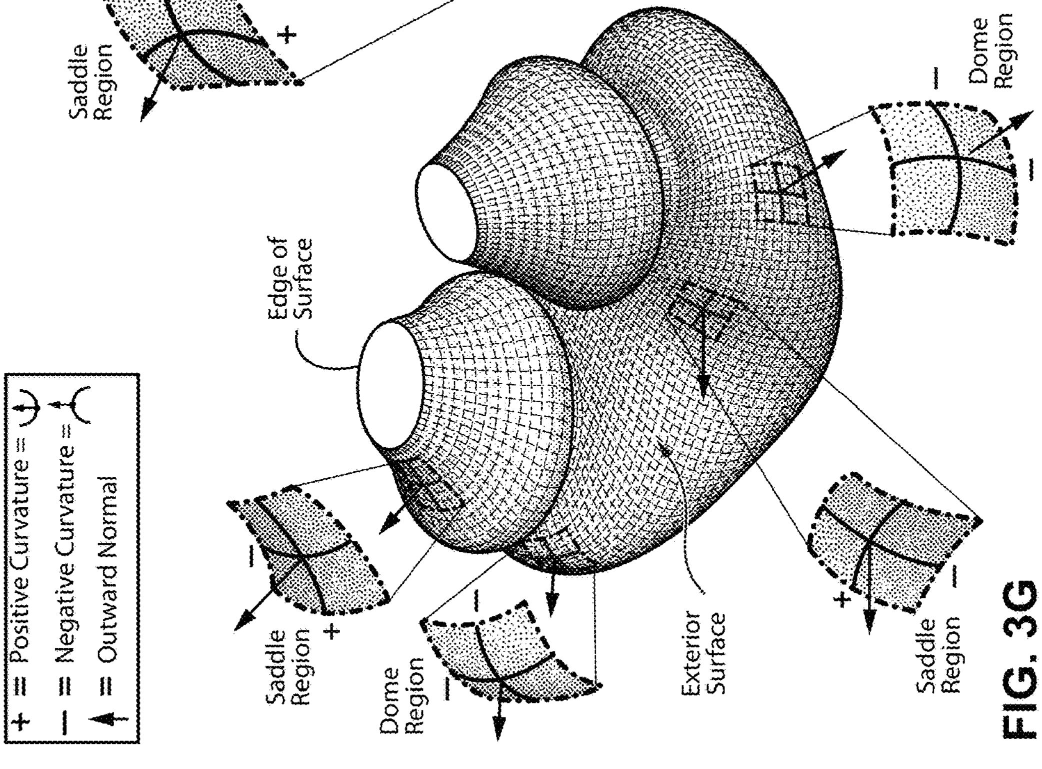

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
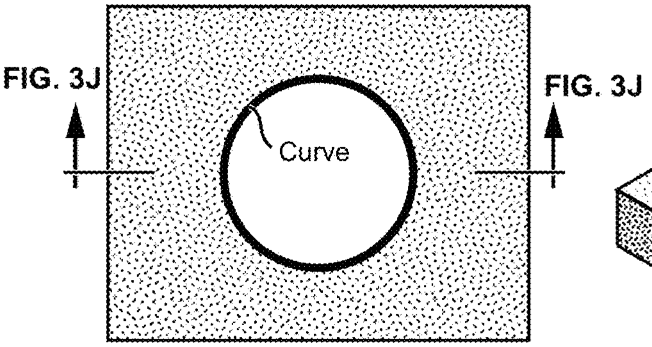

FIG. 3I shows the surface of a structure, with a one dimensional hole in the surface. The illustrated plane curve forms the boundary of a one dimensional hole.

Figure 3K:
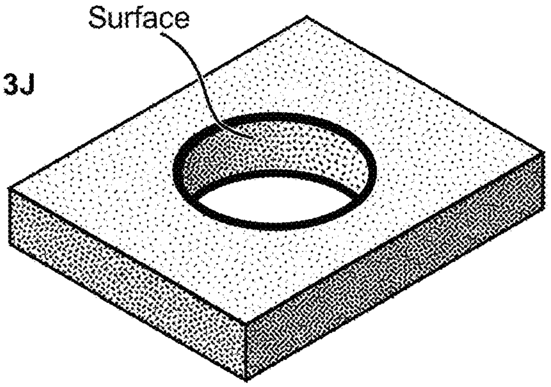
Figure 3J:
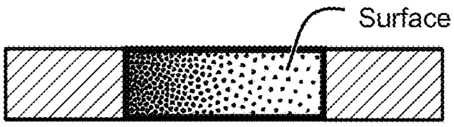

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
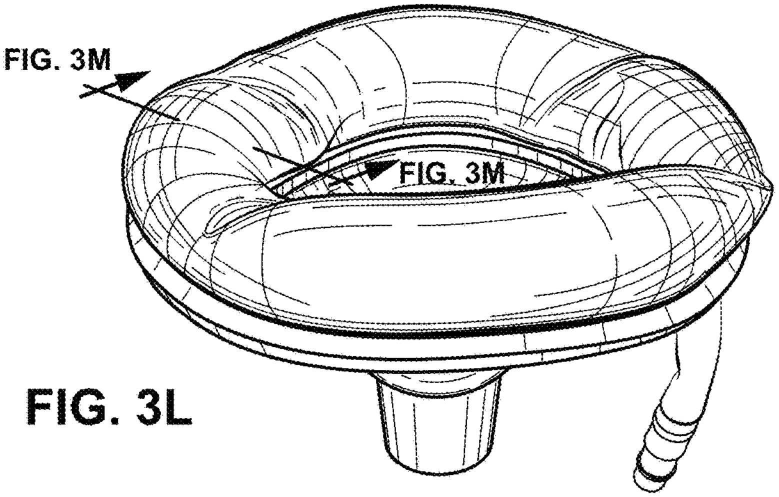

FIG. 3L shows a mask having an inflatable bladder as a cushion.

Figure 3M:
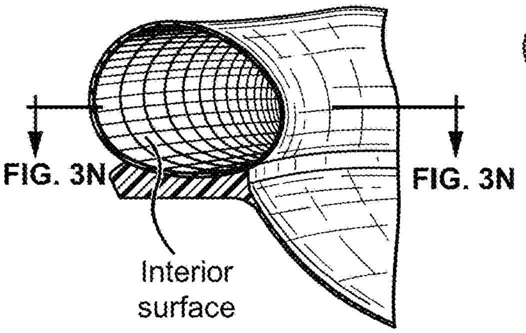

FIG. 3M shows a cross-section through the mask of FIG. 3L, and shows the interior surface of the bladder. The interior surface bounds the two dimensional hole in the mask.

Figure 3N:
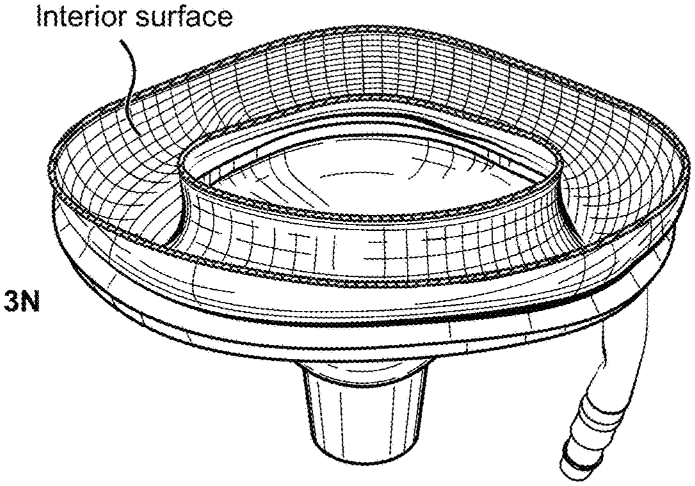

FIG. 3N shows a further cross-section through the mask of FIG. 3L. The interior surface is also indicated.

Figure 3O:
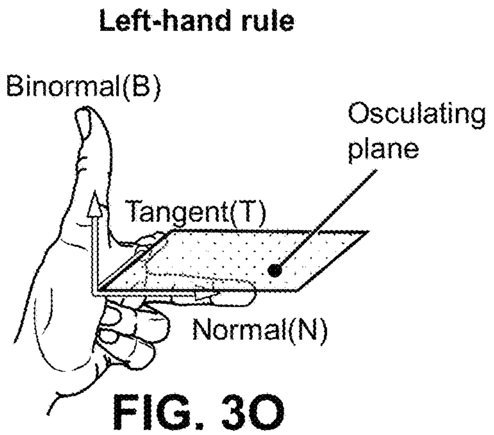

FIG. 3O illustrates a left-hand rule.

Figure 3P:
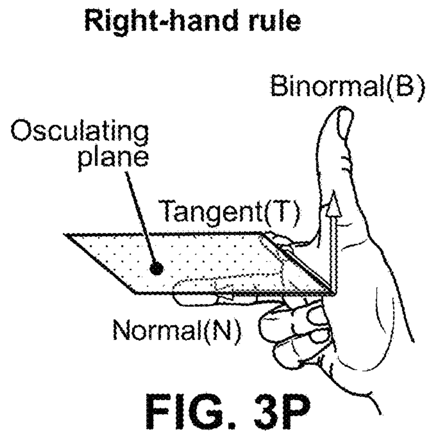

FIG. 3P illustrates a right-hand rule.

Figure 3Q:
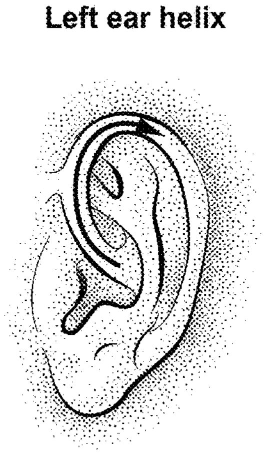

FIG. 3Q shows a left ear, including the left ear helix.

Figure 3S:
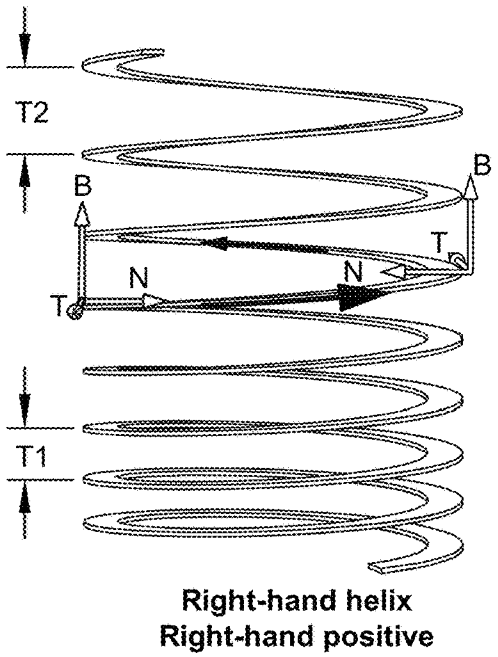
Figure 3R:
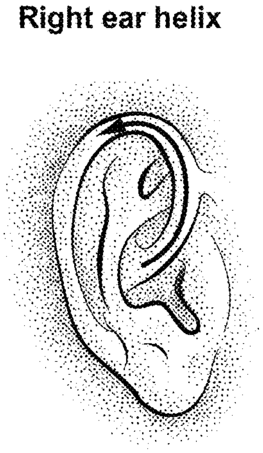

FIG. 3R shows a right ear, including the right ear helix.

FIG. 3S shows a right-hand helix.

Figure 3T:
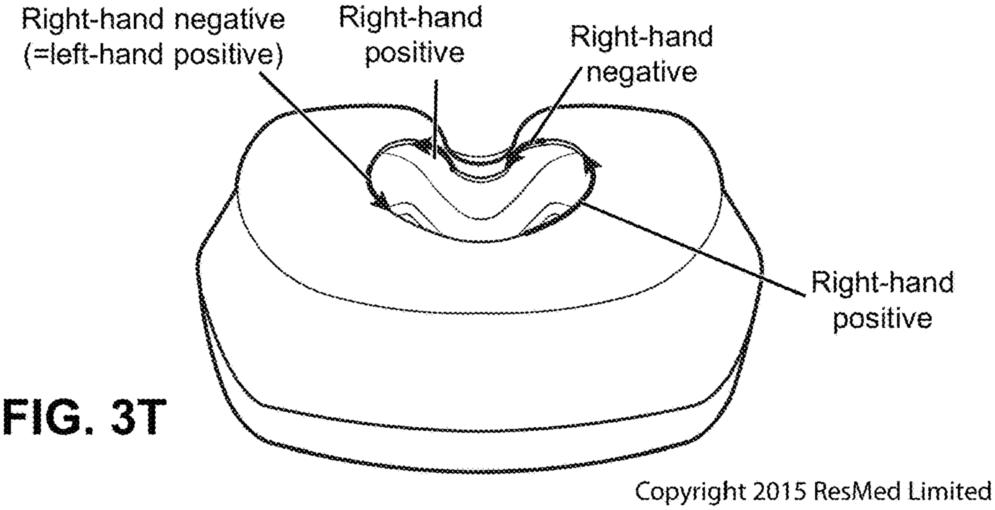

FIG. 3T shows a view of a mask, including the sign of the torsion of the space curve defined by the edge of the sealing membrane in different regions of the mask.

Figure 3U:
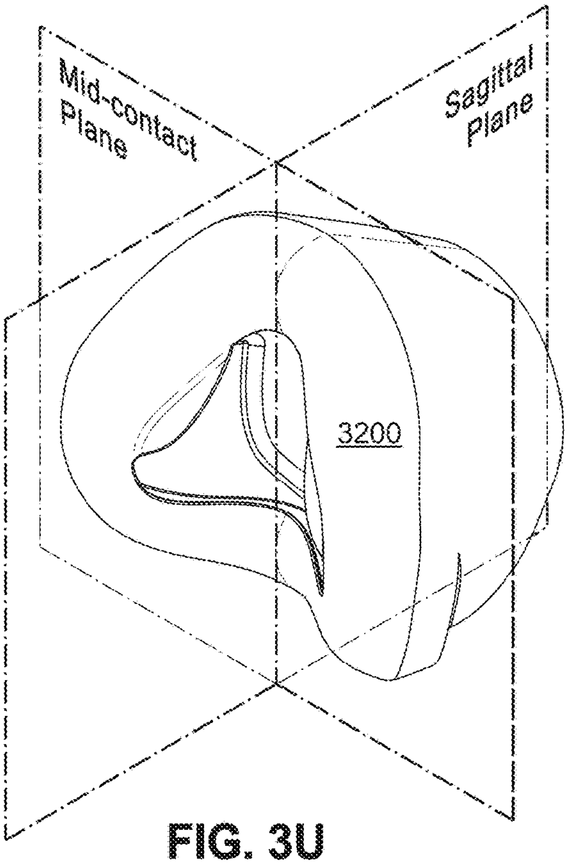

FIG. 3U shows a view of a plenum chamber 3200 showing a sagittal plane and a mid-contact plane.

Figure 3V:
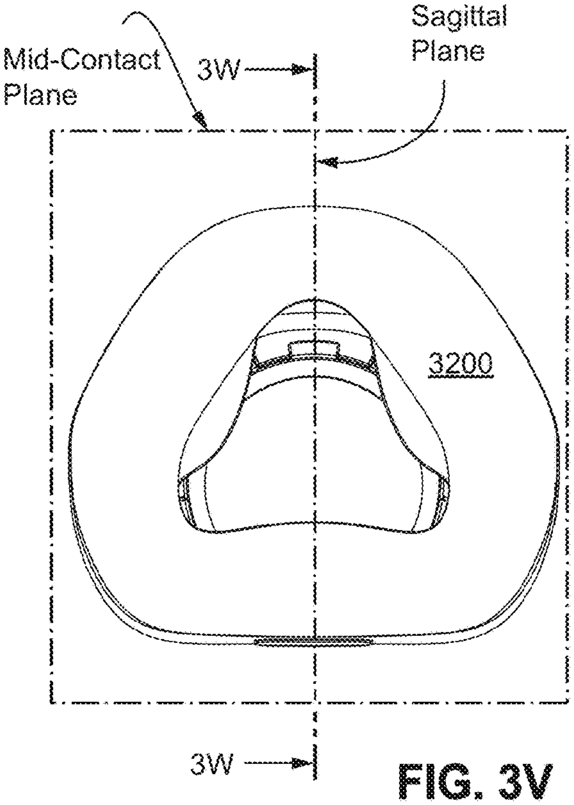

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
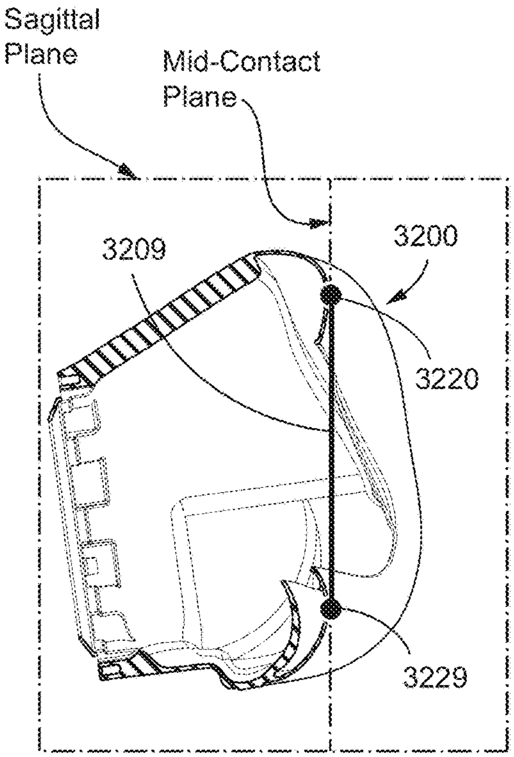

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3209 which lies on the sagittal plane and just touches the cushion of the plenum chamber at two points on the sagittal plane: a superior point 3220 and an inferior point 3229. Depending on the geometry of the cushion in this region, the mid-contact plane may be a tangent at both the superior and inferior points.

Figure 3X:
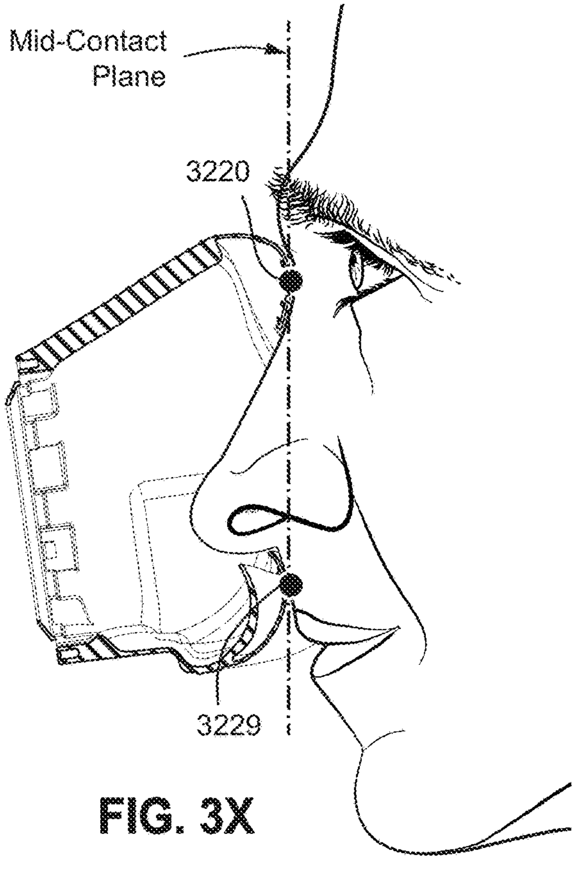

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3229 sits on the lip superior.

4.4 RPT Device

Figure 4A:
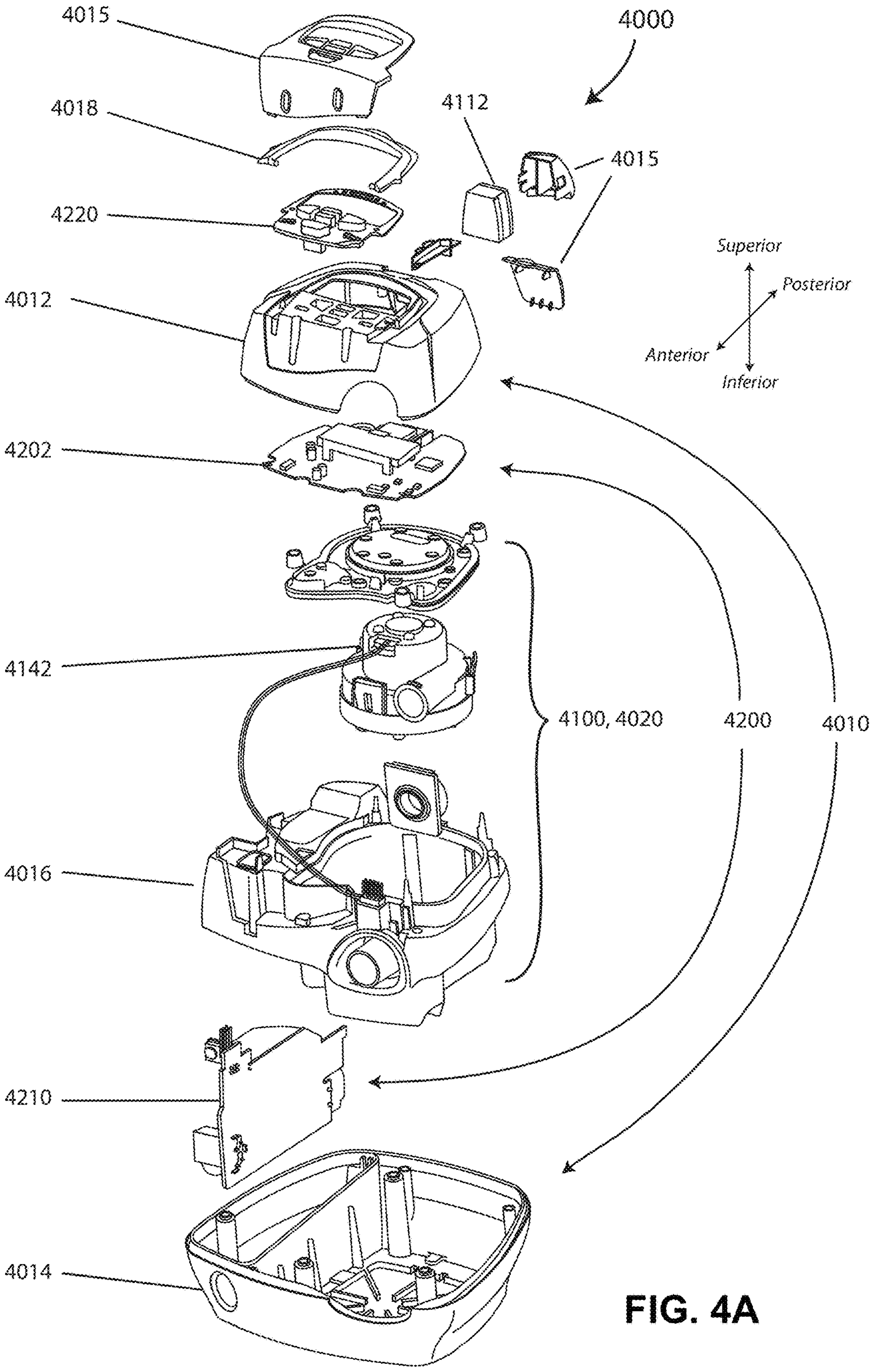

FIG. 4A shows an RPT device in accordance with one form of the present technology.

Figure 4B:
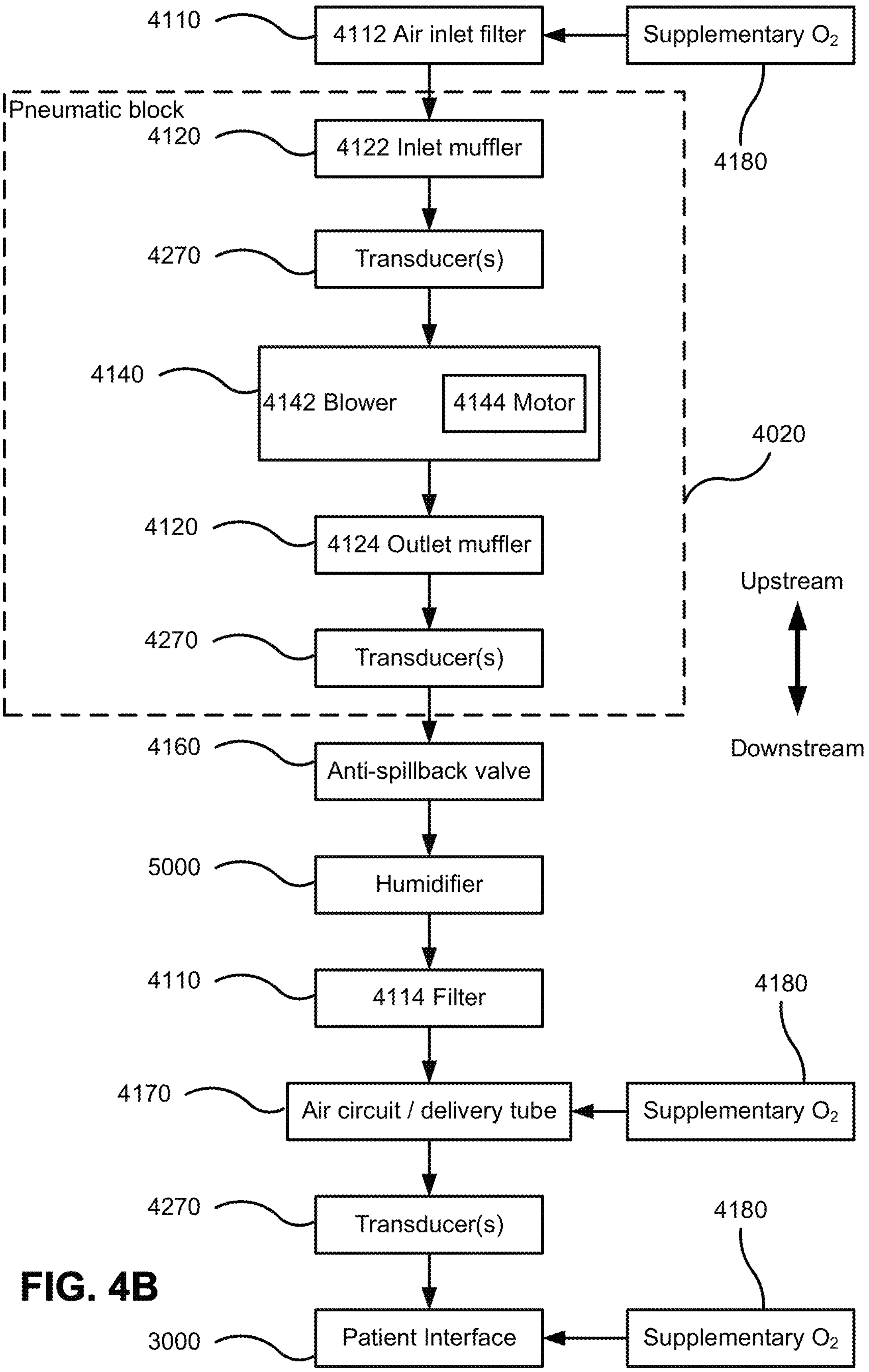

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

Figure 5A:
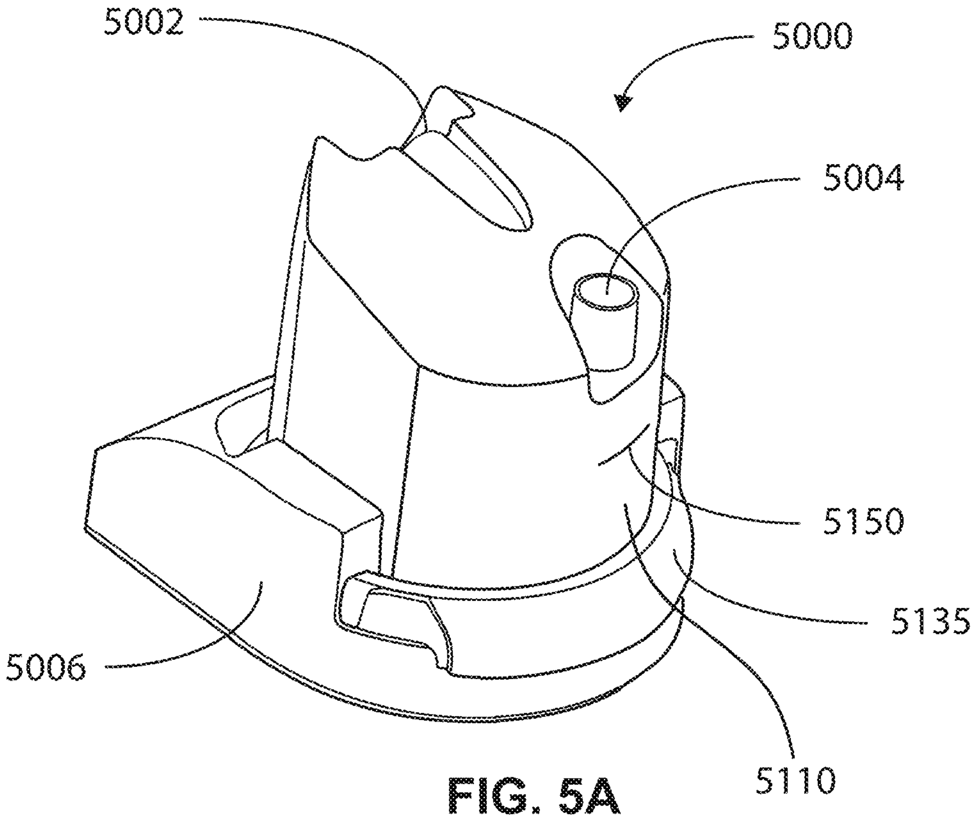

FIG. 5A shows an isometric view of a humidifier in accordance with one form of the present technology.

Figure 5B:
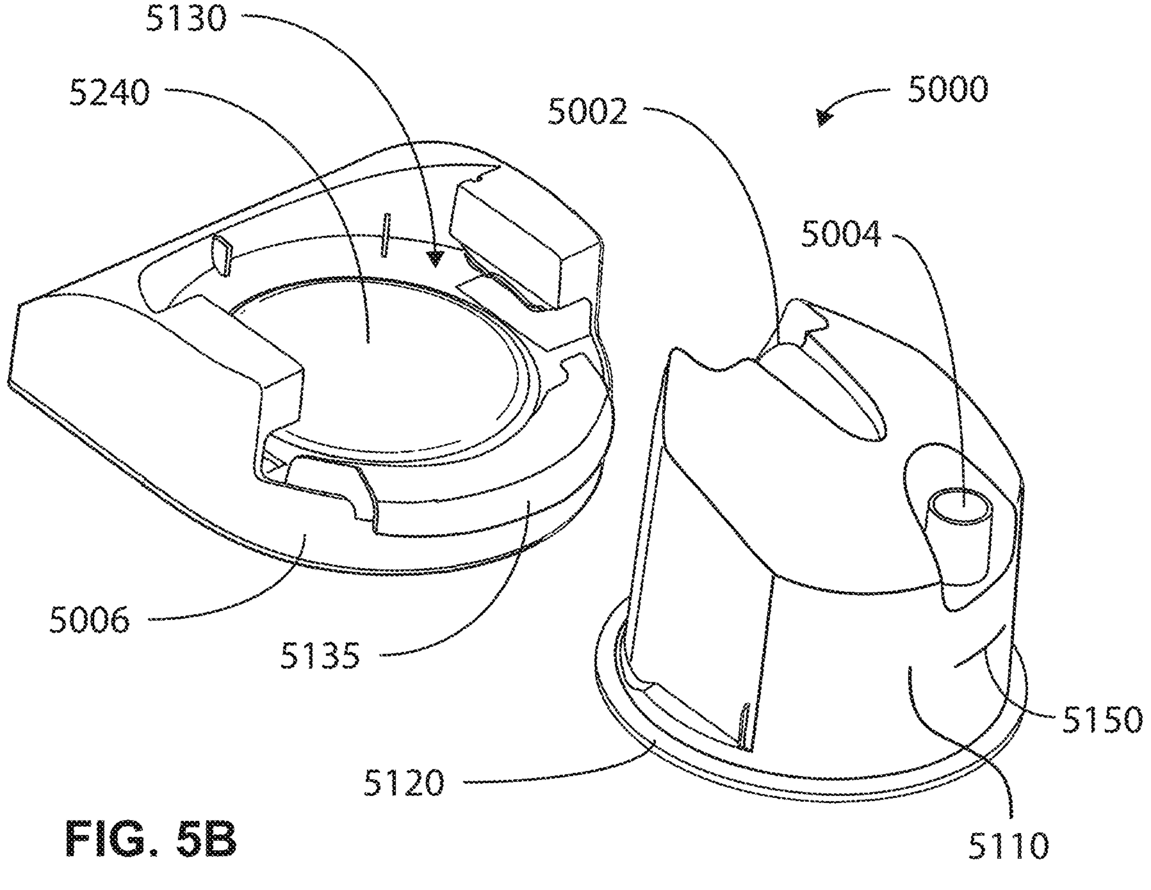

FIG. 5B shows an isometric view of a humidifier in accordance with one form of the present technology, showing a humidifier reservoir 5110 removed from the humidifier reservoir dock 5130.

Figure 5C:
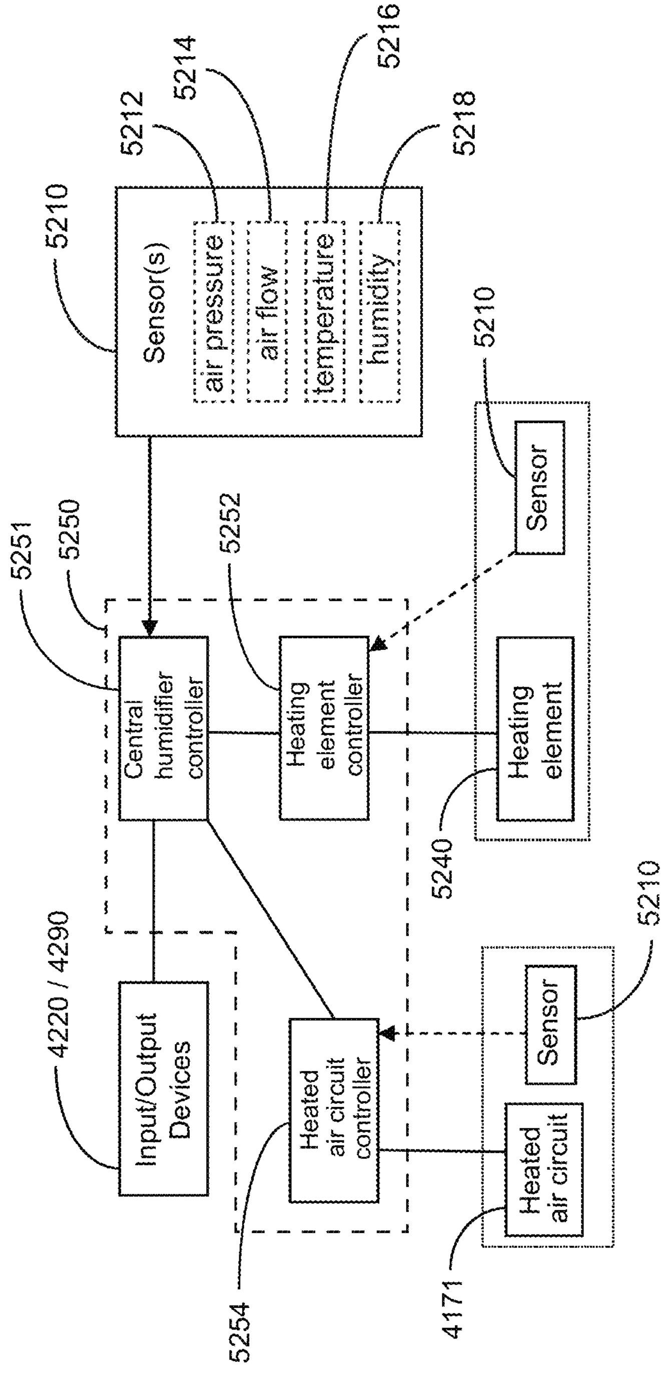

FIG. 5C shows a schematic of a humidifier in accordance with one form of the present technology.

4.6 Breathing Waveforms

Figure 6:
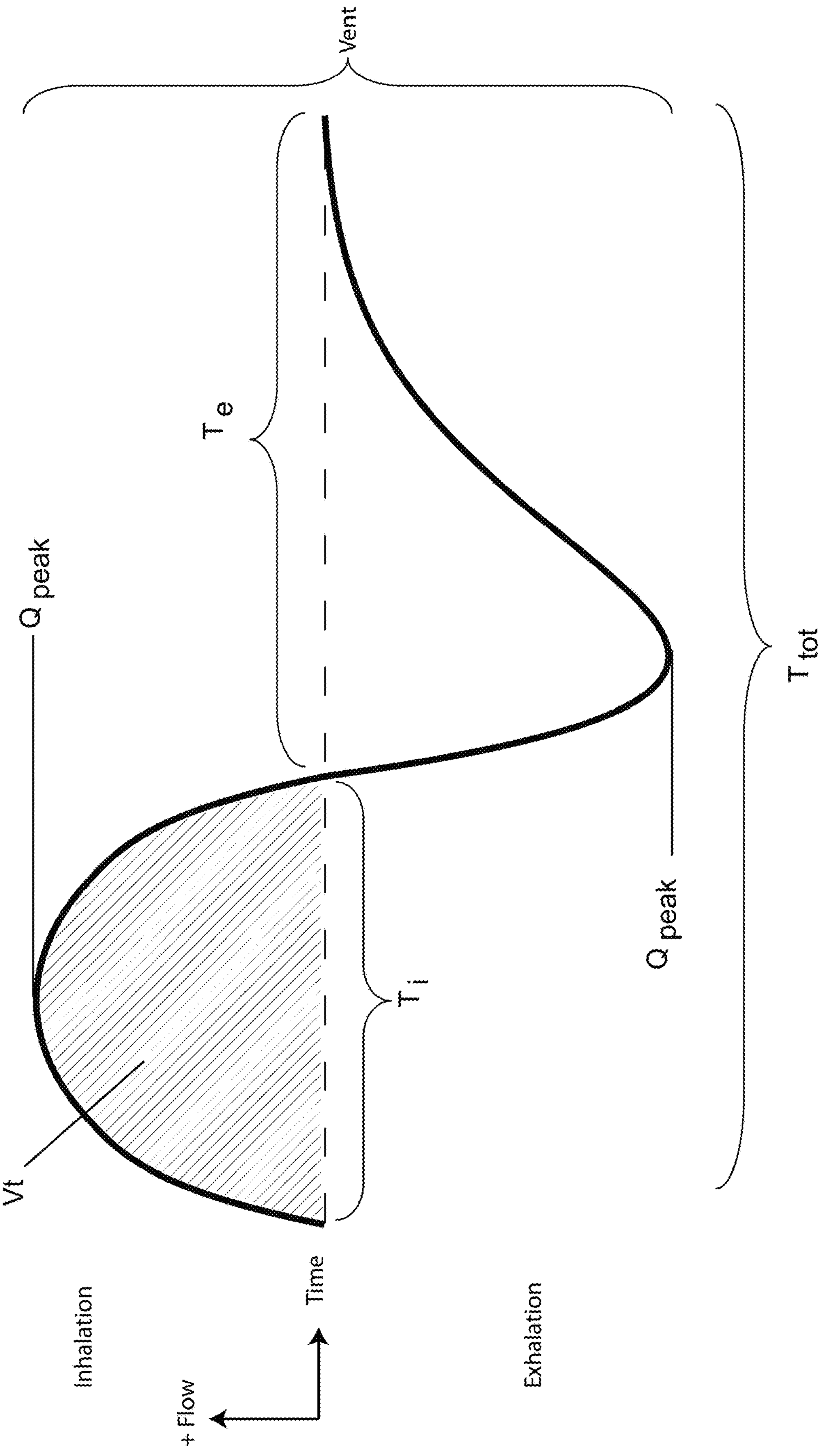

FIG. 6 shows a model typical breath waveform of a person while sleeping.

4.7 First Embodiment of a Patient Interface of the Present Technology

Figures 1, 7:
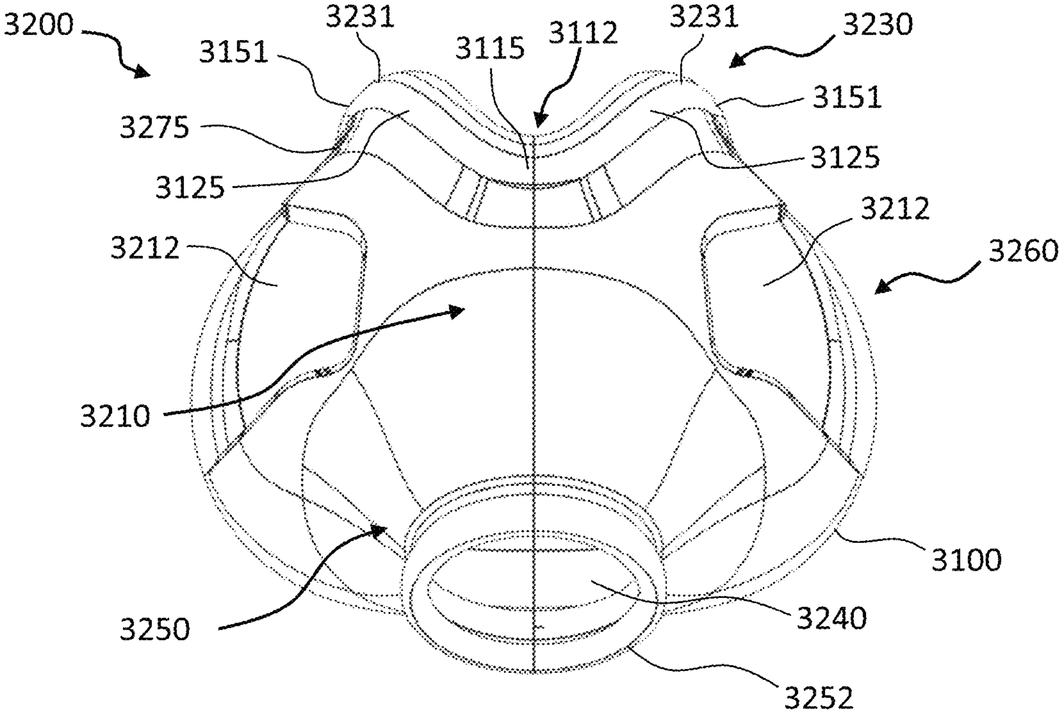

FIG. 7-1 is a front view of a plenum chamber 3200 in accordance with one form of the present technology.

Figures 2, 7:
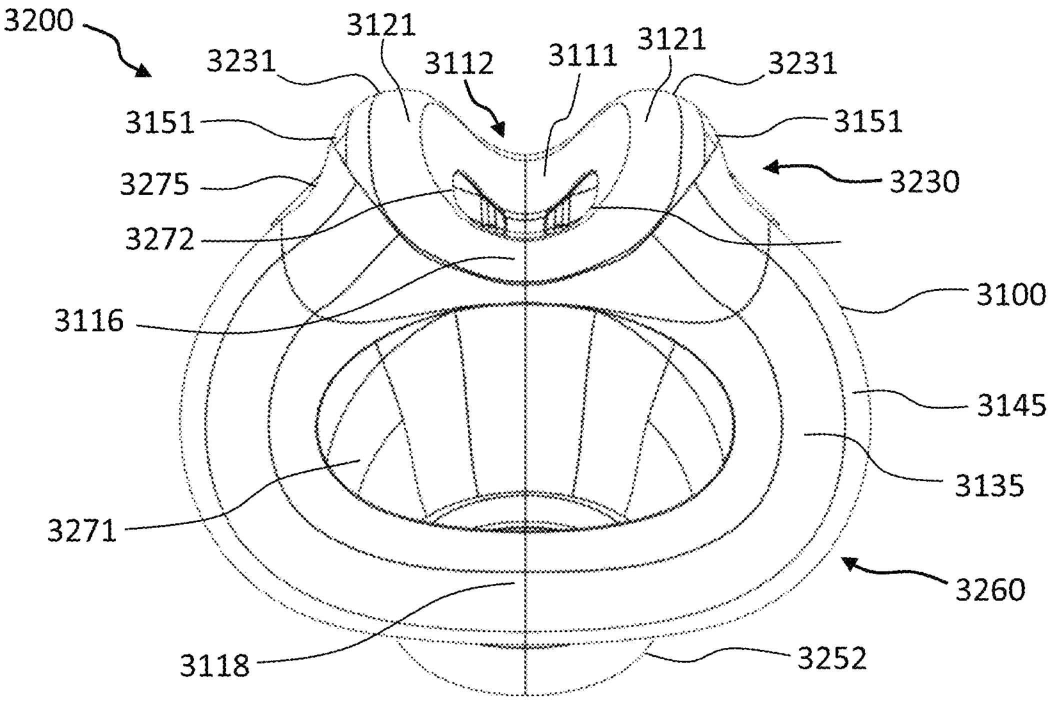

FIG. 7-2 is a rear view of the plenum chamber 3200 of FIG. 7-1.

Figures 3, 7:
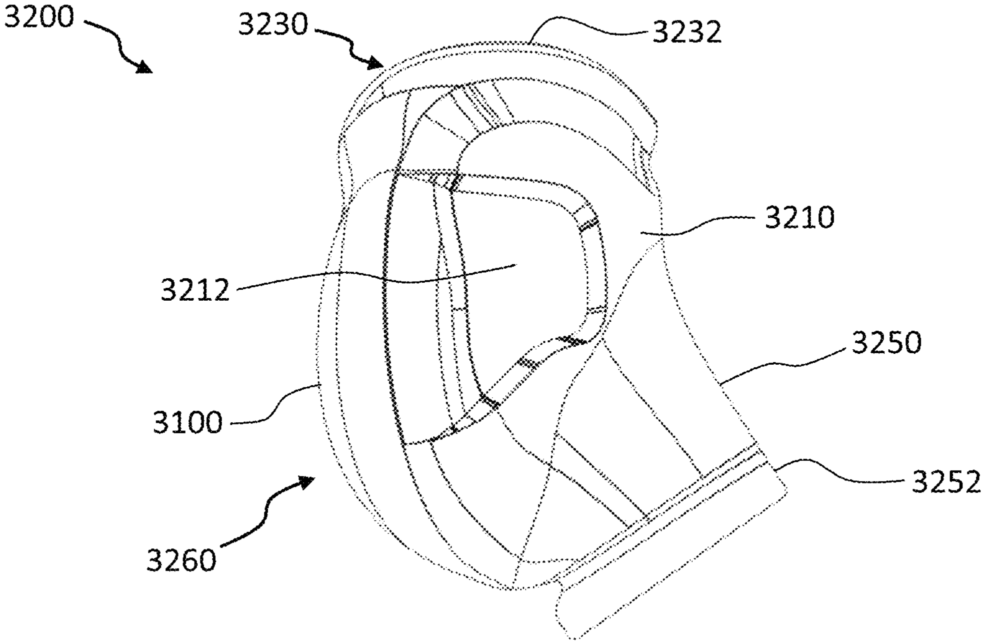

FIG. 7-3 is a side view of the plenum chamber 3200 of FIG. 7-1.

Figures 4, 7:
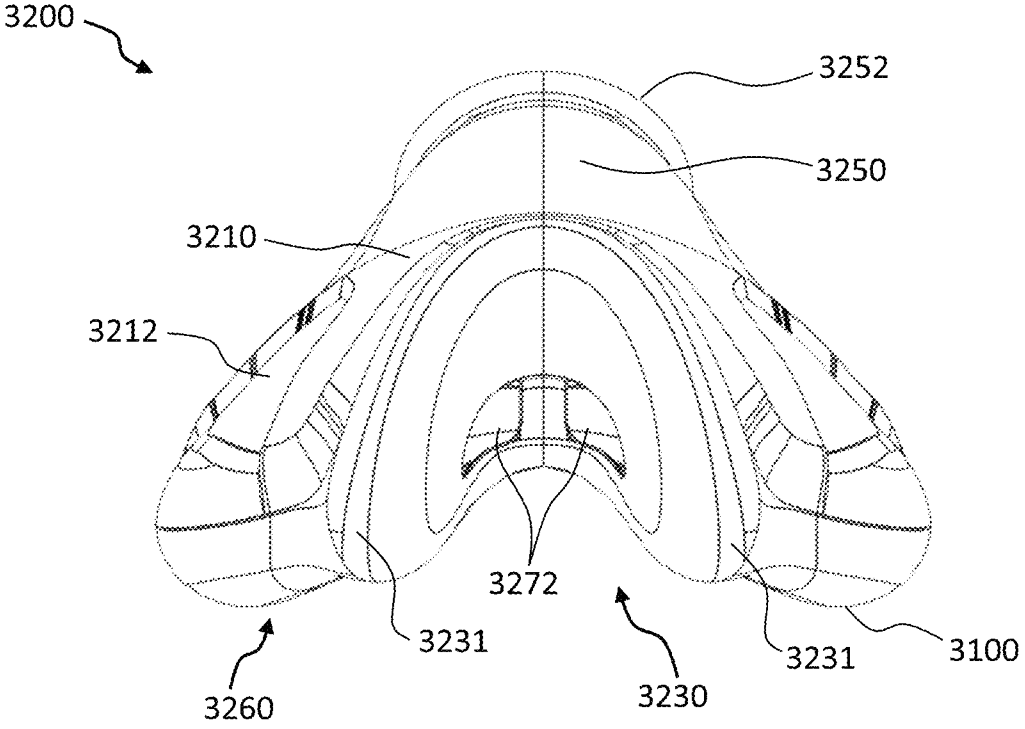

FIG. 7-4 is a top view of the plenum chamber 3200 of FIG. 7-1.

Figures 5, 7:
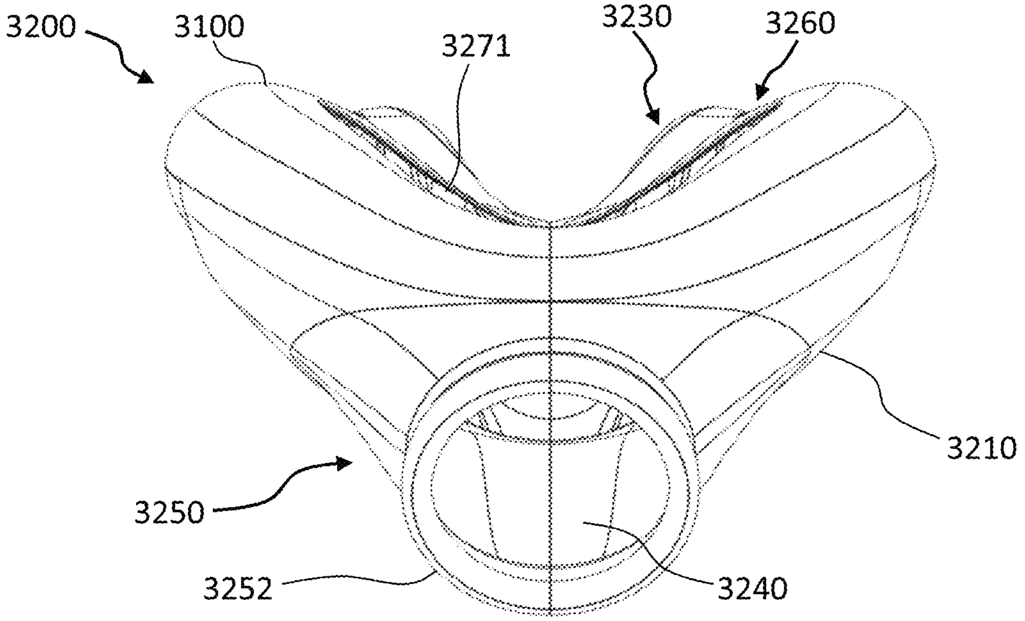
Figures 6, 7:
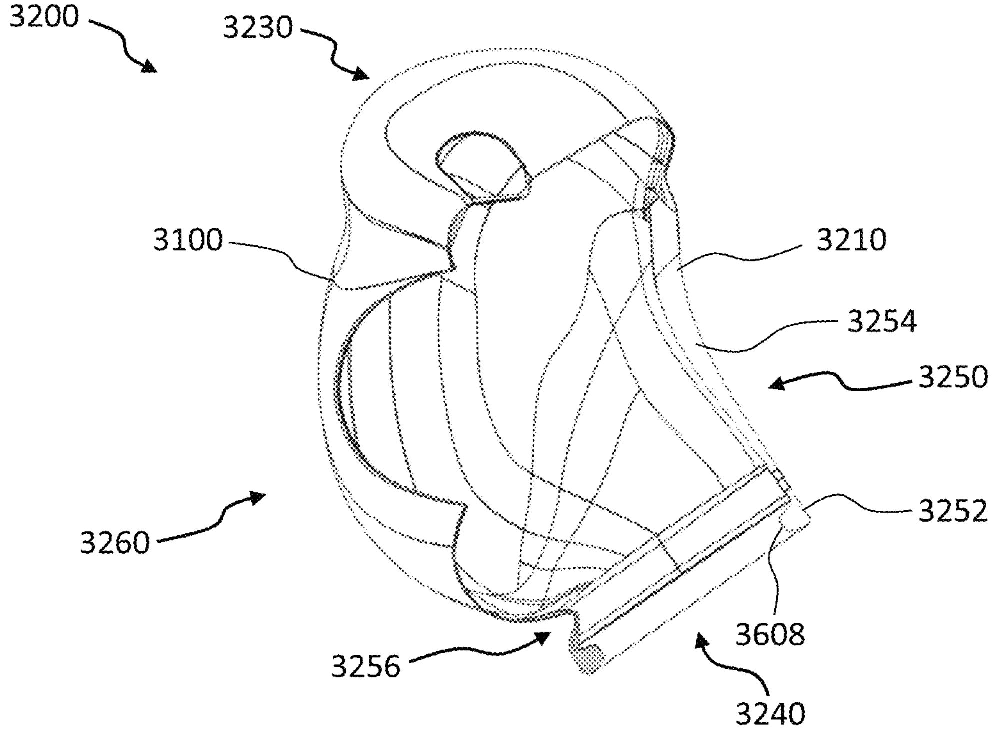

FIG. 7-5 is a bottom view of the plenum chamber 3200 of FIG. 7-1.

FIG. 7-6 is a side cross section view of the plenum chamber 3200 of FIG. 7-1.

Figures 1, 8:
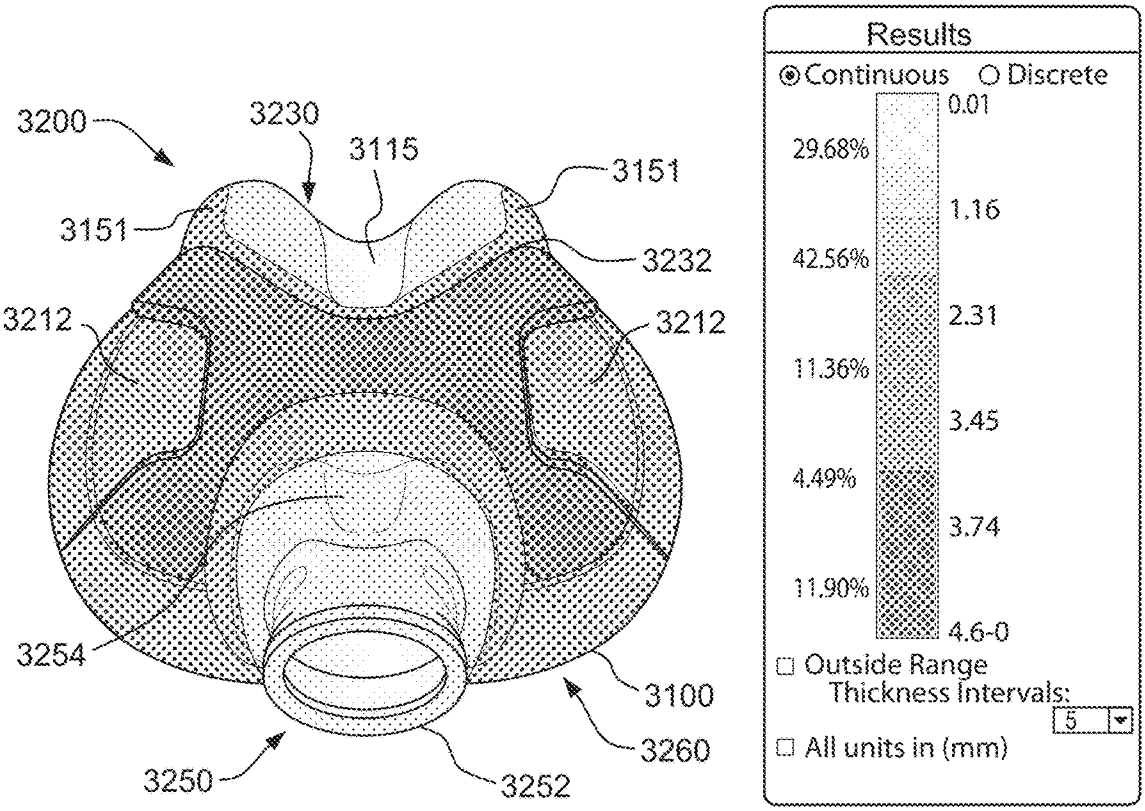
Figures 2, 8:
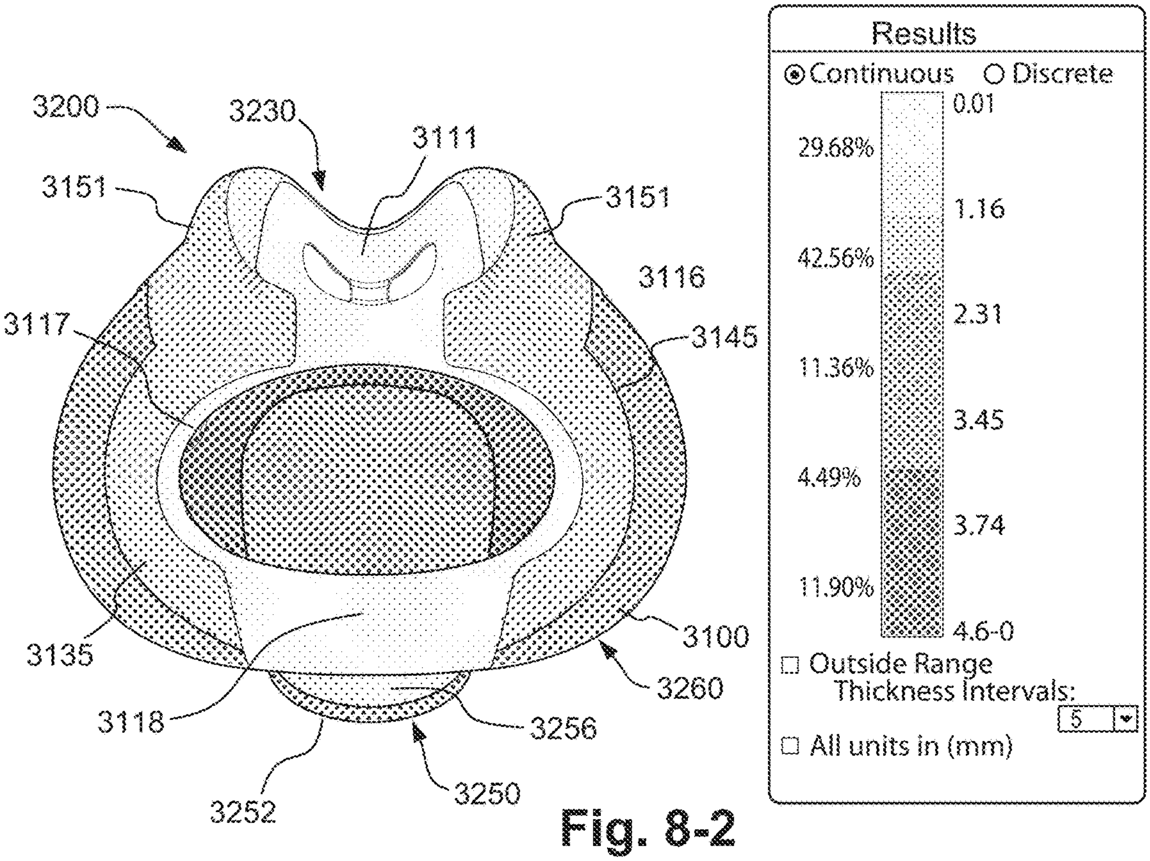
Figures 3, 8:
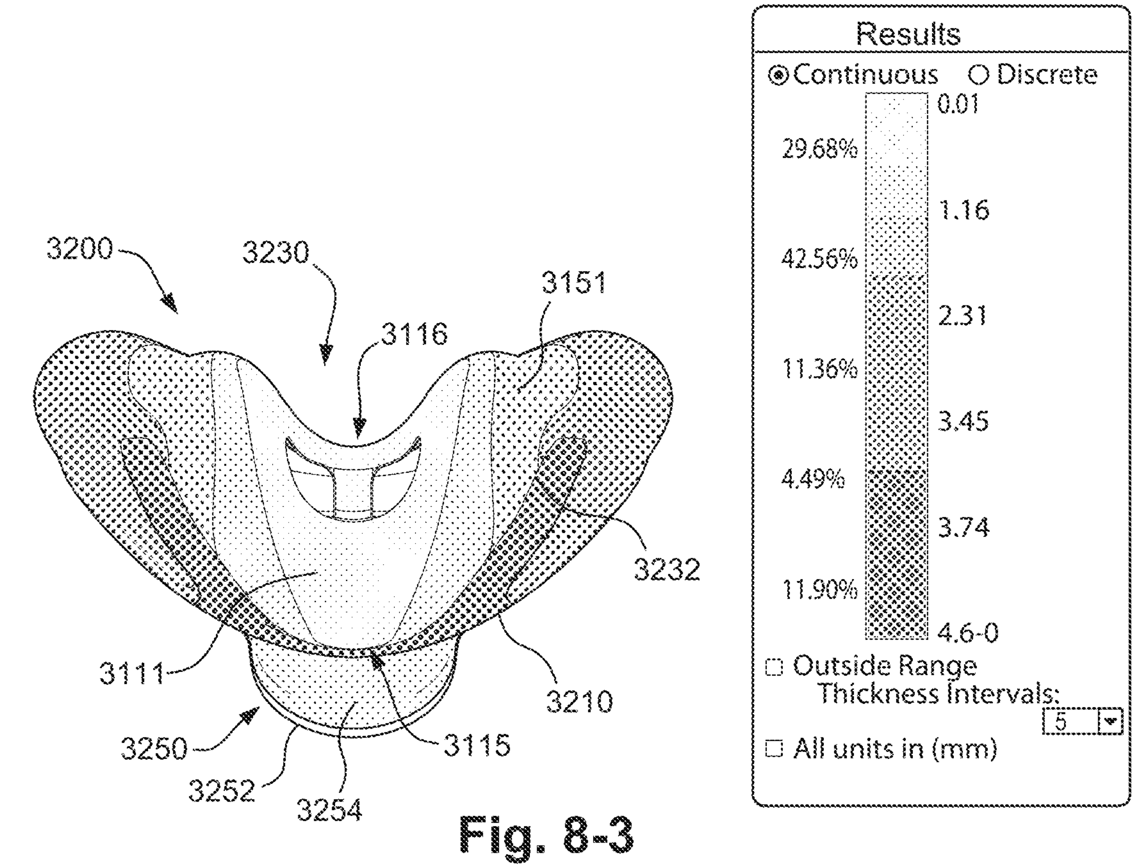
Figures 4, 8:
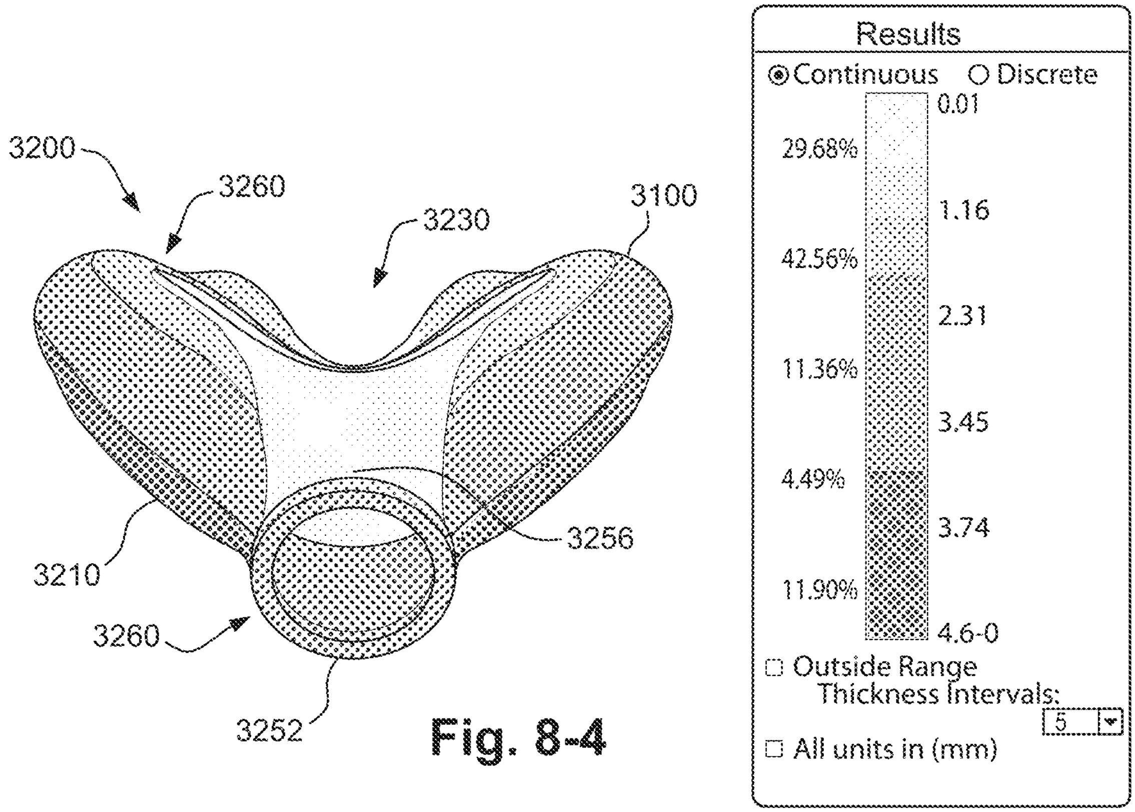
Figures 5, 8:
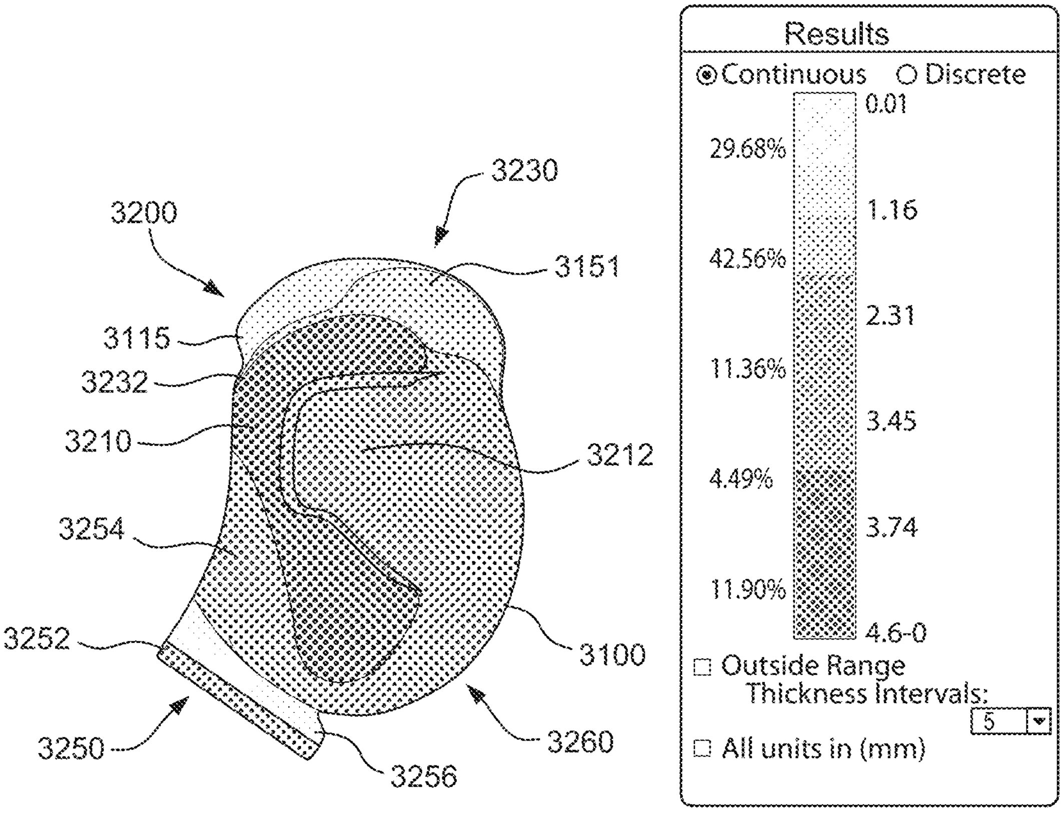

FIG. 8-1 is a front view of a wall thickness heatmap of the plenum chamber 3200 of FIG. 7-1.

FIG. 8-2 is a rear view of a wall thickness heatmap of the plenum chamber 3200 of FIG. 7-1.

FIG. 8-3 is a side view of a wall thickness heatmap of the plenum chamber 3200 of FIG. 7-1.

FIG. 8-4 is a top view of a wall thickness heatmap of the plenum chamber 3200 of FIG. 7-1.

FIG. 8-5 is a bottom view of a wall thickness heatmap of the plenum chamber 3200 of FIG. 7-1.

Figure 9:
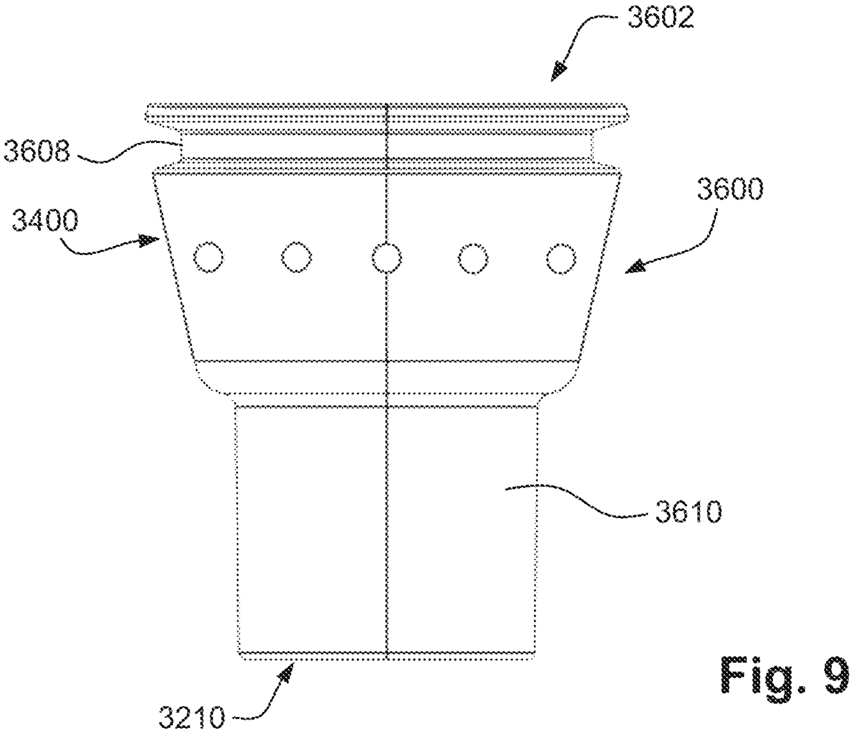

FIG. 9 is a side view of a connection port 3600 3200 in accordance with one form of the present technology.

Figures 1, 10:
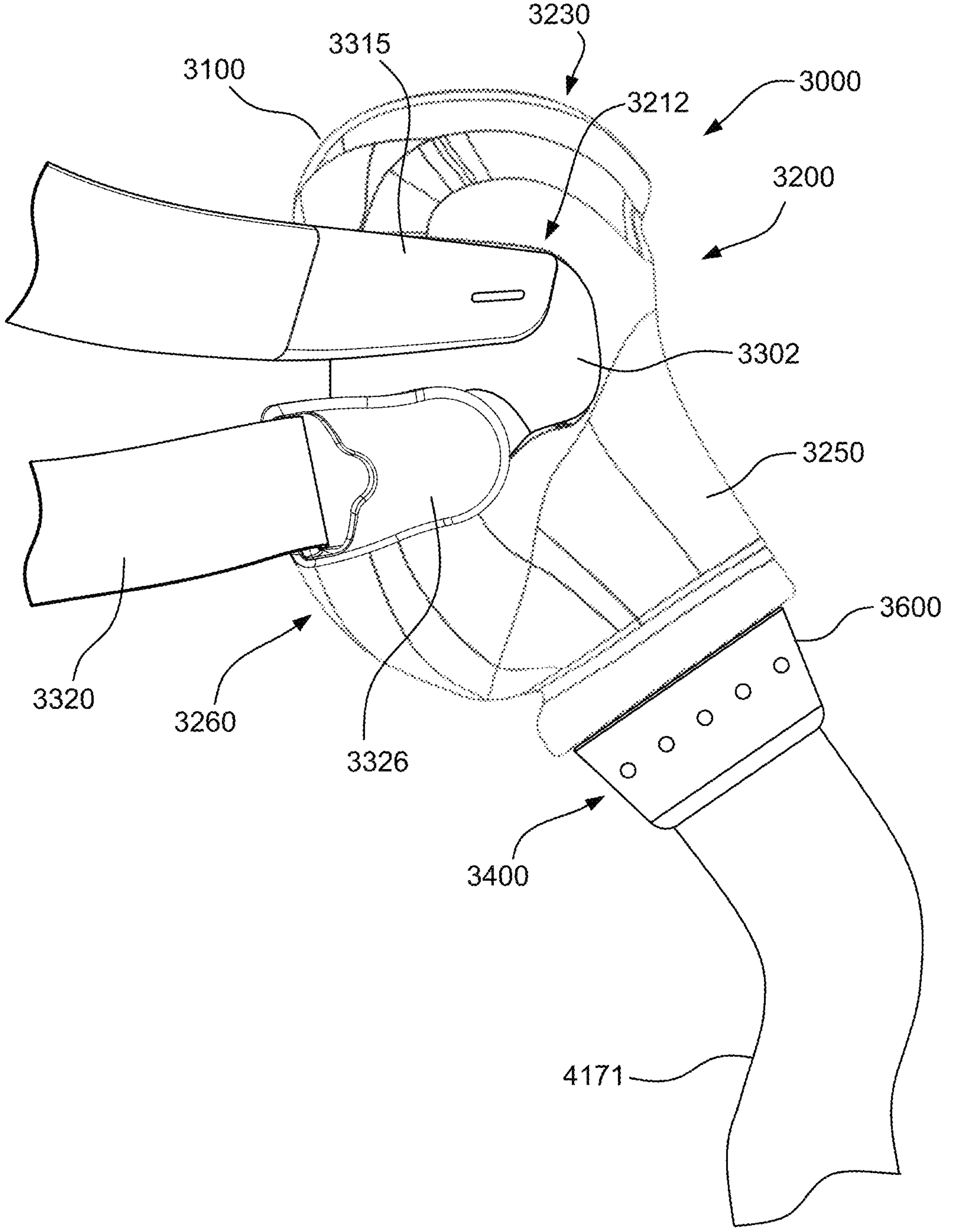
Figures 2, 10:
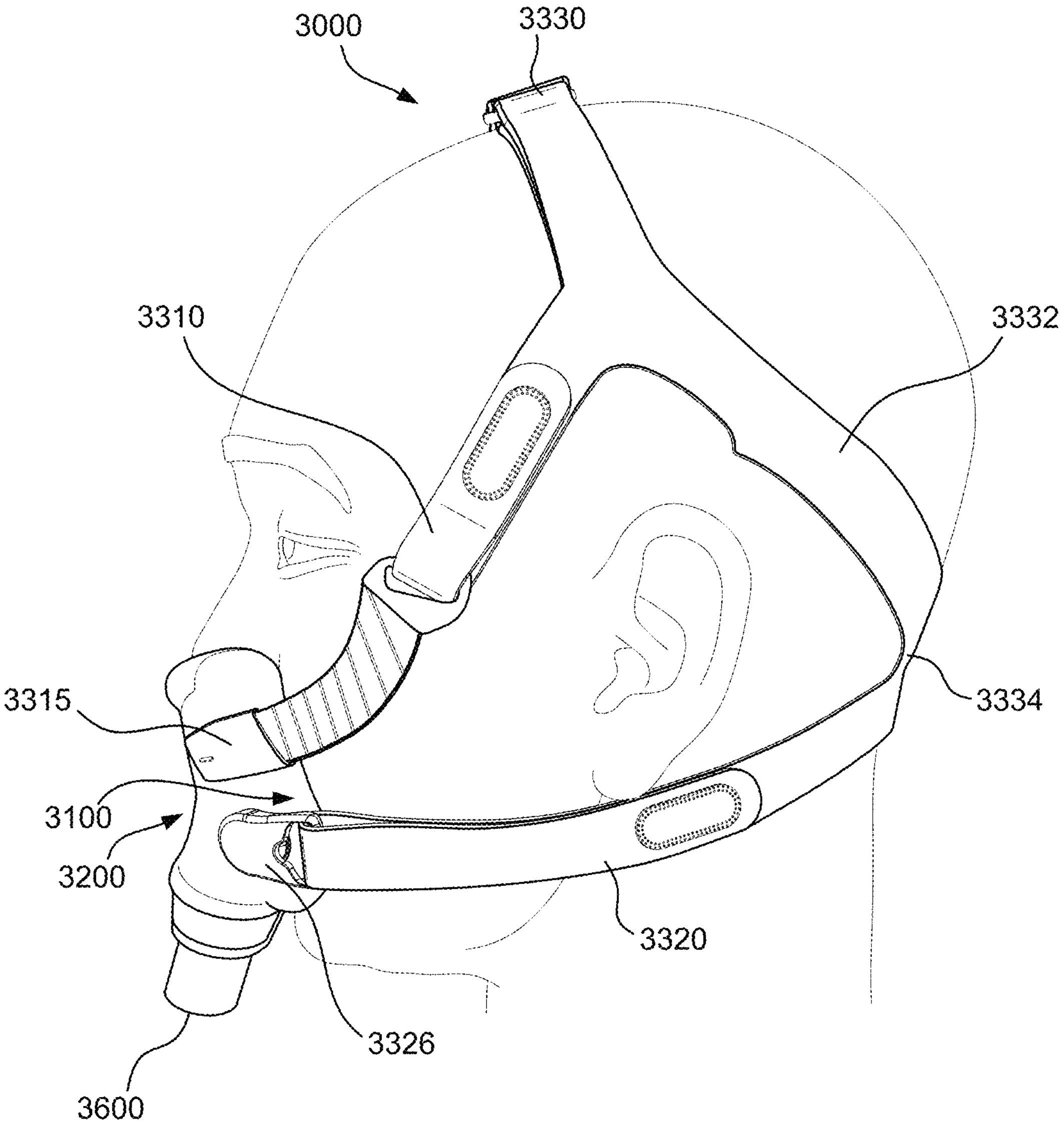

FIG. 10-1 is a first side view of a patient interface 3000 according to another example of the present technology.

FIG. 10-2 is a second side view of the patient interface 3000 of FIG. 10-1.

Figures 1, 11:
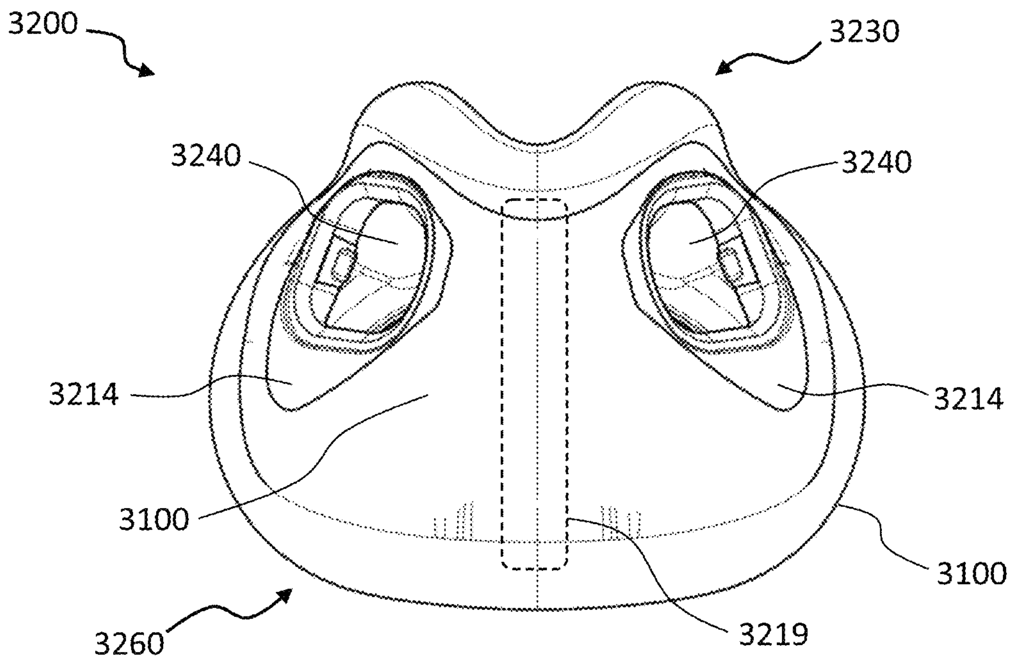
Figures 2, 11:
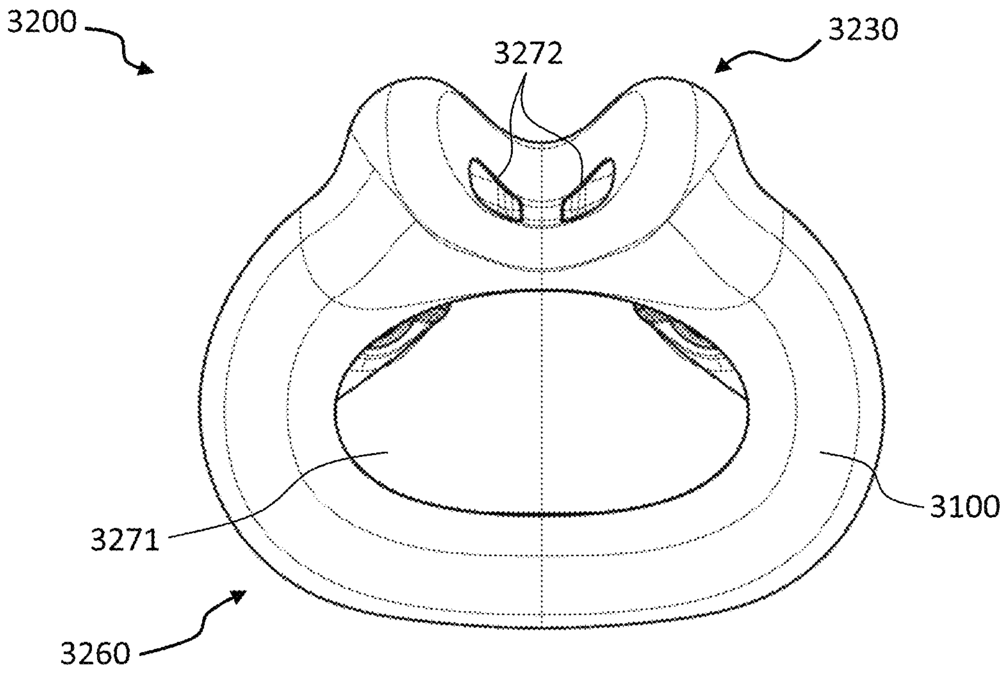
Figures 3, 11:
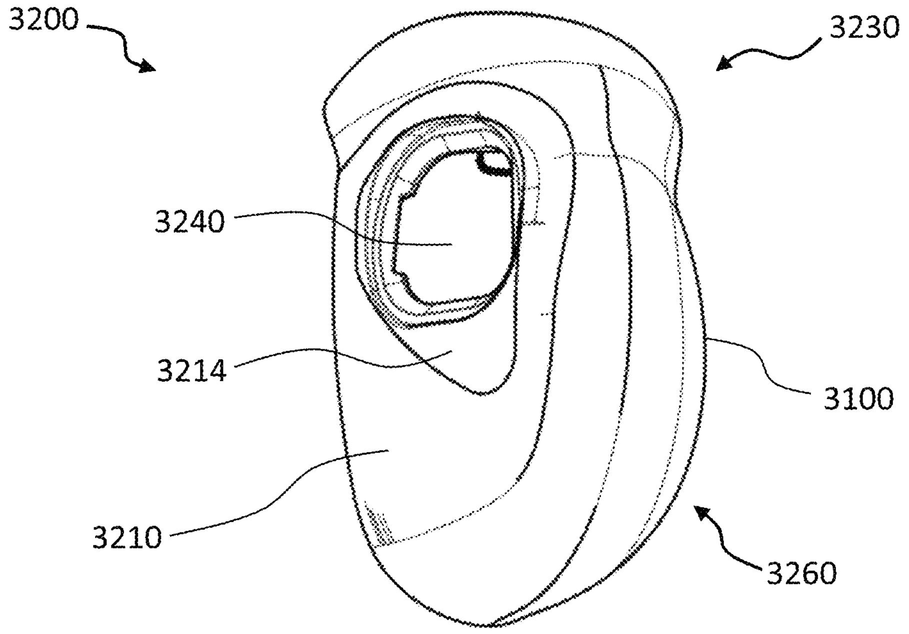
Figures 4, 11:
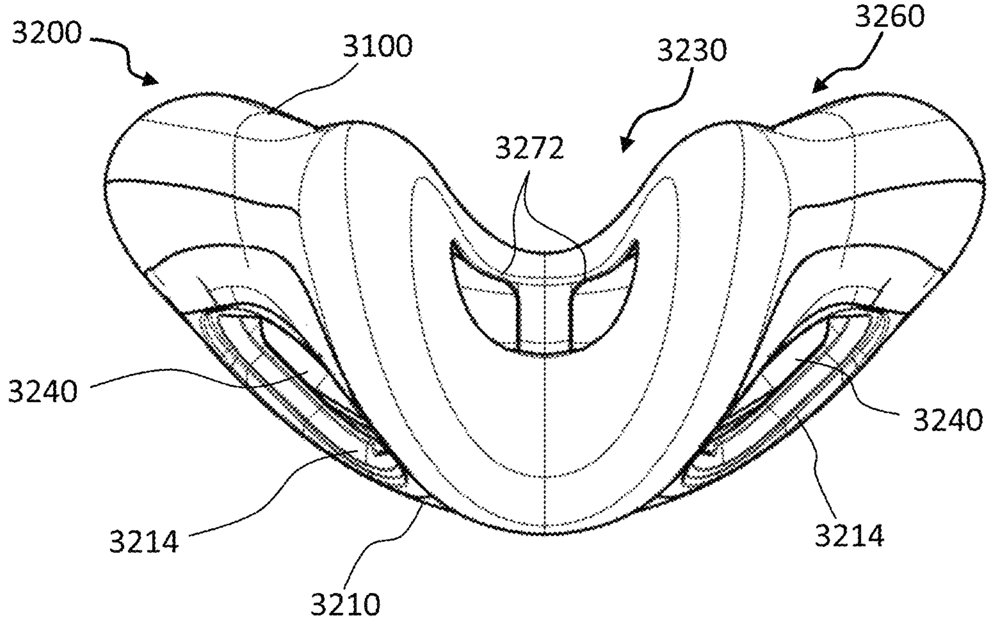
Figures 5, 11:
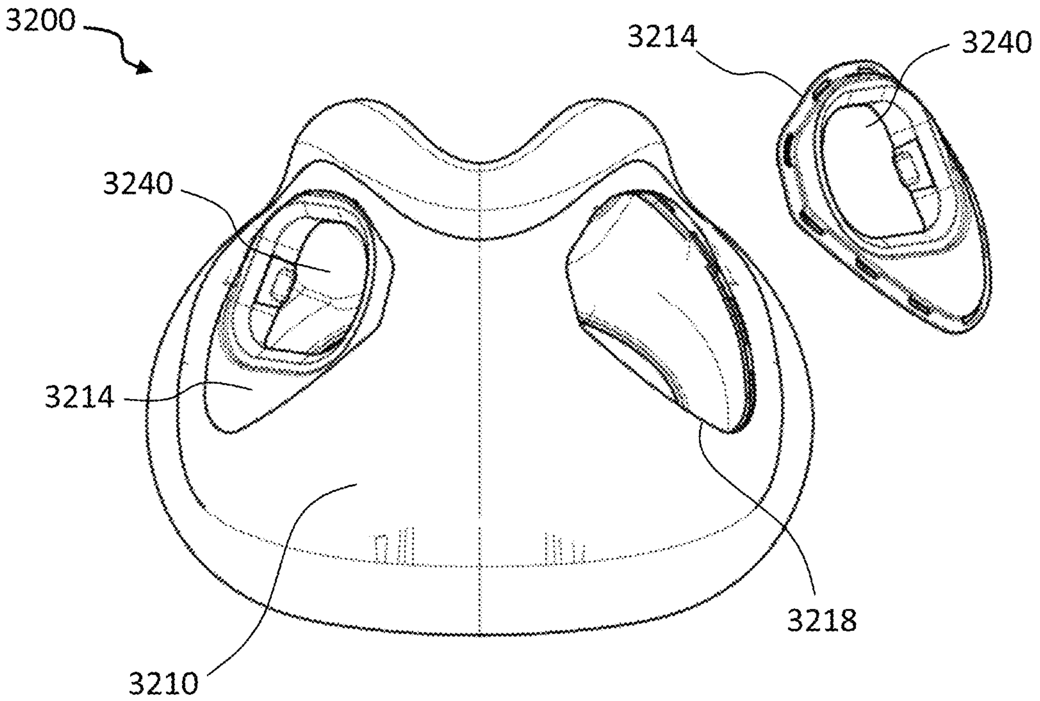

FIG. 11-1 is a front view of a plenum chamber 3200 in accordance with another form of the present technology.

FIG. 11-2 is a rear view of the plenum chamber 3200 of FIG. 11-1.

FIG. 11-3 is a side view of the plenum chamber 3200 of FIG. 11-1.

FIG. 11-4 is a top view of the plenum chamber 3200 of FIG. 11-1.

FIG. 11-5 is a front view of the plenum chamber 3200 of FIG. 11-1 with a lateral insert 3214 removed.

Figures 1, 12:
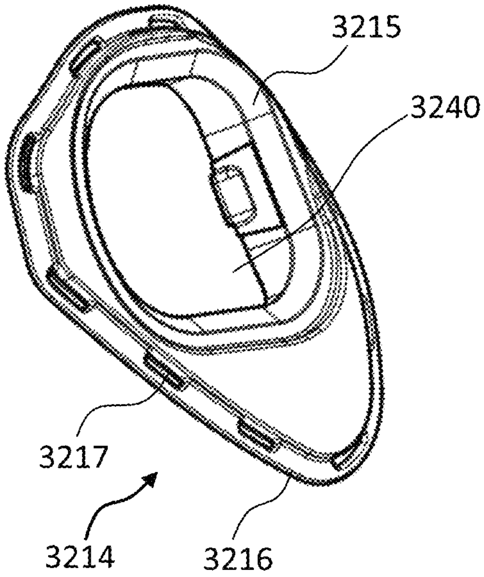
Figures 2, 12:
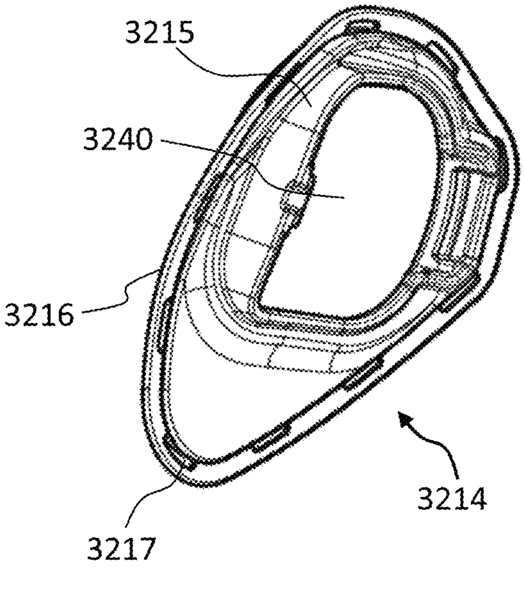

FIG. 12-1 is a front perspective view of the lateral insert 3214 of FIG. 11-1.

FIG. 12-2 is a rear perspective view of the lateral insert 3214 of FIG. 11-1.

Figures 1, 13:
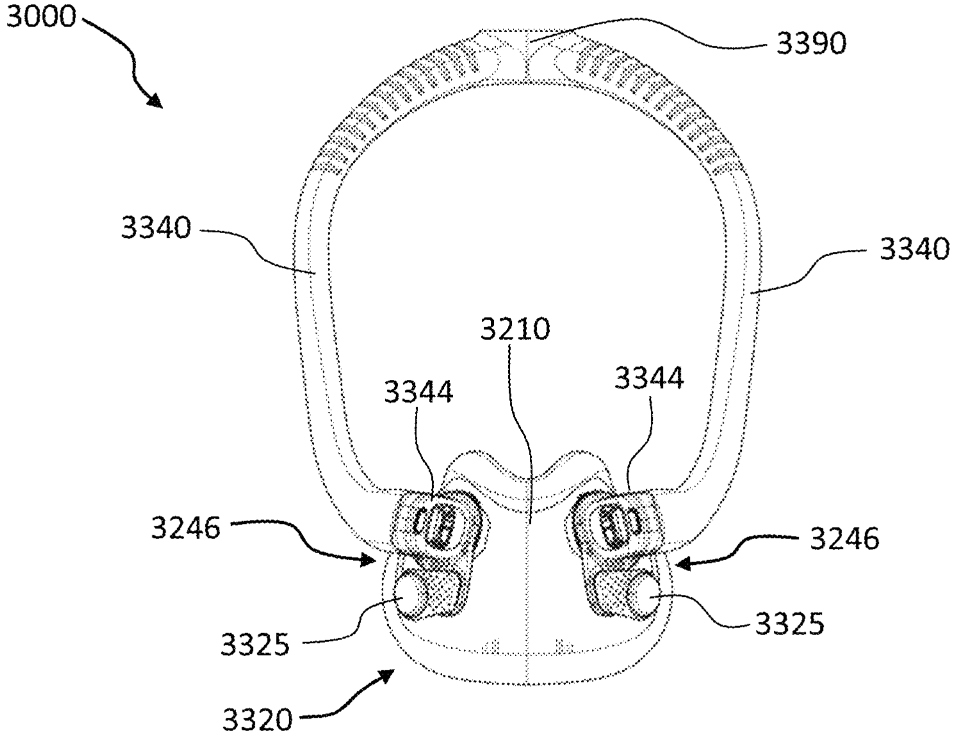
Figures 2, 13:
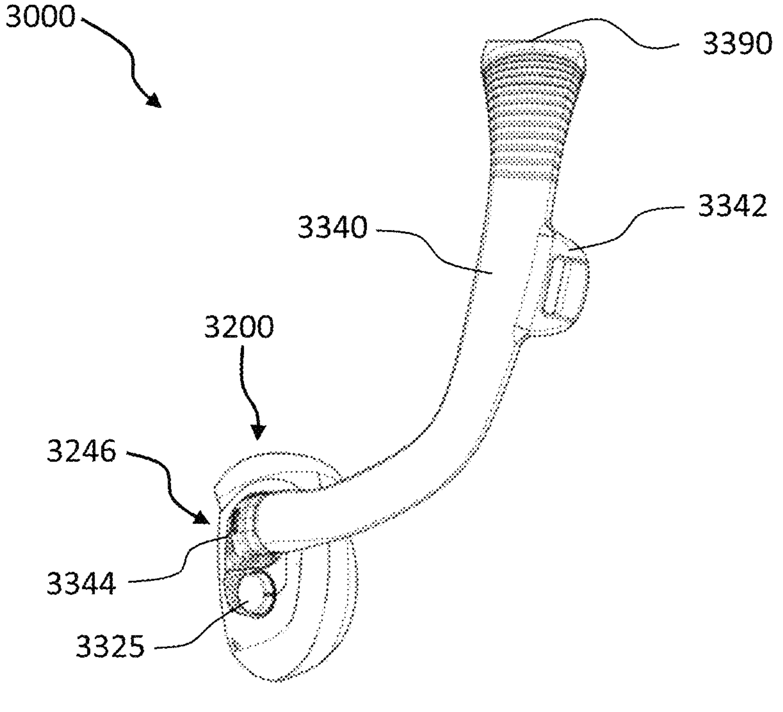
Figures 3, 13:
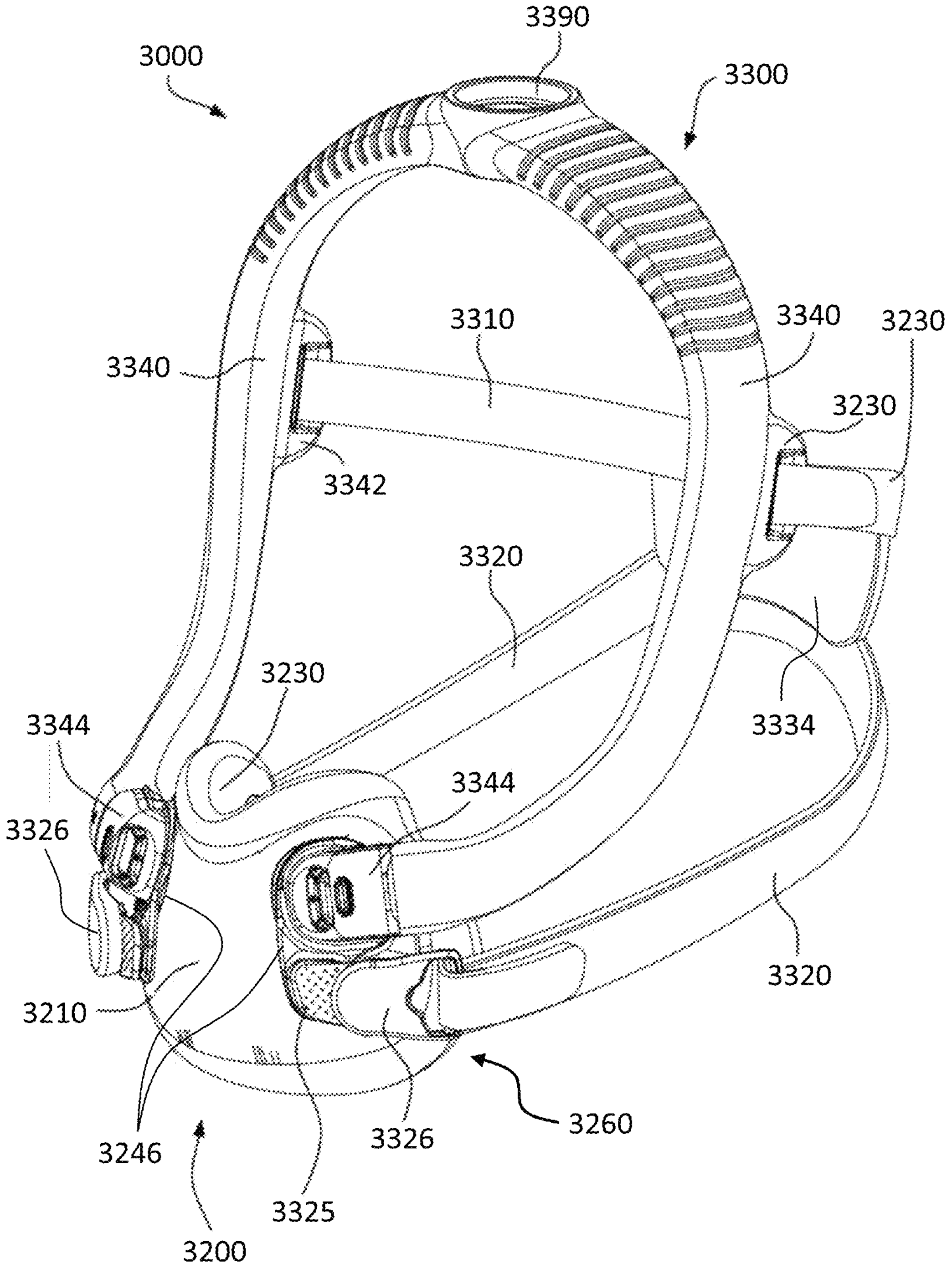

FIG. 13-1 is a front view of a patient interface 3000 according to another example of the present technology.

FIG. 13-2 is a side view of the patient interface 3000 of FIG. 13-1.

FIG. 13-3 is a perspective view of the patient interface 3000 of FIG. 13-1.

Figures 1, 14:
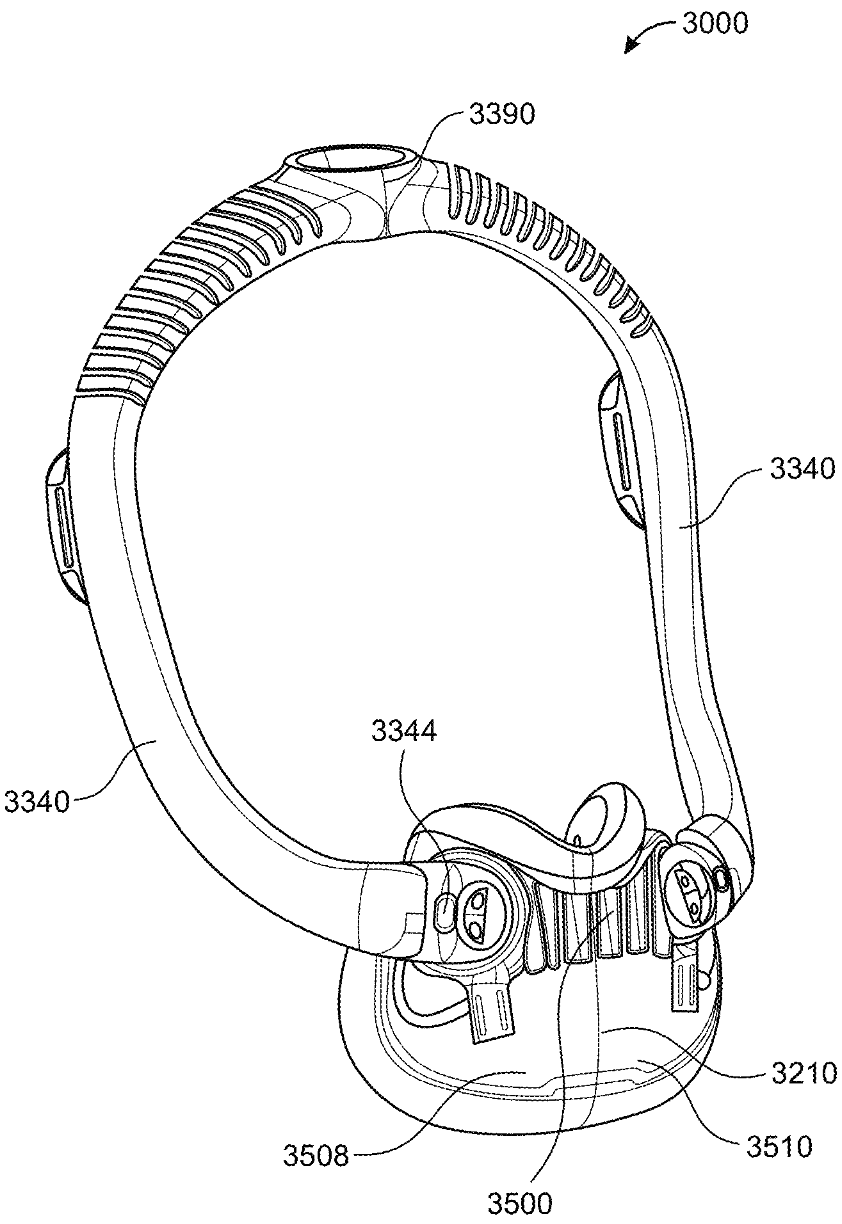
Figures 2, 14:
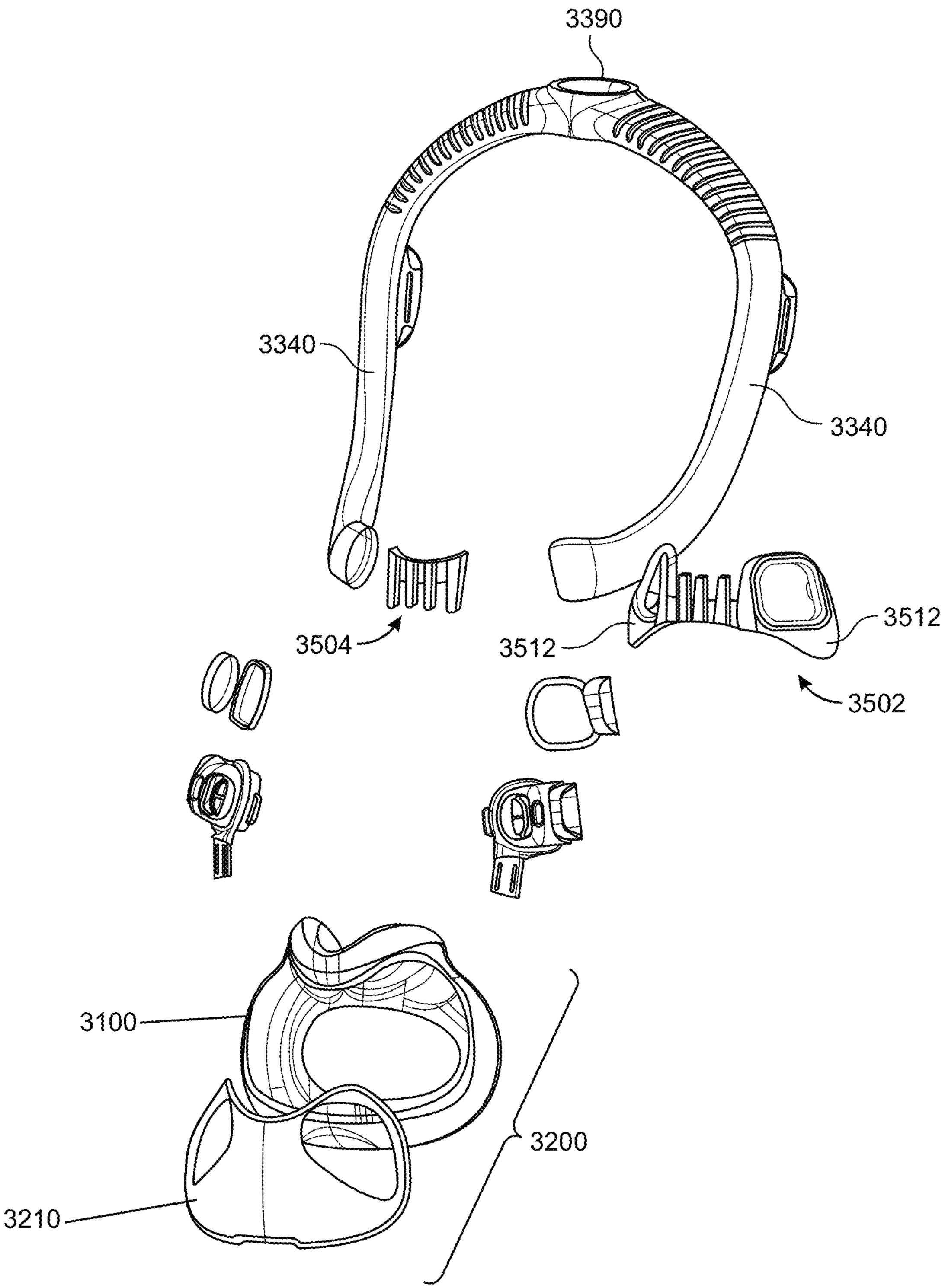
Figures 3, 14:
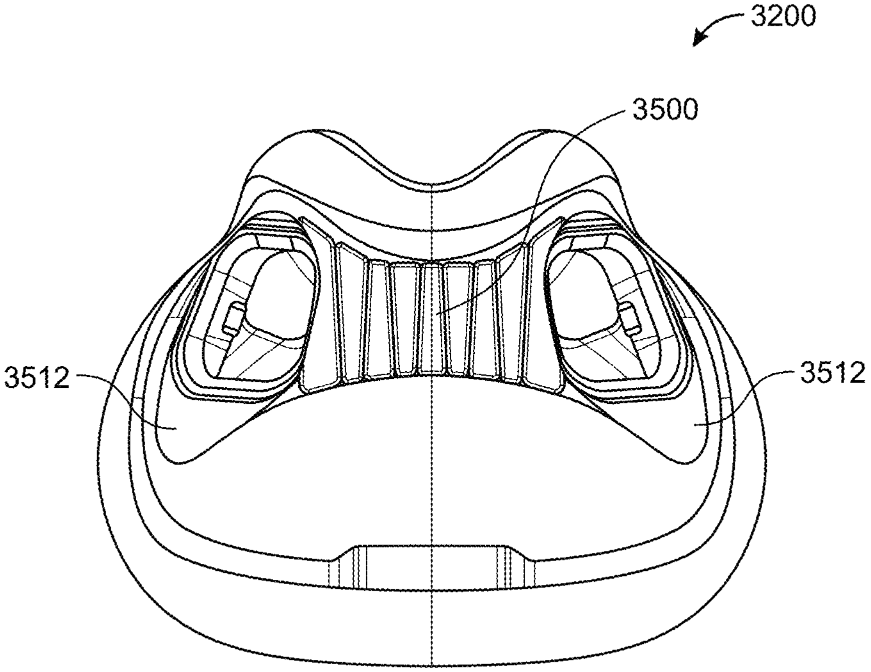
Figures 4, 14:
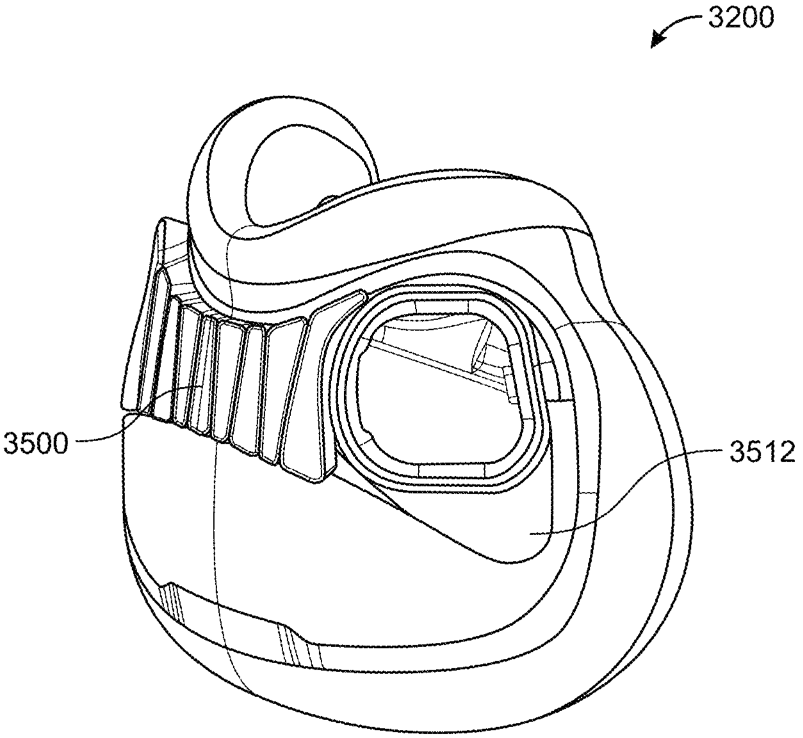
Figures 5, 14:
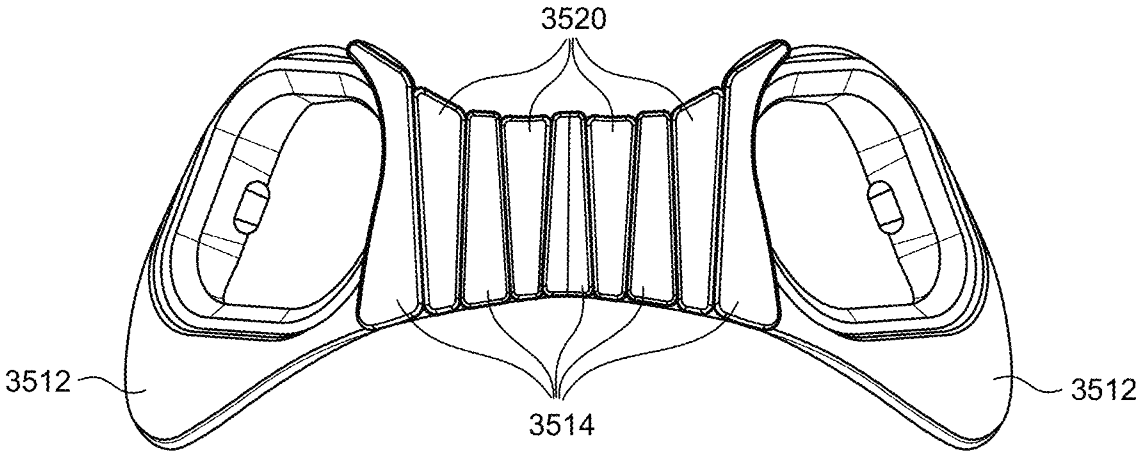
Figures 6, 14:
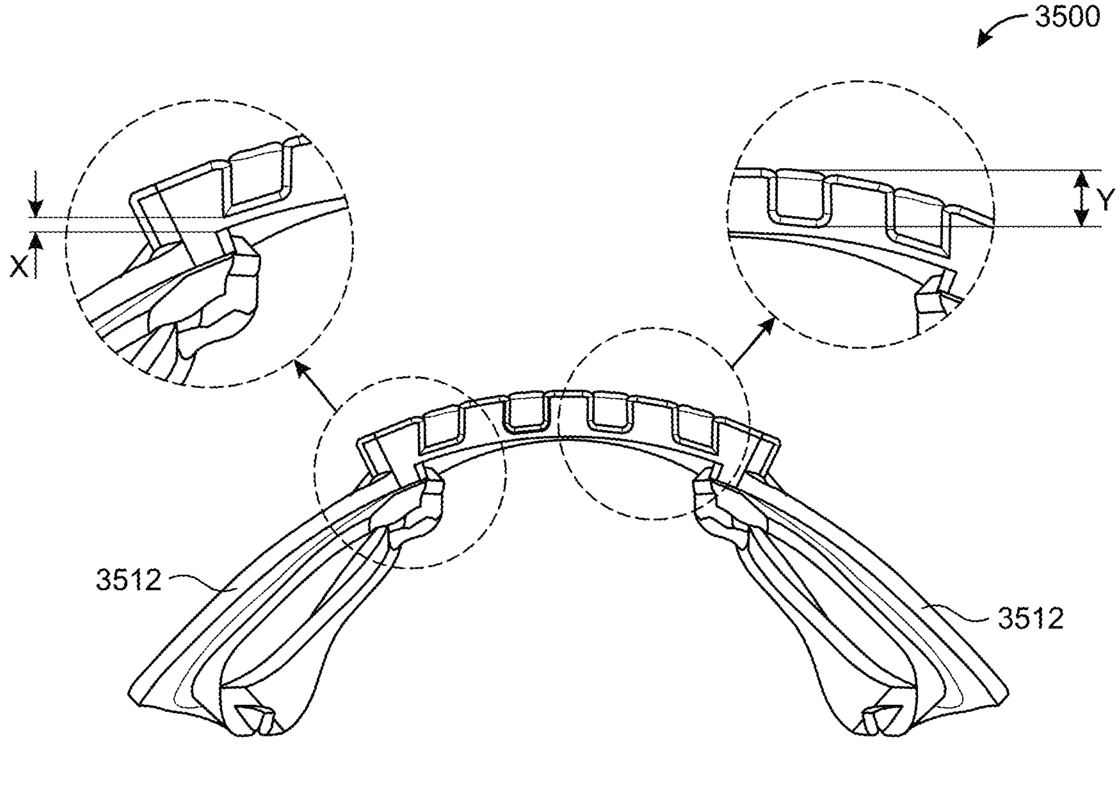
Figures 7, 14:
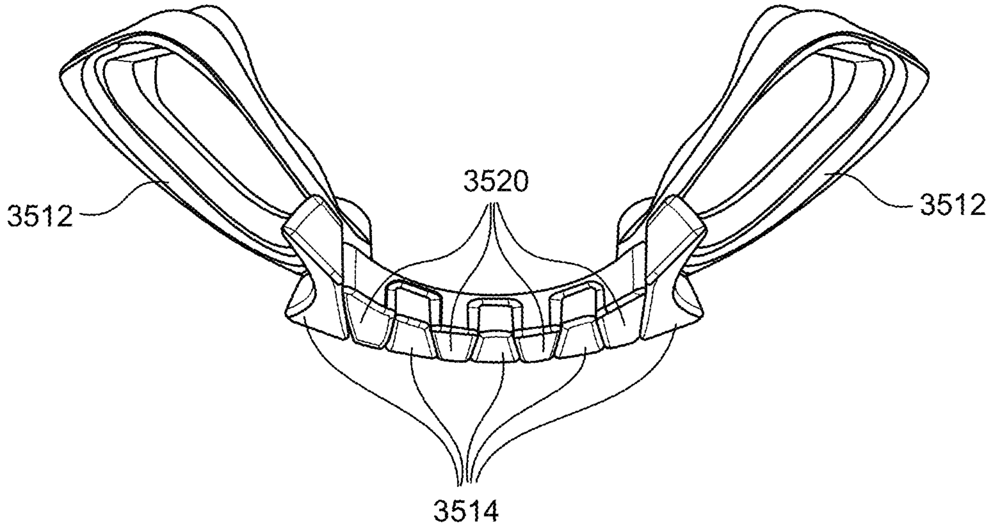
Figures 8, 14:
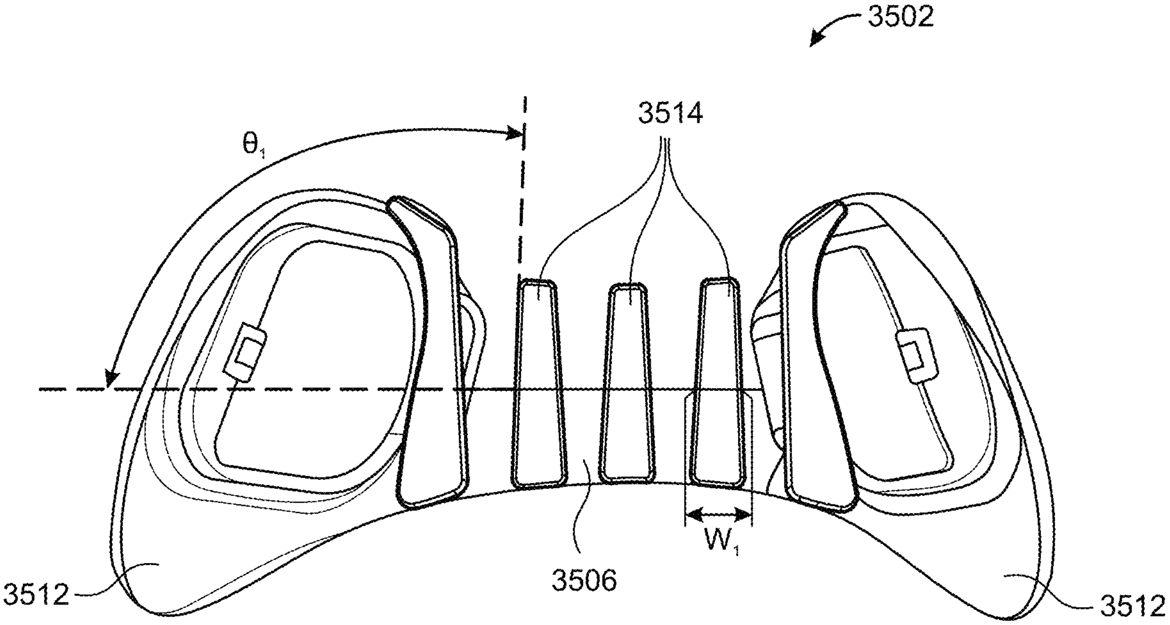
Figures 9, 14:
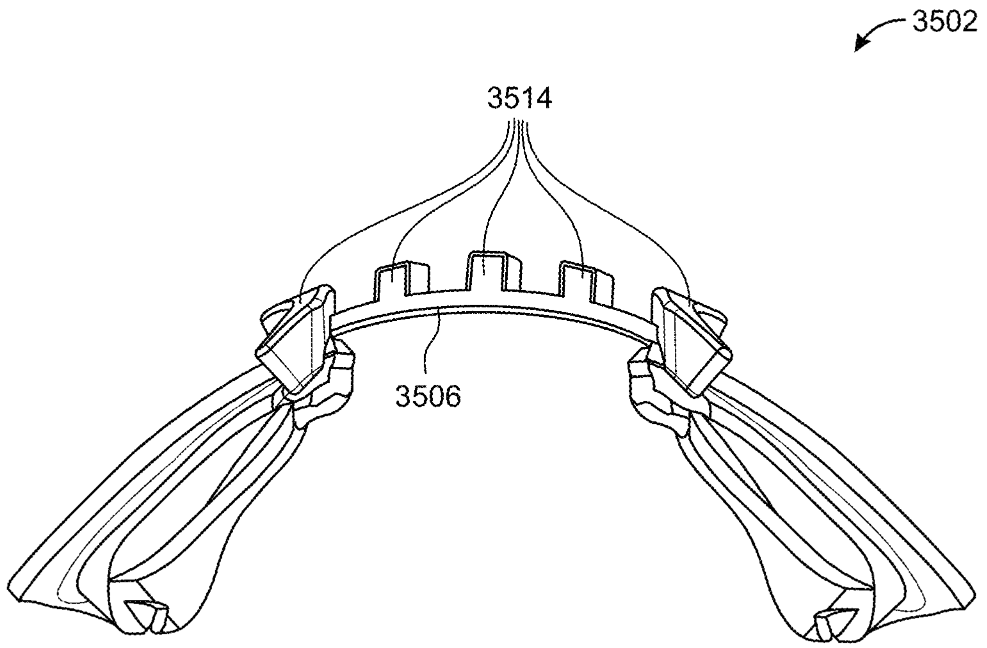
Figures 10, 14:
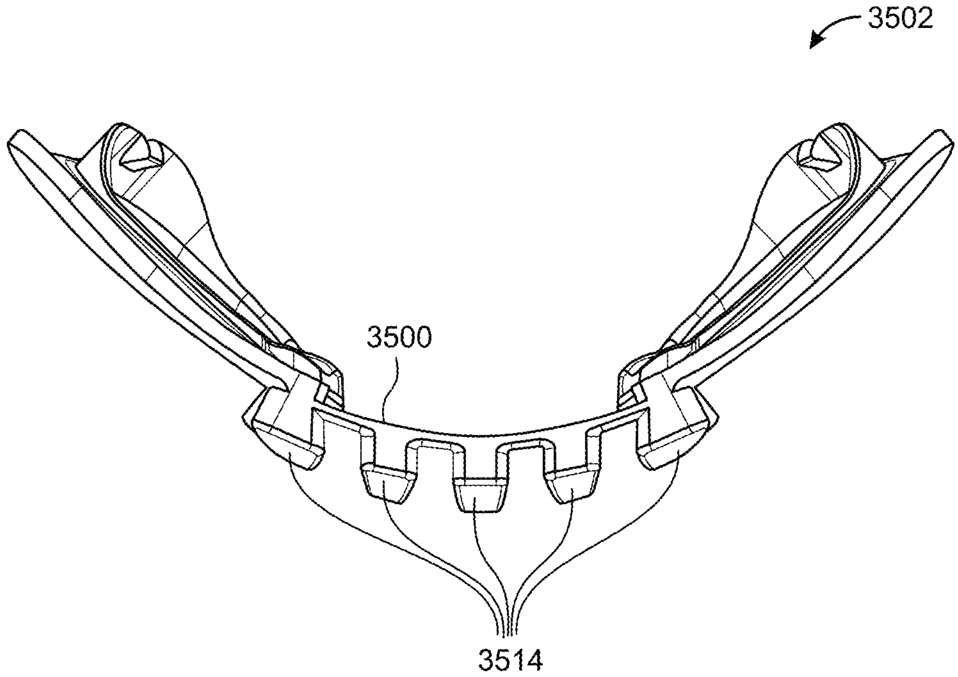
Figures 11, 14:
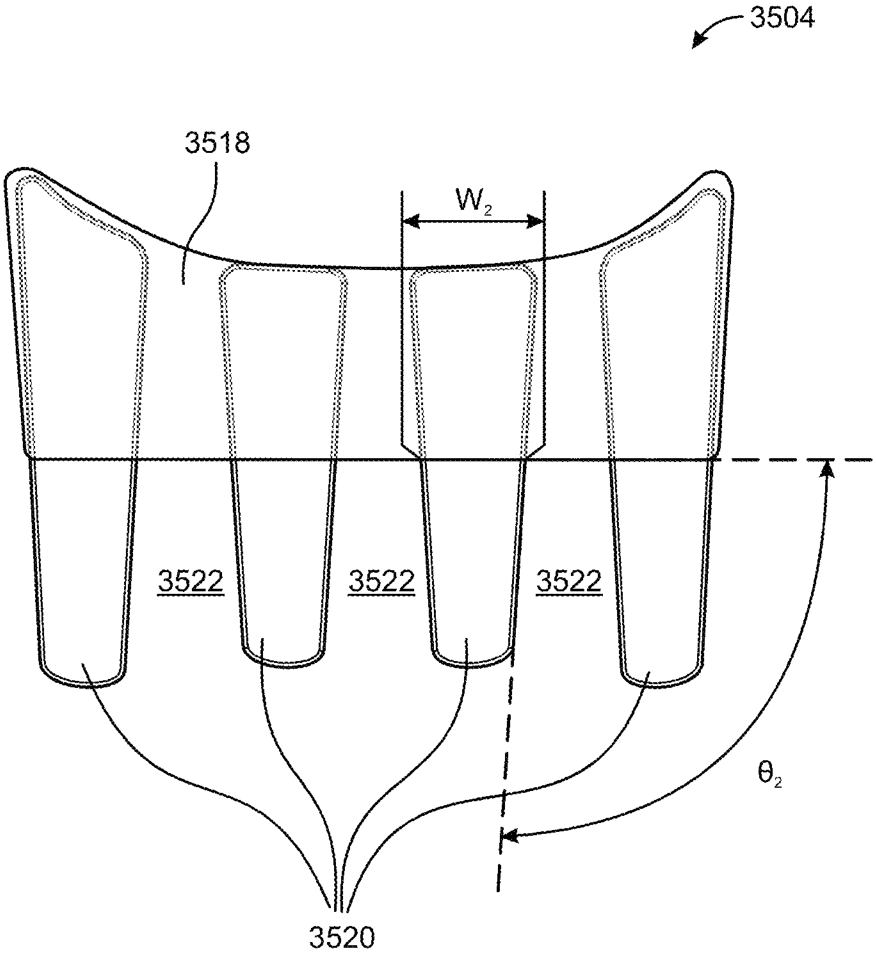

FIG. 14-1 is a front perspective view of a patient interface 3000 according to another form of the present technology.

FIG. 14-2 is an exploded view of the patient interface 3000 of FIG. 14-1.

FIG. 14-3 is a front view of a plenum chamber 3200 in the patient interface 3000 of FIGS. 14-1 and 14-2.

FIG. 14-4 is a front perspective view of the plenum chamber 3200 of FIG. 14-1.

FIG. 14.5 is a front view of a rigidiser 3500 in the plenum chamber 3200 of FIGS. 14-3 and 14-4.

FIG. 14-6 is a bottom view of the rigidiser of FIG. 14.5.

FIG. 14-7 is a top view of the rigidiser 3500 of FIGS. 14-5 and 14-6.

FIG. 14-8 is a front view of a chassis 3502 in the rigidiser 3500 of FIGS. 14-5 to 14-7.

FIG. 14-9 is a bottom view of the chassis 3502 of FIG. 14-8.

FIG. 14-10 is a top view of the chassis 3502 of FIGS. 14-8 and 14-9.

FIG. 14-11 is a front view of an insert 3504 in the rigidiser 3500 of FIGS. 14-5 to 14-7.

Figures 1, 15:
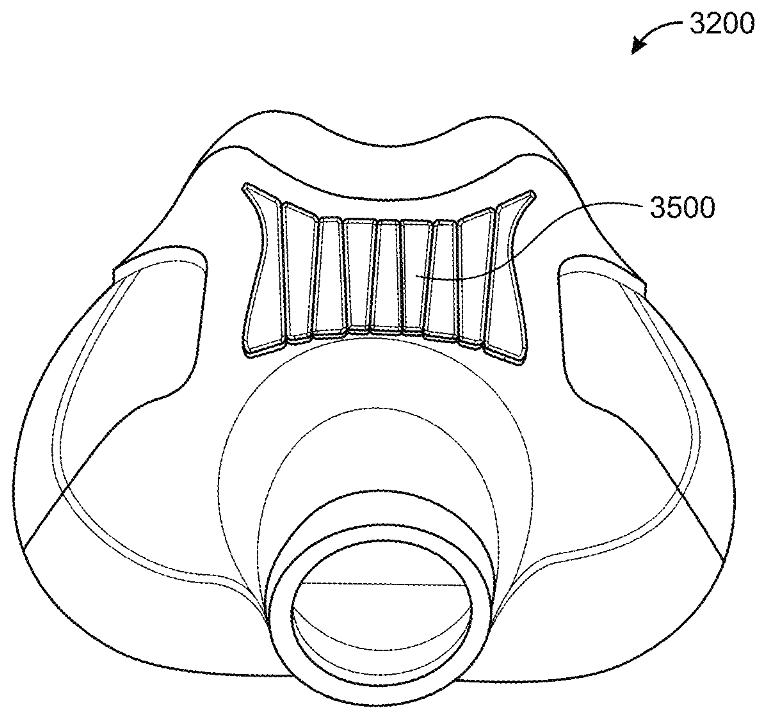
Figures 2, 15:
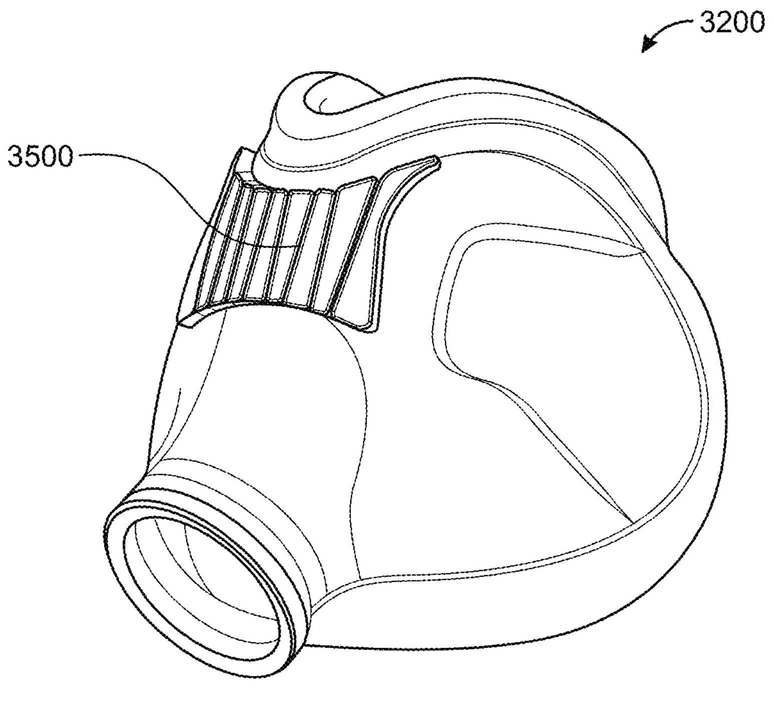
Figures 3, 15:
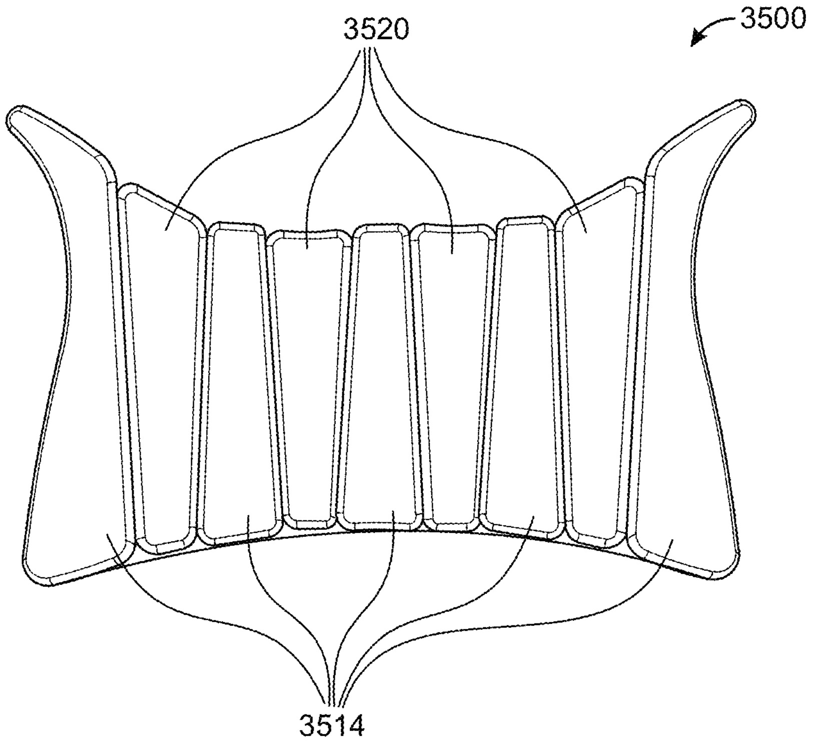
Figures 4, 15:
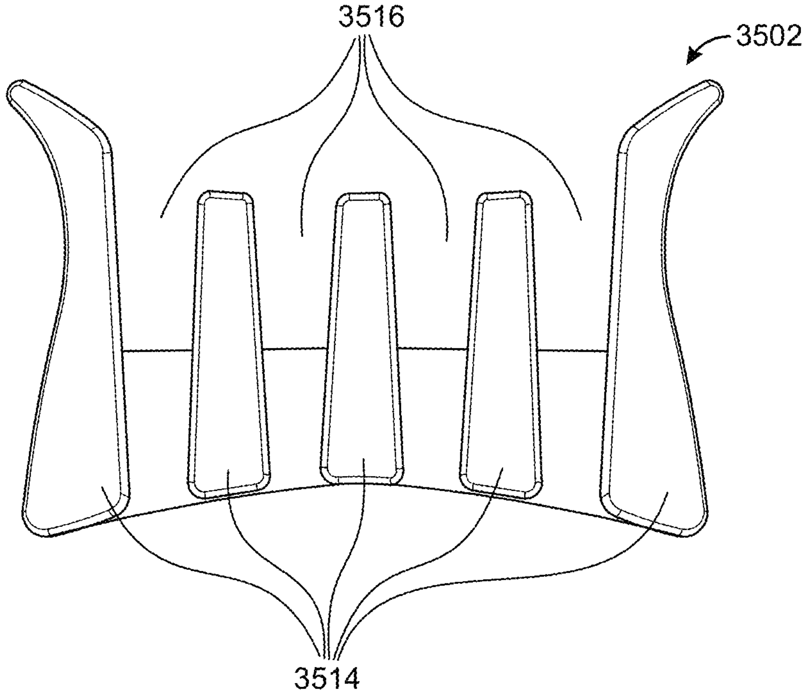
Figures 5, 15:
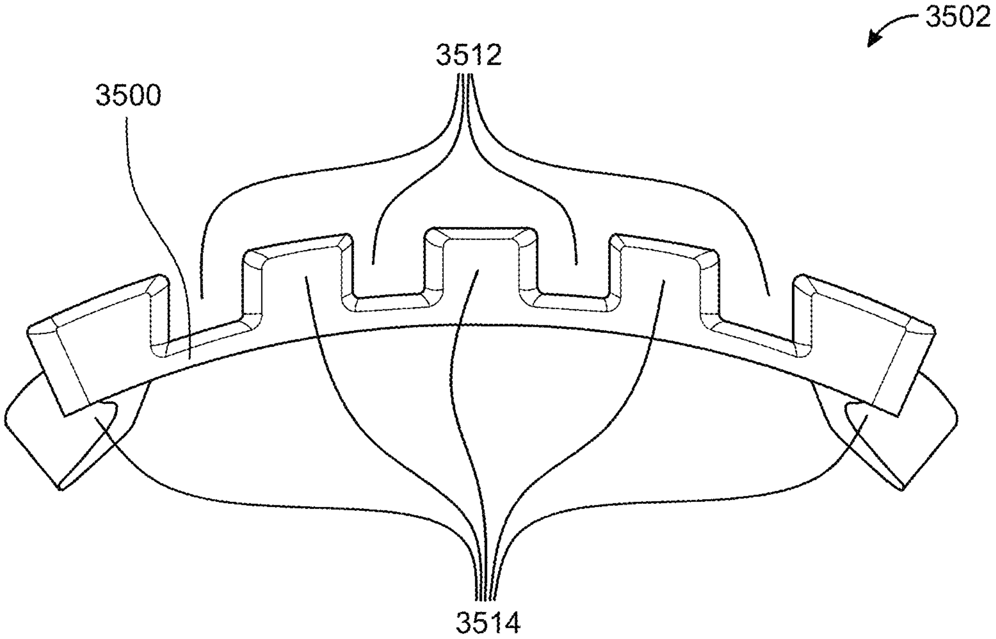
Figures 6, 15:
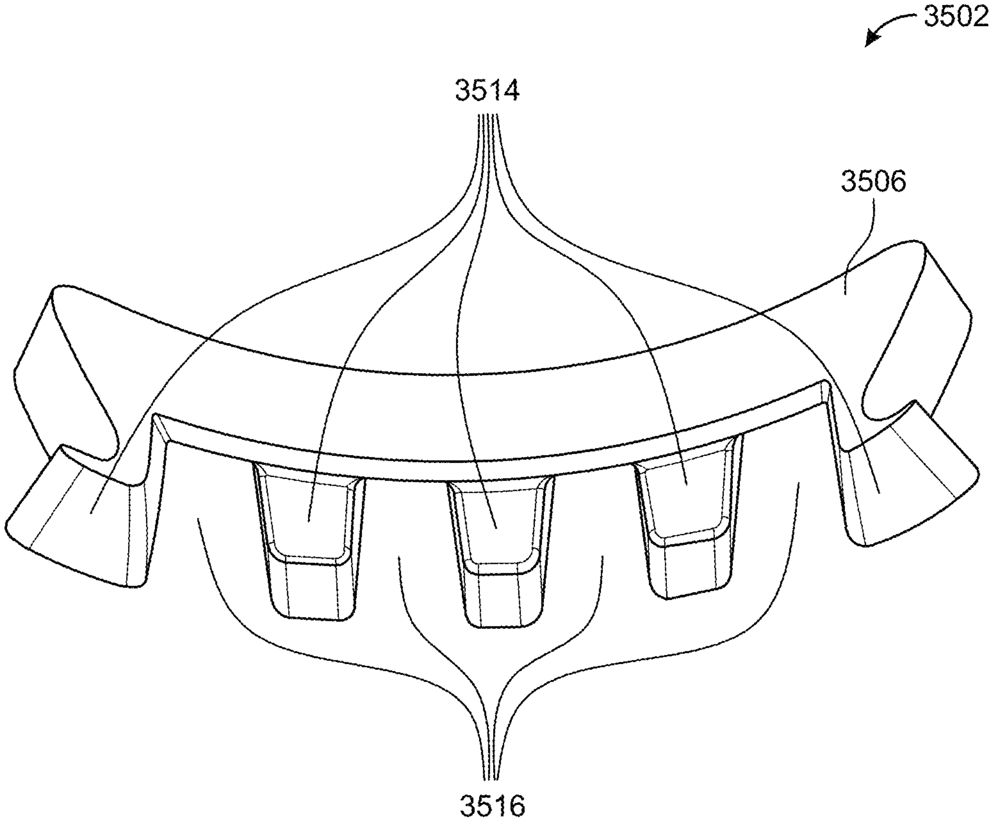
Figures 7, 15:
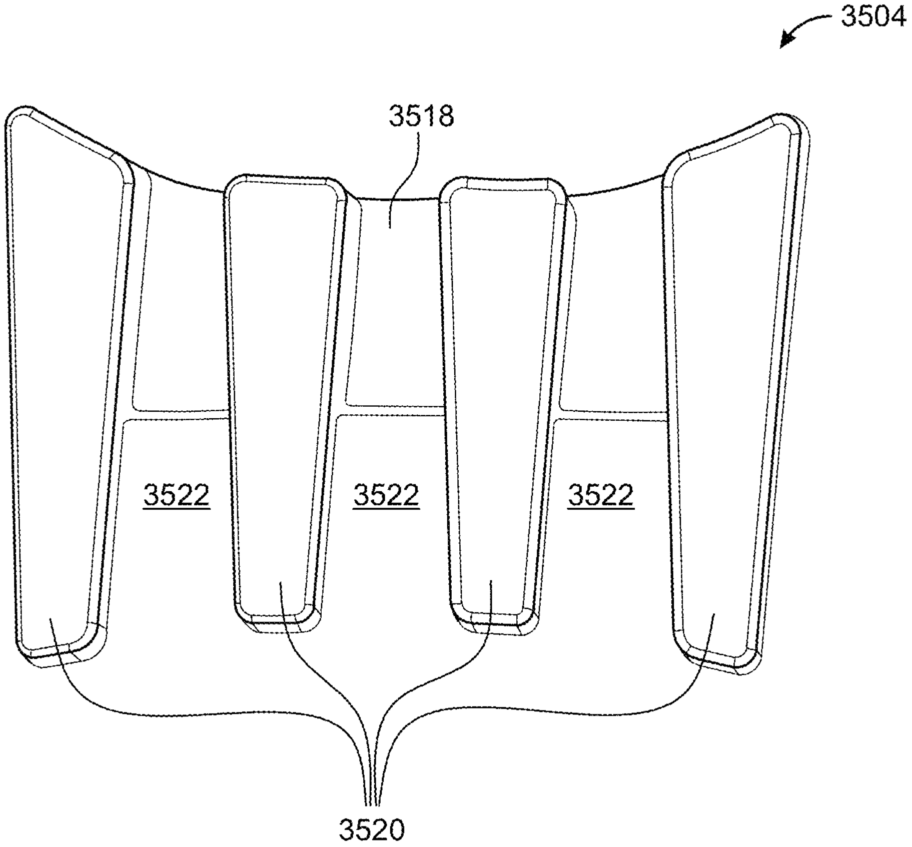
Figures 8, 15:
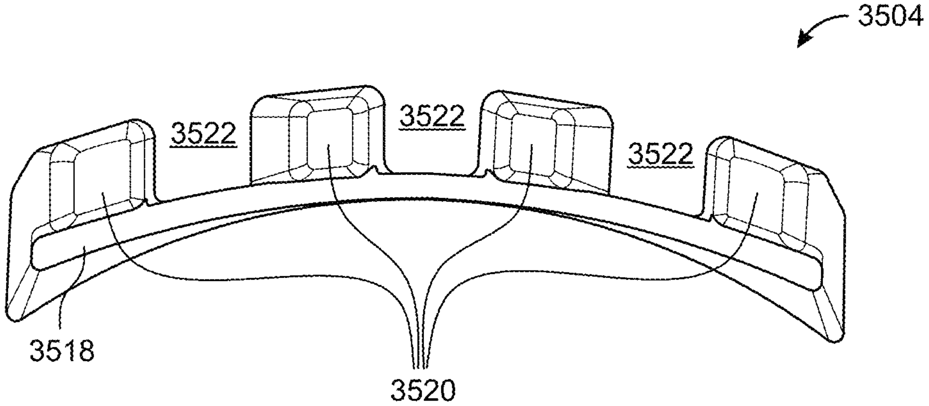
Figures 9, 15:
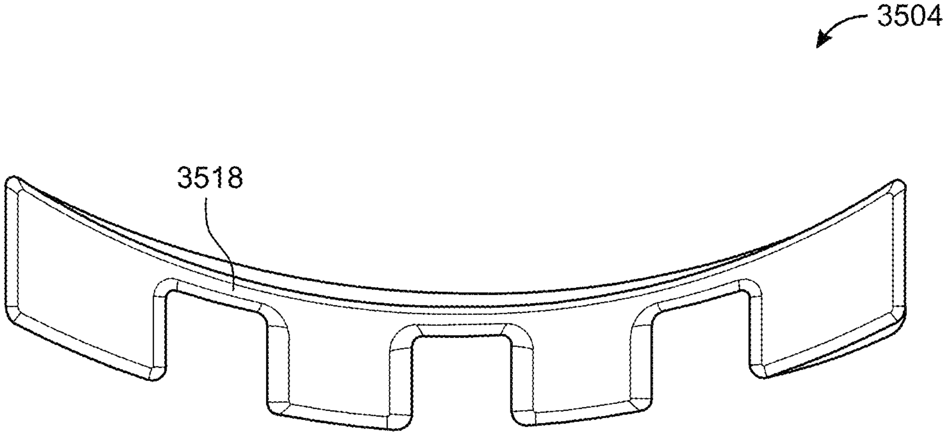

FIG. 15-1 is a front view of a plenum chamber 3200 in accordance with another form of the present technology.

FIG. 15-2 is a front perspective view of the plenum chamber 3200 of FIG. 15-1.

FIG. 15-3 is a front view of a rigidiser 3500 in the plenum chamber of FIGS. 15-1 and 15-2.

FIG. 15-4 is a front view of a chassis 3502 of the rigidiser 3500 of FIG. 15-3.

FIG. 15-5 is a bottom view of the chassis 3502 of FIG. 15.4.

FIG. 15-6 is a top view of the chassis 3502 of FIGS. 15-4 and 15-5.

FIG. 15-7 is a front view of an insert 3504 in the rigidiser 3500 of FIG. 15-3.

FIG. 15-8 is a bottom view of the insert 3504 of FIG. 15-7.

FIG. 15-9 is a top view of the insert 3504 of FIGS. 15.7 and 15-8.

4.8 Second Embodiment of a Patient Interface of the Present Technology

Figure 16:
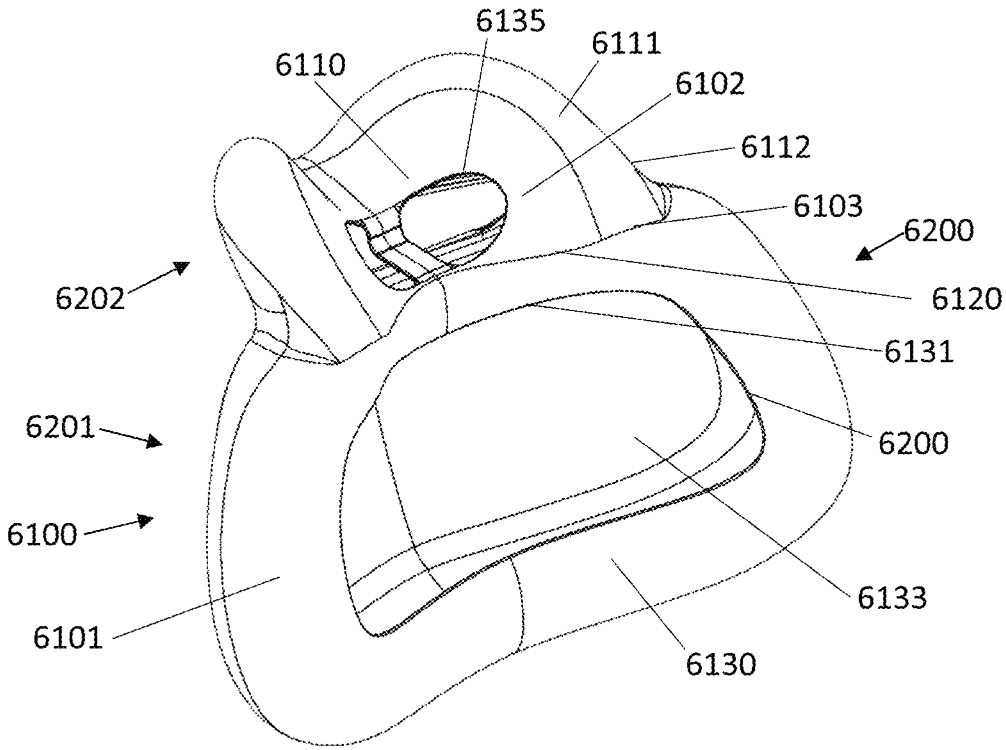

FIG. 16 is a rear perspective view of a plenum chamber in accordance with one form of the present technology, with inlet ports not shown.

Figure 17:
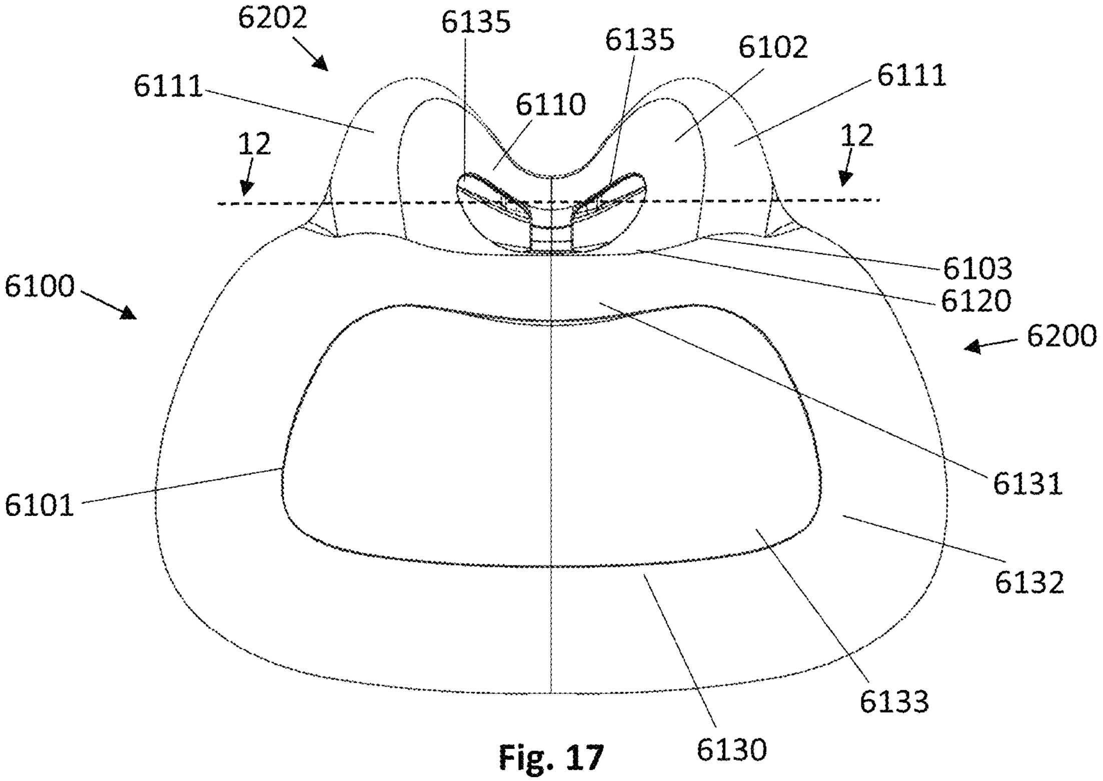

FIG. 17 is a rear view of the plenum chamber of FIG. 16.

Figure 18:
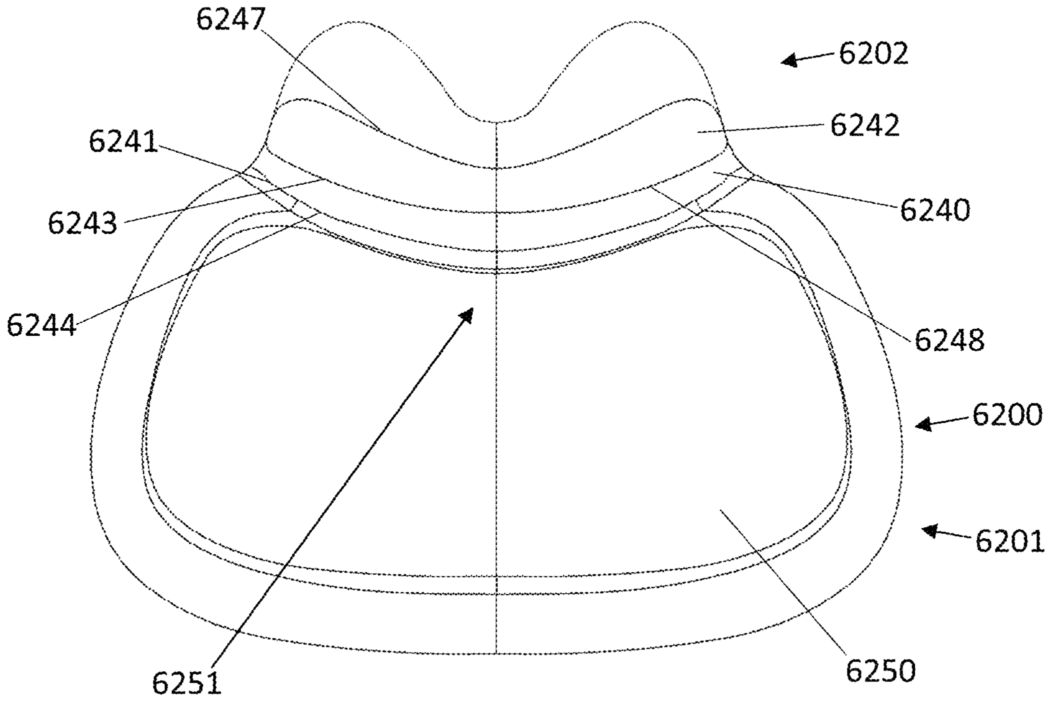

FIG. 18 is a front view of the plenum chamber of FIG. 16.

Figure 19:
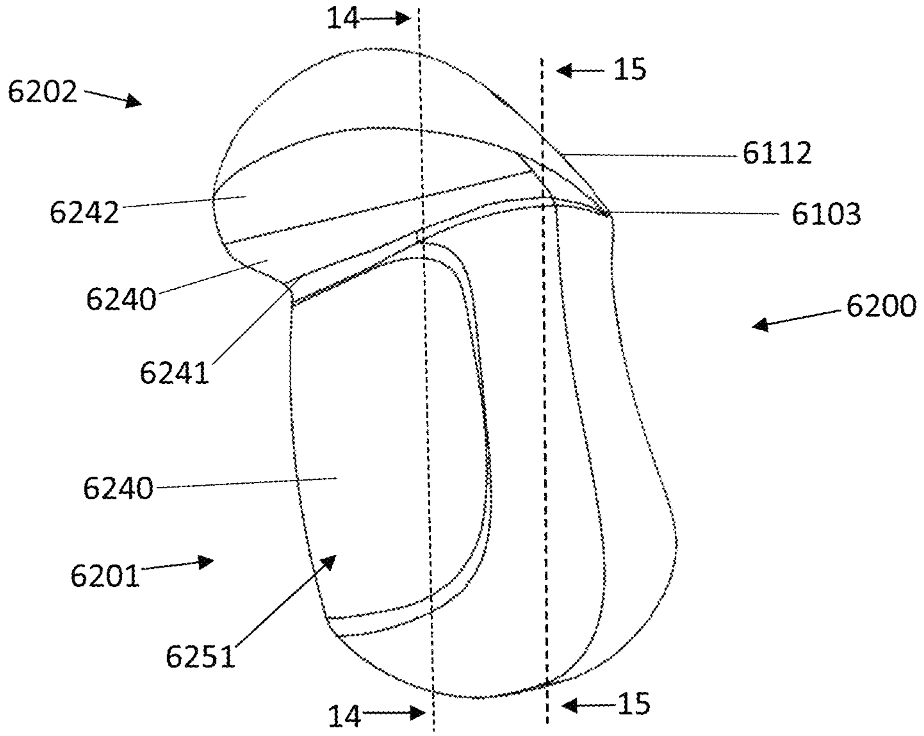

FIG. 19 is a side view of the plenum chamber of FIG. 16.

Figure 20:
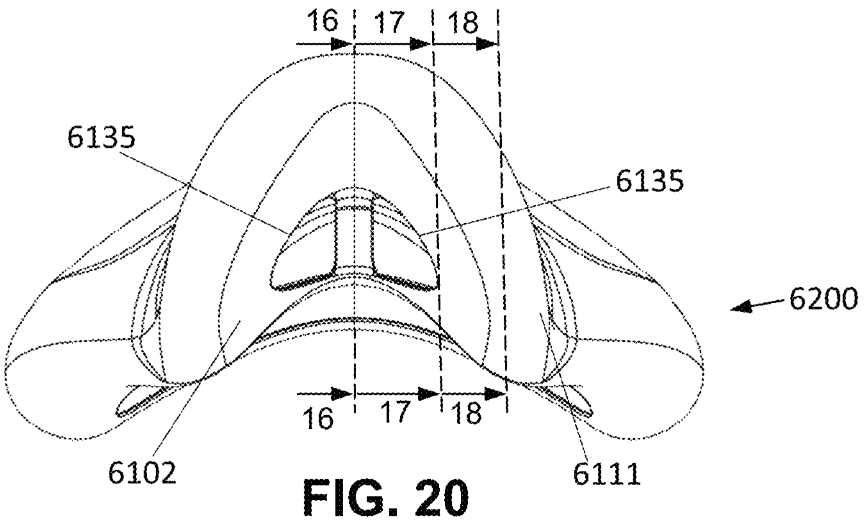

FIG. 20 is a top view of the plenum chamber of FIG. 16.

Figure 21:
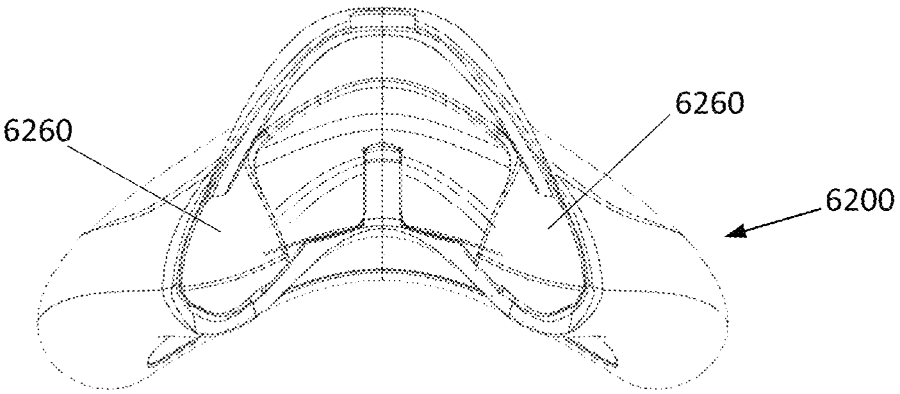

FIG. 21 is a cross-section of the plenum chamber through plane 12-12.

Figure 22:
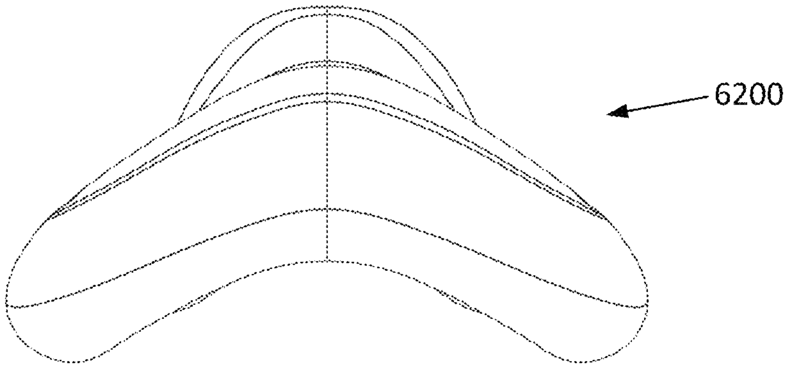

FIG. 22 is a bottom view of the plenum chamber of FIG. 16.

Figure 23:
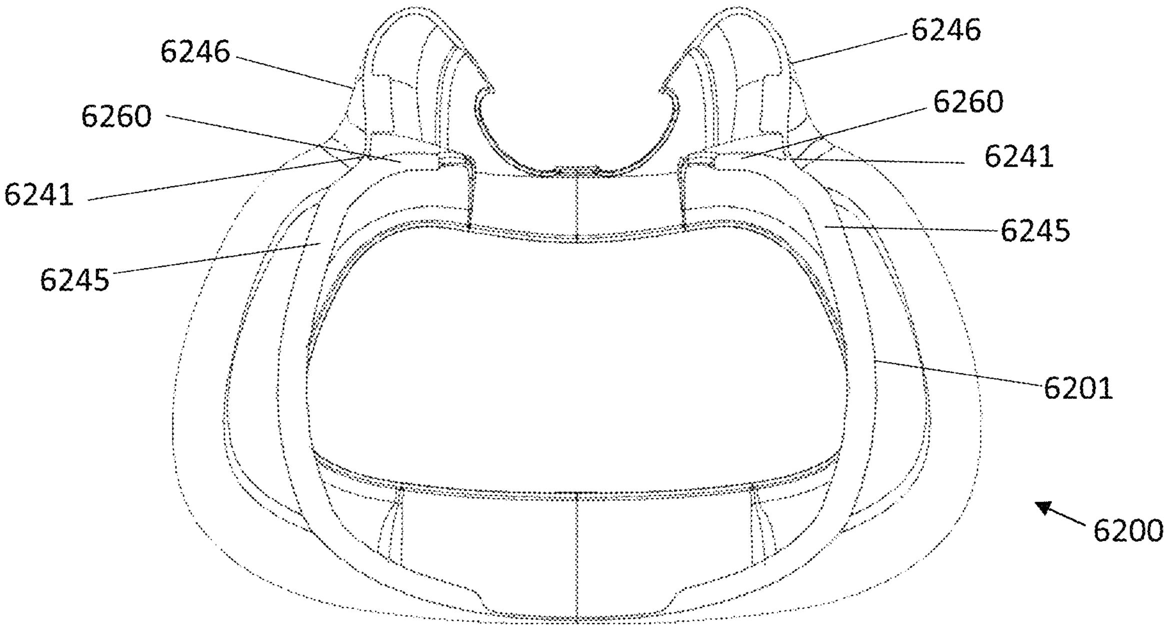

FIG. 23 is a cross-section of the plenum chamber through plane 14-14.

Figure 24:
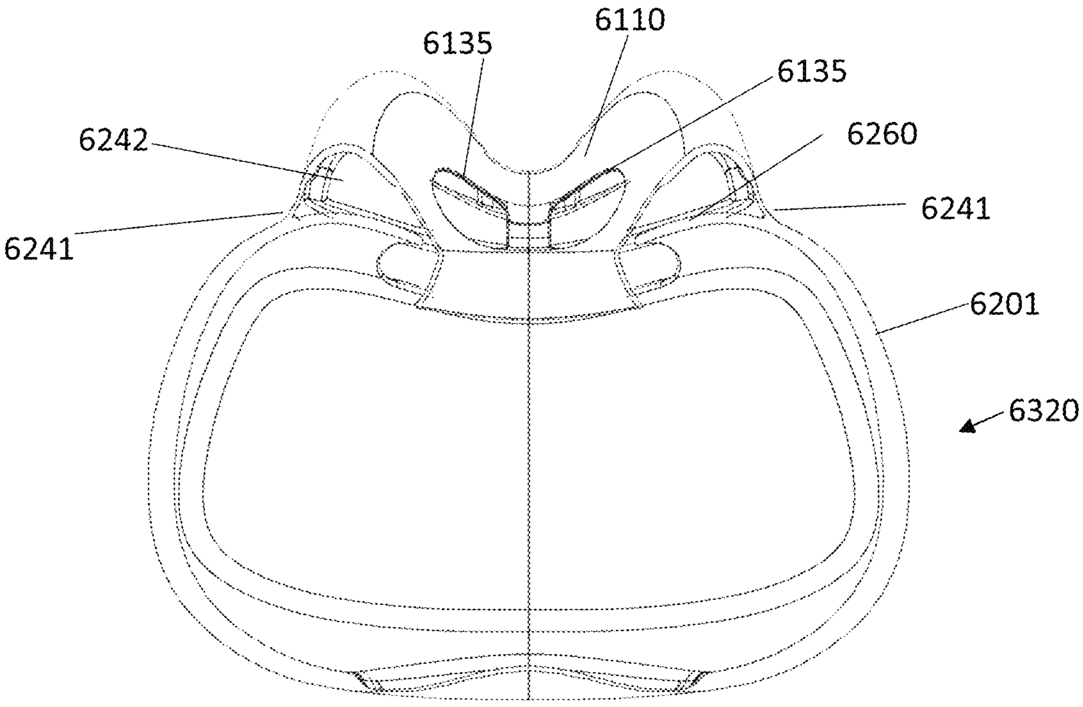

FIG. 24 is a cross-section of the plenum chamber through plane 15-15.

Figure 25:
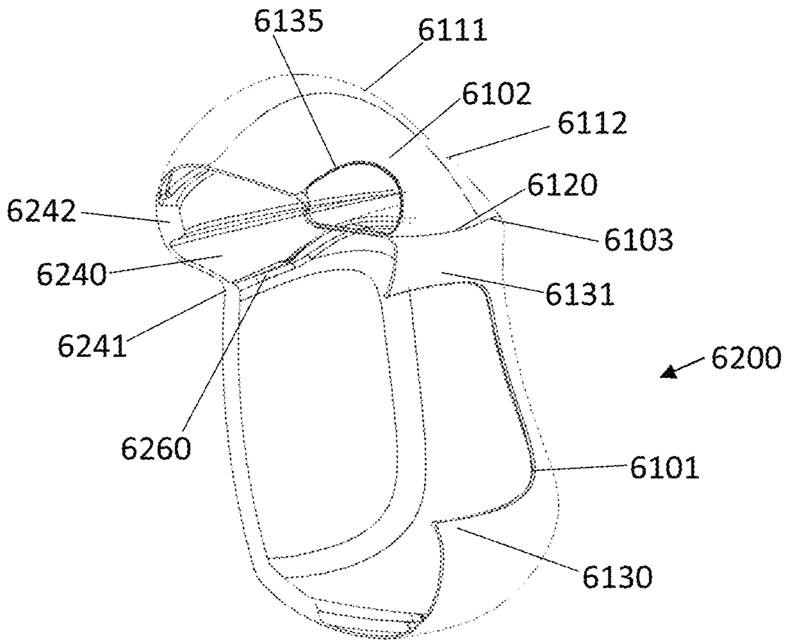

FIG. 25 is a cross-section of the plenum chamber through plane 16-16.

Figure 26:
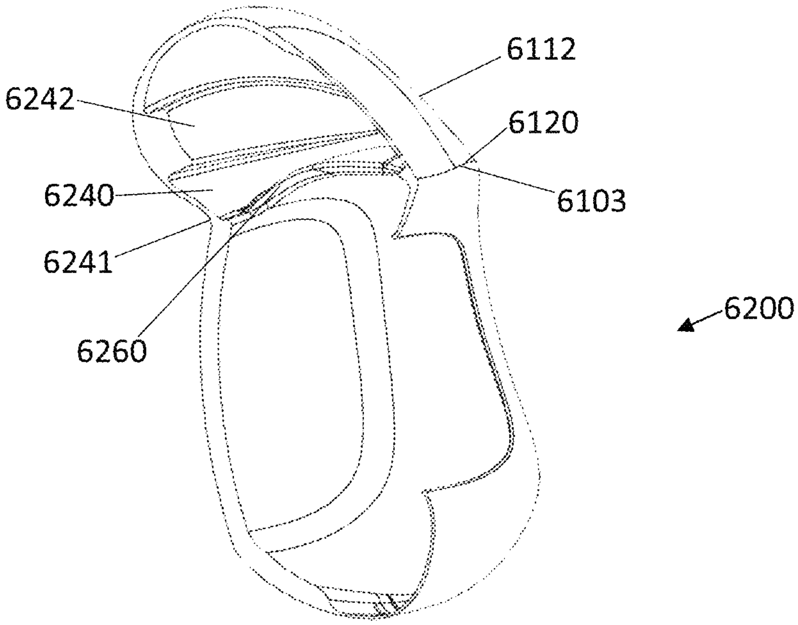

FIG. 26 is a cross-section of the plenum chamber through plane 17-17.

Figure 27:
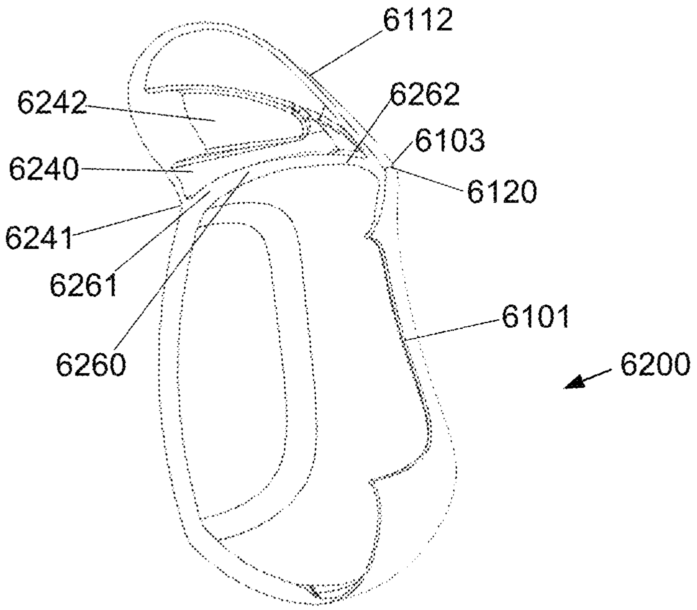

FIG. 27 is a cross-section of the plenum chamber through plane 18-18.

Figure 28:
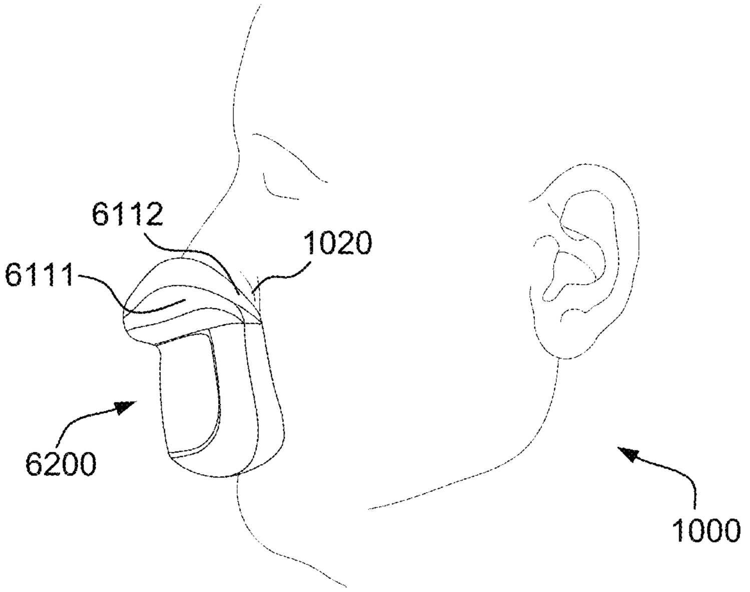

FIG. 28 shows a side view of the plenum chamber in an in-use position on a patient's face, with the plenum chamber shown in outline for clarity.

Figure 29:
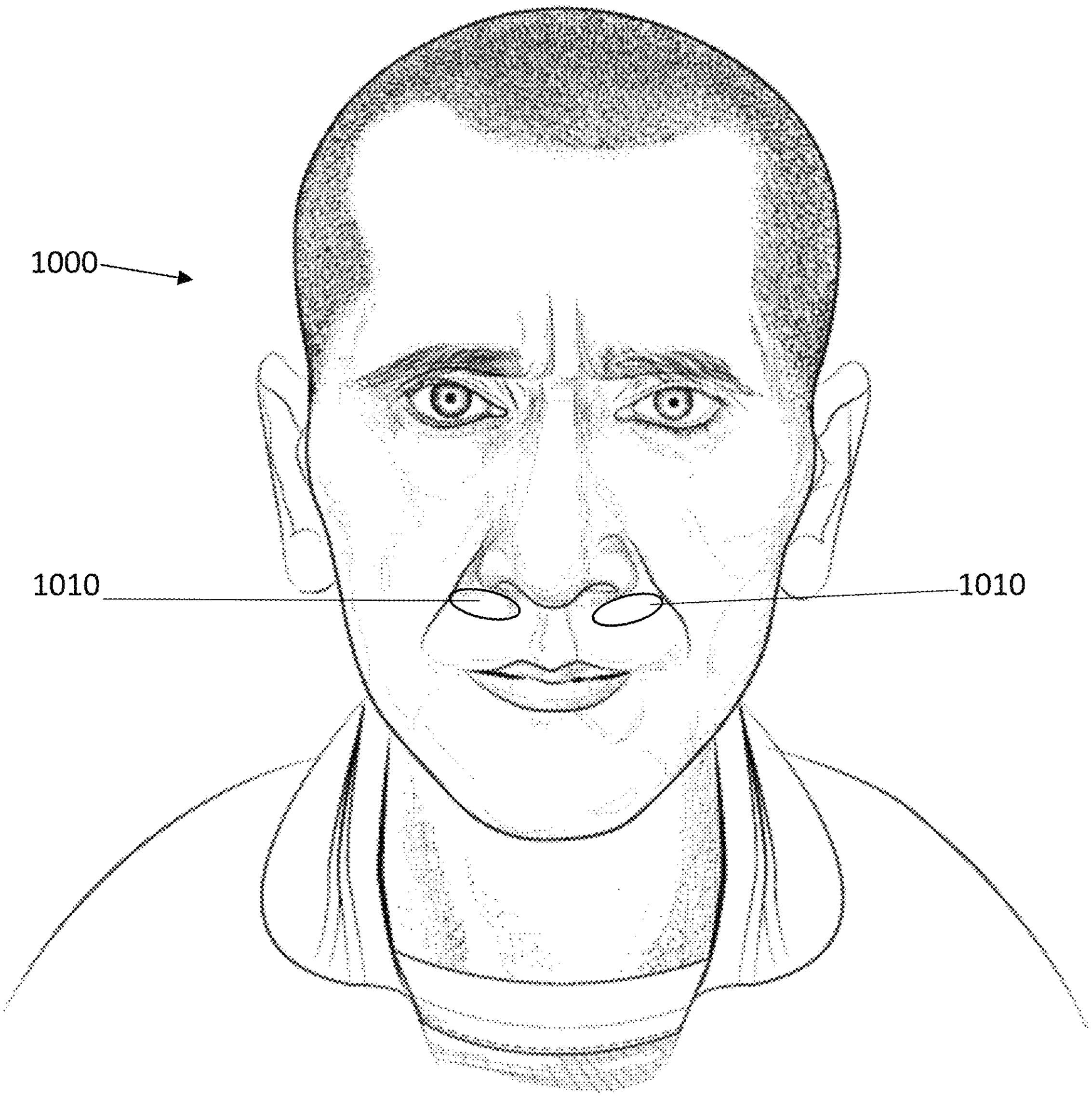

FIG. 29 shows a patient's face with particular areas of engagement by a seal forming structure indicated.

Figure 30:
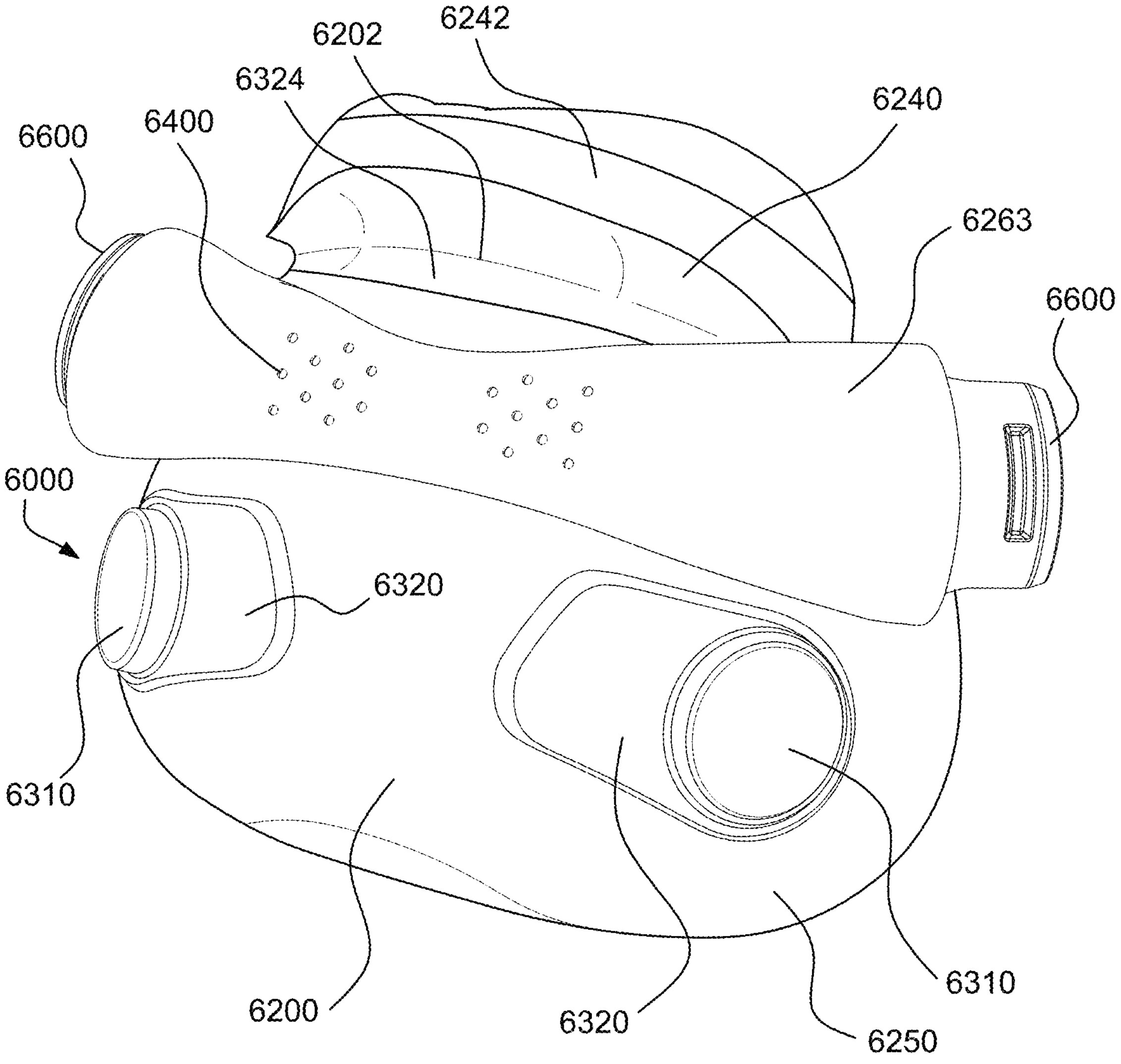

FIG. 30 is a front perspective view of a patient interface in accordance with another form of the technology.

Figure 31:
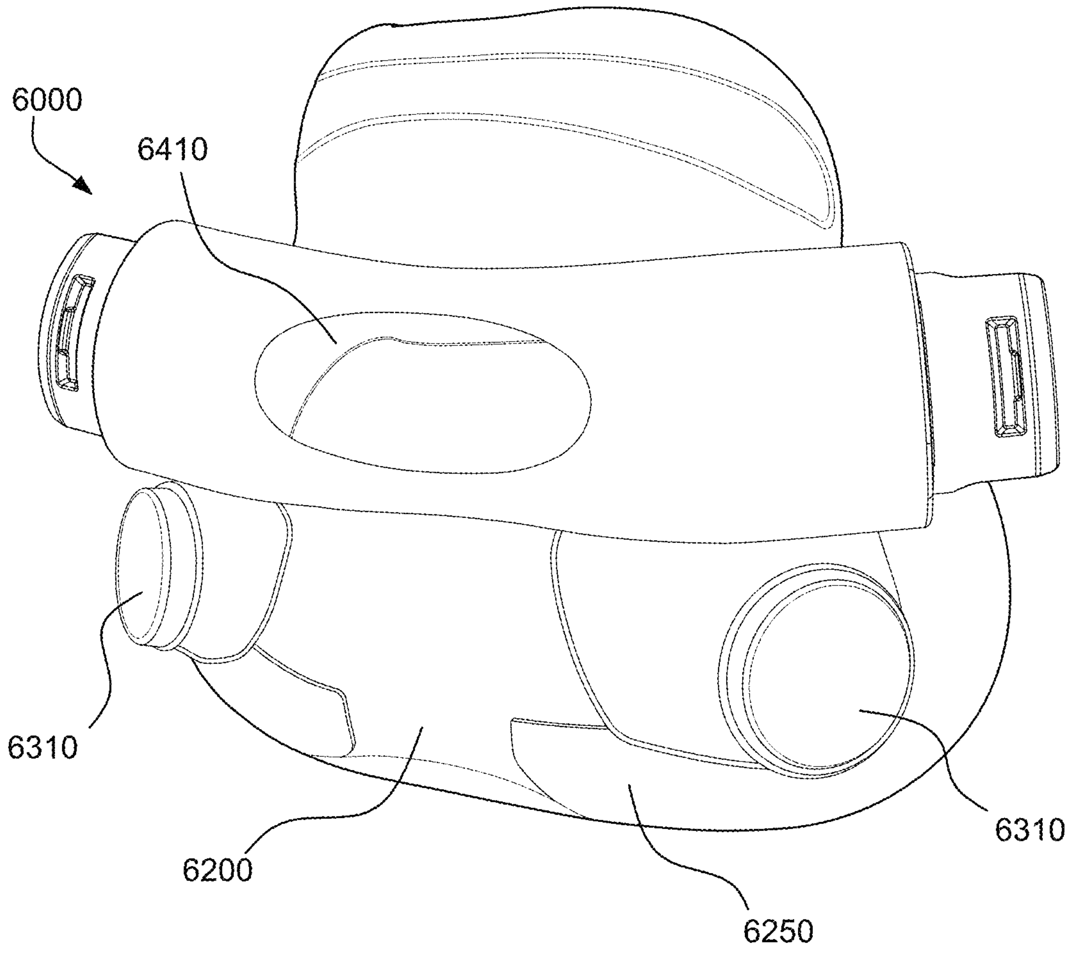

FIG. 31 is a front perspective view of a patient interface in accordance with yet another form of the technology, with a vent removed.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

Where anatomical directional terms are used in describing aspects and examples of the present technology, such as "anterior", "posterior", "superior", "inferior", "lateral", "medial" and the like, the directions are to be applied in the context of the present technology during use by a patient. For example, an anterior side of a patient interface refers to the side of the patient interface which is anterior with respect to the patient when the patient has donned the patient interface in the intended manner.

Where surfaces or portions are described as facing a direction, e.g. "superior-facing", "anterior-facing" and the like, unless the context clearly requires otherwise the surfaces or portions are to be understood as at least partially facing in the particular direction. A portion may be "superior-facing" if the portion generally faces a superior direction, even if it partially also faces another direction.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 First Embodiment of a Patient Interface

A non-invasive patient interface 3000 in accordance with one aspect of the present technology comprises the following functional aspects: a plenum chamber 3200 comprising a seal-forming structure 3100, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

In some examples of the present technology, the plenum chamber 3200 is at least partially formed by a fascia portion 3210 (referred to as a shell in some examples) and the seal-forming structure 3100. The plenum chamber 3200 may comprise a cushion module or cushion assembly, for example. The fascia portion 3210 may function as a chassis for the seal-forming structure 3100.

The patient interface 3000 in some examples of the technology is an oronasal patient interface. That is, the patient interface 3000 is configured to seal around both the patient's nasal airways and oral airway. In some examples the patient interface 3000 comprises separate seals around each of the nasal airways and oral airway. The patient interface 3000 may comprise a plenum chamber 3200 having a nasal portion 3230 and an oral portion 3260, as shown in FIGS. 7-1 to 8-5, 10 to 11-5 and 13-1 to 13-3, for example. The seal forming structure may be configured to surround the nasal airways at the nasal portion 3230 and to seal around the patient's mouth at the oral portion 3260. As such, the seal-forming structure 3100 may also be considered to have a nasal portion and an oral portion, the nasal portions and oral portions of the seal-forming structure comprising those parts that seal around the patient's nasal airways and mouth respectively.

In the examples shown in FIGS. 7-1 to 8-5, 10 to 11-5 and 13-1 to 13-3, the seal-forming structure 3100 at the nasal portion 3230 does not lie over a nose bridge region or nose ridge region of the patient's face and instead seals against inferior surfaces of the patient's nose. The nasal portion 3230 may seal against the lip superior, the ala and the anterior surface of the pronasale and/or the inferior surface of the pronasale. The actual sealing locations may differ between patients. The nasal portion 3230 may also be configured to contact and/or seal to a region of the patient's face between the ala and the nasolabial sulcus and at the lateral portions of the lip superior proximate the nasolabial sulcus.

The seal-forming structure 3100 of the oral portion 3260 may be configured to form a seal to a periphery of the patient's mouth in use. The oral portion 3260 may be configured to form a seal to the patient's face at the lip superior, nasolabial sulcus, cheeks, lip inferior, supramenton, for example.

The seal-forming structure 3100 may have one or more holes therein such that the flow of air at a therapeutic pressure is delivered to the patient's nares and to the patient's mouth via the one or more holes. The seal-forming structure may define an oral hole and one or more nasal holes to deliver the flow of air to the patient. In the examples shown in FIGS. 7-1 to 8-5, 10 to 11-5 and 13-1 to 13-3, the plenum chamber 3200 comprises a seal-forming structure 3100 comprising an oral hole 3271 and two nasal holes 3272. Each of the nasal holes 3272 may be positioned on the plenum chamber 3200 to be substantially aligned with a nare of the patient in order to deliver a flow of air thereto in use. In alternative examples, only a single hole in the nasal portion 3230 of the seal-forming structure 3100 may be provided to provide a flow of air to the patient's nasal passages.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 $cmH_2O$ with respect to ambient.

The patient interface 3000 in accordance with one form of the present technology is constructed and arranged to be able to provide a supply of air at a positive pressure of at least 10 $cmH_2O$ with respect to ambient.

The patient interface 3000 in accordance with one form of the present technology is constructed and arranged to be able to provide a supply of air at a positive pressure of at least 20 $cmH_2O$ with respect to ambient.

5.3.1 Plenum Chamber

The plenum chamber 3200 has a perimeter that is shaped to be complementary to the surface contour of the face of an average person in the region where a seal will form in use. In the examples shown in FIGS. 7-1 to 8-5, 10 to 11-5 and 13-1 to 13-3 the plenum chamber comprises a fascia portion 3210 and a seal-forming structure 3100. In these examples a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, at least a portion of the plenum chamber 3200 is constructed from a transparent material. The use of a transparent material can reduce the obtrusiveness of the patient interface, and help improve compliance with therapy. The use of a transparent material can aid a clinician to observe how the patient interface is located and functioning.

FIGS. 7-1 to 8-5, 10 to 11-5 and 13-1 to 13-3 show plenum chambers 3200 according to examples of the present technology which are formed partially by a fascia portion 3210. Additionally, the plenum chamber 3200 is formed partially by the seal-forming structure 3100. In the examples shown in FIGS. 7-1 to 8-5, 10 to 11-5 and 13-1 to 13-3 the seal-forming structure 3100 and at least a portion of fascia portion 3210 are integrally formed. In some forms, the plenum chamber 3200 (more particularly fascia portion 3210) and the seal-forming structure 3100 are formed from a single homogeneous piece of material.

In alternative examples the seal-forming structure 3100 is overmoulded to the fascia portion 3210. The seal-forming structure 3100 may alternatively be formed separately from the fascia portion 3210 and be configured to permanently or removably connect to the fascia portion 3210.

In examples, one or more reinforcing structures may be selectively provided to the plenum chamber 3200 to modify the fit and/or behaviour of the patient interface 3000. A plurality of reinforcing structures may be available for selection by the patient or a clinician, for example having different rigidities, shapes, or sizes. The reinforcing structures may be provided directly to the seal-forming structure 3100 and/or the fascia portion 3200, or may be provided to components connected thereto (for example, headgear connection supports 3302, lateral inserts 3214, or headgear connector 3246 in various examples of the present technology).

5.3.1.1 Fascia Portion of the Plenum Chamber

In the examples shown in FIGS. 7-1 to 8-5, 10-1 to 11-5, 13-1 to 13-3, 14-1 to 14-11 and 15-1 to 15-9, the seal-forming structure 3100 and the fascia portion 3210 are formed from a flexible material. In one example the flexible material is a silicone. In alternate examples the flexible material may be a thermoplastic elastomer (TPE), a suitable foam, or similar.

Generally, the fascia portion 3210 is configured to have sufficient stiffness so as to resiliently maintain the form of the seal-forming structure 3100, while still providing a degree of flexibility. In the examples shown in FIGS. 7-1 to 8-5, 10-1 to 11-5, 13-1 to 13-3, 14-1 to 14-11 and 15-1 to 15-9 at least a substantive portion of the fascia portion 3210 is stiffer than the seal-forming structure 3100.

In the examples, some portions of the fascia portion 3210 have a greater stiffness than other portions. In the example shown in FIGS. 7-1 to 8-5 and 10-1 to 10-2, the fascia portion 3210 includes first and second lateral headgear support recesses 3212 on an anterior facing side of the fascia portion 3210. The first and second lateral headgear support recesses 3212 are provided proximate to lateral portions 3145 of an oral portion 3260 of the seal-forming structure 3100 (described further below). The lateral headgear support recesses 3212 are configured to receive headgear connection supports 3302—as shown in FIG. 10-1. The headgear connection supports 3302 are made of a more rigid material (for example, polycarbonate), to provide a support structure for head gear connection points. The wall thickness of the lateral headgear support recesses 3212 may be less than adjacent portions of the fascia portion 3210, with the requisite rigidity provided in combination with the headgear connection supports 3302. The headgear connection supports 3302 may be secured in place by one or more of: overmoulding, adhesives, welding, or similar. Provision of the headgear support recesses 3212 allows for excess stiffness, bulk and/or weight of the plenum chamber 3200 to be avoided.

In the exemplary plenum chamber 3200 shown in FIG. 11-1 to 13-3 the fascia portion 3210 has first and second lateral inserts 3214. The lateral inserts 3214 are made of a more rigid material, for example: polycarbonate, or a flexible material having a durometer hardness than the remainder of the fascia portion 3210. As shown in FIGS. 12-1 and 12-2, the lateral insert 3214 has an interior rim 3215 defining a plenum chamber inlet port 3240. The example illustrated, an exterior rim 3216 of the lateral insert 3214 is formed as a flange having a plurality of locating features 3217 (e.g. in the form of windows, recesses, or protrusions). Referring to FIG. 11-5, the fascia portion 3210 has insert openings 3218 in superior and lateral positions, which receive the lateral inserts 3214. During manufacture, the lateral inserts 3214 may be inserted into a tool holding the plenum chamber 3200, and joined to the fascia portion 3210 using overmoulding over the exterior rim 3216. In embodiments in which a non-adhesive material is used (for example, a non-adhesive silicone), the locating features 3217 may assist with providing a mechanical bond. In alternative examples, an adhesive material may be used, which may negate a need to provide the locating features 3217 in order to achieve a sufficient bond.

Alternate examples are contemplated in which a substantive portion of the fascia portion 3210 is more rigid than a flexible medial portion 3219 (for example, as indicated in FIG. 11-1) maintained in a superior-inferior direction. For example, the fascia inserts of the exemplary plenum chamber 3200 shown in FIG. 11-1 to 13-3 may be sized and shaped to occupy a substantive portion of the fascia portion 3210. In alternate embodiments, portions of the fascia portion 3210 may be made of a flexible material, but have a greater stiffness than the medial portion. Such differences in stiffness may be provided by one or more of: wall thickness; stiffer material (e.g. the same material with a different durometer hardness), and a reinforcing structure (e.g. a tie or a rib, an undercushion, portion or a chassis, or the like) across various examples of the present technology.

Plenum Chamber with Rigidiser

Referring now to FIGS. 14-1 to 14-11 which show an embodiment of a patient interface 3000 having an alternate plenum chamber 3200 according to an embodiment of the technology. In the embodiment of FIGS. 14-1 to 14-11, the medial portion 3219 is configured to provide a degree of control for the flex provided by the medial region of the fascia portion 3210. For instance, a rigidiser 3500 is provided in the fascia portion 3210.

As is shown in 14-2, the plenum chamber 3200 is formed as a two-part structure comprising the fascia portion 3210 and the seal forming structure 3100. In this embodiment, the fascia portion 3210 and the seal forming structure 3100 are made entirely from flexible materials and as separate components. However, the fascia portion 3210 and the seal forming structure 3100 could be made as a single component. In addition, the fascia portion and the seal forming structure 31000 may be made from more than one materials, at least one of which is relatively rigid to provide additional support and structure to the plenum chamber 3200.

The rigidiser component 3500 is structured and/or arranged to facilitate or allow inward flexing for the medial portion 3219 about at least one axis e.g. an axis in the inferior-superior direction (a vertical axis) and an inclined anterior-posterior axis. In a neutral position as shown in FIGS. 14-1 and 14-3 to 14-5, the rigidiser 3500 is shaped, e.g. curved, to generally correspond to the curve of the medial region 3210 of the plenum chamber 3200. However, the rigidiser 3500 is able to reduce or substantially limit outward bending of the medial region 3210 beyond the neutral position.

Reducing or substantially limiting outward bending can improve the sealing performance of the plenum chamber 3200, particularly in the nasal portion 3230. For instance, the rigidiser 3500 may prevent deformation of the nasal portion 3230 that can occur on an increase in the internal pressure in the plenum chamber 3200.

Referring now to FIGS. 14-6 to 14-11 which show further aspects of the rigidiser 3500. In the embodiment of FIGS. 14-6 to 14-11, the rigidiser 3500 is a two-part construction having a chassis 3502 and an insert 3504. However, the rigidiser 3500 may be formed as a single component e.g. by 3D printing techniques or moulding. The rigidiser 3500 is structured and/or arranged to provide a single layer beam when under flex in a first direction and a composite beam when flexed in a second direction. The provision of a single layer beam and a composite beam provides the rigidiser to have relatively greater flexibility in the first direction and relatively less flexibility in the second direction.

The chassis 3502 includes a bridge 3506 which spans from a first lateral side 3508 of the plenum chamber 3200 to a second lateral side 3510. The rigidiser 3500 is generally symmetrical about a medial plane of the plenum chamber 3200.

A port structure 3512 is provided at each end of the bridge 3506. For instance, each port structure 3512 may be moulded as a one-piece integral component with the bridge 3506. Alternatively, the port structure(s) 3512 may be moulded separately from the bridge 3506 and subsequently attached thereto using e.g. adhesives. In yet a further embodiment, the rigidiser 3500 may not be attached to the port structure(s) 3512 but instead provided as a separate component positioned between separate components e.g. lateral inserts 3214 described above with reference to FIGS. 11-1 to 11-6 and 12-1 to 12-2.

Each port structure 3512 is substantially equivalent to the lateral inserts 3214 as discussed above. However, the port structure(s) 3512 may have other shapes and features.

The bridge 3506 has a plurality of teeth 3514 as are perhaps best seen in FIG. 14-8. The teeth 3514 taper along their length and adjacent teeth define a tapered channel 3516. An end of each of the teeth 3514 is cantilevered from the bridge 3506.

The insert 3504 includes a body portion 3518 and a plurality of teeth 3520. The shape of the teeth 3520 is substantially similar, and preferably identical, to the shape of teeth 3514. As can be seen in FIG. 14-11, the teeth 3520 are tapered and adjacent teeth define a tapered channel 3522.

The teeth 3520 on the insert 3504 and the teeth 3514 on the chassis 3506 intermesh with each other so that channels 3522 receive teeth 3514 and channels 3516 receive teeth 3520.

The angle of the teeth 3520 with respect to the body portion is indicated by $\Theta_2$ in FIG. 14-11 and is substantially identical to angle $\Theta_1$ shown in FIG. 14-8. This facilitates the teeth 3514, 3520 intermeshing with each other and minimising or completely eliminating gaps between laterally adjacent teeth. For instance, in a neutral position as shown in FIGS. 14-1 and 14-3 to 14-5, adjacent and intermeshed teeth are touching, or only slightly separated from, each other.

The arrangement enables a slight bending of the rigidiser 3500 outwardly and away from the patient's face, about an axis in the inferior-superior direction. However, as adjacent teeth come into contact with each other during outward bending of the plenum chamber 3200, they provide a composite beam having at least two layers. The composite beam substantially limits or prevents continued outward bending about the axis. This may reduce or substantially prevent bending of the fascia portion away from the patient's face. The composite beam is indicated in FIG. 14-6 where the thickness x of the first layer is provided by the bridge 3506 and body portion 3518, while the thickness y of the second layer is provided by the teeth 3514, 3520. The thicknesses x, y of the first layer and the second layer may be adjusted to control the amount of flex in one or more of the first direction and the second direction. For instance, the thickness of the teeth 3514, 3520 may be increased to provide relatively increased rigidity and resistance to flexing in the second direction. Alternatively, the thickness of the bridge 3506 and the body portion 3518 may be increased to provide relatively increased rigidity and therefore increase resistance to flexing in the first direction.

In addition, each one of the teeth 3514, 3520 has an effective width, indicated as $W_1$ and $W_2$ in FIGS. 14-8 and 14-11 respectively. The effective width $W_1$ and $W_2$ are identical to each other. This facilitates the teeth 3514, 3520 having identical stiffnesses to each other so that the chassis 3502 and the insert 3504 have substantially identical bending stiffnesses. This may be beneficial to providing a rigidiser 3500 with predictable or consistent control of flexing in the second direction. However, it is also envisaged that one or more of the teeth 3514, 3520, may have a different size or shape, or be made from a different material, to one or more of the other teeth to provide a desired amount of flex for the rigidiser 3500 in the second direction e.g. away from the patient's face.

The bridge 3506 and the body portion 3518 are structured to allow the rigidiser to bend towards a patient's face. However, as the bridge 3506 and the body portion 3518 flex towards the patient's face adjacent teeth 3514, 3520 separate from touch each other, allowing the bridge 3506 and the body portion 3518 to flex according to the material properties and structure of bridge 3506 and body portion 3518. Therefore, the rigidiser 3500 allows the plenum chamber 3200 to flex inwardly to the patient's face and can provide a desired amount of resistance to flexing towards the patient's face.

In the embodiment of FIG. 14-1 to 14-11, at least one of the bridge 3506 and the body portion 3518 has a curved shape. The curved shape may allow the rigidiser 3500 to better conform to the shape of the patient's face. In addition, the curved shape may enable provision of a lower profile mask while still having a beneficial range of flex in the fascia portion.

5.3.1.2 Alternate Plenum Chamber with Rigidiser

Referring no to FIGS. 15-1 to 15-9 which show an alternate embodiment of a plenum chamber 3200 having a rigidiser 3500. The plenum chamber 3200 is similar to the plenum chamber 3200 of FIGS. 7-1 to 7-6 and 8-1 to 8-5. However, a rigidiser 3500 is provided in the anterior portion of the plenum chamber 3200, located generally symmetrically about a medial plane of the plenum chamber 3200.

The rigidiser 3500 is substantially identical to rigidiser 3500 described above with reference to FIGS. 14-1 to 14-11. Therefore, like references refer to like components. However, the rigidiser 3500 of FIGS. 15-1 to 15-9 does not include port structure(s) 3512.

5.3.1.3 Plenum Chamber Inlet Port

The fascia portion 3210 may comprise one or more plenum chamber inlet ports 3240. The one or more plenum chamber inlet ports 3240 may allow for a connection to other components, such as a decoupling structure, vent arrangement, heat and moisture exchanger (HMX), constant-flow vent (CFV), anti-asphyxia valve (AAV) and/or connection to a conduit in various examples.

In the example shown in FIGS. 7-1 to 8-5 and 10-1 and 10-2, the plenum chamber 3200 comprises a single inlet port 3240. The fascia portion 3210 includes an integrally formed hollow protrusion 3250 extending from a medial and inferior position on the fascia portion 3210. The hollow protrusion 3250 extends in an inferior-anterior direction, disposed more in the inferior direction than the anterior direction. A free end of the hollow protrusion 3250 terminates in a rim 3252 surrounding the inlet port 3240. A connection port ridge 3608 is provided on the interior of the rim 3252, to facilitate connection to an air circuit 4170 and/or connection port 3600.

In this configuration, the hollow protrusion 3250 is close to the patient's face and receives the air circuit from a generally inferior and partially anterior position and angle. One advantage of this aspect is that assists with providing a low-profile to the patient interface 3000. The patient can turn their head into the pillow during side sleeping with a reduced likelihood of disrupting the seal with the seal-forming structure 3100 through disruptive forces received from the patient's pillow against components of the patient interface 300 projecting in the anterior direction. Additionally, the close connection and downward angle of the air circuit 4170 means that the air circuit 4170 is located closer to the patient's face. Forces that the air circuit 4170 applies to the plenum chamber 3200 (such as tube drag from the weight of the air circuit 4170 or from forces acting on the air circuit 4170) are applied from a smaller distance away from the seal formed by the seal-forming structure 3100, therefore exerting less moment on the seal.

The stiffness of the hollow protrusion 3250 between adjacent portions of the fascia portion 3210 and the rim 3252 is lower than at least a superior portion 32 RR of the fascia portion 3210. As may be seen in FIGS. 8-1 to 8-5, this lower stiffness may be provided by a relatively thinner wall in this region of the hollow protrusion 3250. In this example, the thickness of the superior portion 3254, and other adjacent portions, of the fascia portion 3210 tapers down to the hollow protrusion 3250. An inferior portion 3256 of the hollow protrusion 3250 is provided inferior to the hollow protrusion 3250, having a lower stiffness than the superior portion 3254.

The result of this arrangement is that the hollow protrusion 3250 can deform significantly yet still function. More particularly, the hollow protrusion 3250 may deform without occluding the connection between the plenum chamber 3200 and the air circuit 4170. Further, the flexibility of the hollow protrusion 3250 may provide a degree of decoupling between the air circuit 4170 and the seal-forming structure 3100, to reduce the likelihood of forces received by the air circuit 4170 breaking the seal with the patient's face.

This reduced spacing of the supply conduit connection from the seal-forming structure also has an advantage for when the patient is sleeping in a supine position with their face facing upwards. The hollow protrusion 3250, being close to the patient's face and opening in a generally inferior direction, means that the air circuit 4170 is kept close to the patient, with the weight of the air circuit 4170 assisting the seal-forming structure 3100 to create a seal against the patient's chin region. The flexibility of the facia portion 3210 in the vicinity of the hollow protrusion 3250 also allows for deformation to absorb some of the forces exerted by the air circuit 4170. Without this flexibility, the positioning and stabilising structure 3300 may need to be tightened to counter these forces, potentially resulting in discomfort to the patient.

In the examples shown in FIGS. 11-1 to 13-3, the plenum chamber 3200 comprises two inlet ports 3240. The inlet ports 3240 are provided to lateral sides of the fascia portion 3210. The inlet ports 3240 in these examples are configured to connect to conduits which connect to a decoupling component located above the patient's head where the conduits are connected to the air circuit. The conduits may form part of the positioning and stabilising structure 3300, i.e., they may be "headgear conduits". In the examples shown, the inlet ports 3240 may receive combined headgear and conduit connection assemblies, in order to provide multiple functions such as venting, supply of the flow of air and headgear attachment points. The combined headgear and conduit connection assemblies may also comprise an AAV. The inlet ports 3240 in these examples are non-circular in shape.

While the inlet ports 3240 are provided in the lateral inserts 3214 in the examples shown in FIGS. 11-1 to 13-3, alternative examples are contemplated in which the inlet ports 3240 are formed directly in the fascia portion 3210.

5.3.1.4 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g., a liquid silicone rubber (LSR), or a biocompatible TPE.

A seal-forming structure 3100 in accordance with the present technology may be constructed from a soft, flexible, resilient material such as LSR, or a TPE.

In certain forms of the present technology, a system is provided comprising more than one seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

In certain forms of the present technology, regions of the seal-forming structure 3100 may have a different stiffness compared to other regions of the seal-forming structure 3100. Such differences in stiffness may be provided by one or more of: wall thickness; stiffer materials (e.g. the same material with a different durometer hardness, or another material), and a reinforcing structure (e.g. a tie or a rib, an undercushion, portion or a chassis, or the like) across various examples of the present technology.

In examples, the seal-forming structure 3100 may be substantially as described in International Application No. PCT/AU2019/050278, the entire contents of which are incorporated herein by reference.

5.3.1.4.1 Sealing Mechanisms

In one form, the seal-forming structure 3100 includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g., by adjacent regions of the sealing flange.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.4.2 First Embodiment of Nasal Region

In certain forms of the present technology, the seal-forming structure 3100 comprises a medial portion configured to form a seal to inferior surfaces of the patient's nose. The medial portion may seal to an inferior periphery of the patient's nose (e.g., surrounding the patient's nares and to the patient's lip superior). In examples, the seal-forming structure 3100 may be configured to contact the patient's face below the bridge of the nose or below the pronasale.

As shown in FIGS. 7-1 to 8-5, 10 to 11-5 and 13-1 to 13-3, the seal-forming structure 3100 comprises a medial portion configured to seal to an inferior periphery of the patient's nose in use and intermediate portions configured to be located against or proximate the ala of the patient's nose in use. More particularly, the medial portion includes a superior-facing medial portion 3111 and an anterior-facing medial portion 3115. Additionally, the intermediate portions comprise a superior-facing intermediate portion 3121 and an anterior facing intermediate portion 3125. Most or all of the contact of the intermediate portions with the patient's nose is made by the superior-facing intermediate portion 3121.

A lip superior portion 3116 may also make significant contact with inferior surfaces of the patient's nose along with the patient's lip superior. In some examples a majority of the seal formed by the seal-forming surface 3100 to the inferior periphery of the patient's nose may be made by the superior-facing medial portion 3111 and lip superior portion 3116. The superior-facing medial portion 3111 and lip superior portion 3116 may each comprise a lower stiffness than other portions of the seal forming structure 3100, which in some examples of the present technology is provided by a lower wall thickness than other portions of the seal forming structure 3100. The inferior surfaces of the patient's nose and lip superior can have complex geometry and can also be very sensitive to pressure. Accordingly, it is advantageous for the areas of the plenum chamber 3200 that will contact or seal against these locations to be flexible and compliant, to avoid exerting excessive pressure on the face at these regions. The low stiffness, which in these examples is provided by a thin wall thickness in the medial portion of the nasal portion 3230 of the seal-forming structure 3100 proximate the nasal holes 3272, enable the cushion to readily deform to seal against the surfaces on the underside of the patient's nose, e.g., against the pronasale towards the anterior direction, the nasal ala on either lateral side and the lip superior.

The low wall thickness of the superior-facing medial portion 3111 and lip superior portion 3116 also enables the seal-forming structure to inflate in these portions to conform to the geometry of inferior surfaces and periphery of the patient's nose. The thin wall can deform and inflate under pressure, conforming to the surfaces of the patient's face to create an effective and yet comfortable seal.

The superior-facing medial region 3111 superior and anterior to the nasal holes 3272 of the seal-forming structure is intended to seal against the inferior and partially anterior surfaces of the patient's pronasale. This area of the seal-forming structure 3100 may be provided with a low wall thickness because the pronasale can be a relatively sensitive area to many patients. The medial portion may extend from a superior-facing medial portion 3111 on the posterior (i.e., patient facing) side of the cushion over a medial saddle portion 3112 and peripheral edge and into an anterior-facing medial portion 3115 on the anterior (i.e., non-patient facing) side of the seal-forming structure. A thin wall thickness in this region avoids exerting excessive pressure on the sensitive pronasale area.

A lip superior portion 3116 of the seal-forming structure 3100 is intended to seal against the lip superior. The lip superior portion 3116 is provided medially and inferior and posterior to the nasal holes 3272. The lip superior portion 3116 may comprise a low wall stiffness. In some examples the low wall stiffness is provided by a low wall thickness. Similarly to the area of the seal-forming structure 3100 intended to seal against the pronasale, a low wall thickness extends over the medial inferior/posterior region of the nasal portion 3230 of the seal-forming structure 3100 because the lip superior can be a sensitive area. The low wall thickness may exert lower forces on the lip superior than would be exerted by a relatively thick wall thickness.

As shown in FIGS. 7-1 to 8-5, 10 to 11-5 and 13-1 to 13-3, the nasal portion 3230 of the seal-forming structures 3100 in these examples comprises two lateral portions 3231. Each lateral portion 3231 of a nasal portion 3230 may comprise a patient-facing side and a non-patient-facing side. The patient-facing side may face in a medial and posterior direction while the non-patient-facing side may face in a lateral and anterior direction. Both the patient-facing side and the non-patient-facing side may face partially in a superior direction.

A further advantage of a flexible medial region of the nasal portion 3230 is that it enables the sides of the nasal portion 3230 to be pulled inwardly (e.g., in a medial direction) when the patient dons the patient interface 3000 and the patient's nose exerts a downward force on the superior-facing medial portion 3111 of the seal-forming structure. The inwards pull on the sides of the nasal portion 3230 towards the sides of the patient's nose may improve the seal since the seal-forming structure 3100 is pulled into and around the inferior periphery of the patient's nose.

In embodiments of the patient interface 3000 in which the plenum chamber 3200 includes a rigidiser 3500, the flexible medial region allows the sides of the nasal portion 3230 to be pulled inwardly in use. However, the rigidiser 3500 may limit or substantially prevent outward flexing of the flexible medial portion beyond a desired limit. This can assist in preventing or eliminating flaring of the nasal sealing portion which would affect sealing performance of the mask. Therefore, the embodiments of the patient interface 3000 having a rigidiser may achieve the benefits of having a flexible interface which can provide increased comfort and seal performance, yet address factors which could adversely affect seal performance in a more flexible patient interface. Although the lateral sides of the nasal portion 3230 are pulled inwards, the anterior portion retains enough structural rigidity to maintain the overall shape of the seal-forming structure 3100 and prevent creases from creating leak paths.

While, in the areas of the seal-forming structure 3100 discussed above, it is advantageous for the seal-forming structure 3100 to have a low wall thickness to allow it to comfortably conform to complex geometry, in some regions of the seal-forming structure 3100 a relatively thicker wall thickness is advantageous in other forms of the technology.

In examples, the seal-forming structure 3100 may be generally even thicker towards its anterior side closer to the fascia portion 3210. As discussed above, the seal-forming structure 3100 comprises lateral support portions 3151 in the form of thickened regions on the partially-anterior facing lateral sides of the nasal portion 3230 of the seal-forming structure 3100. The thicker regions of the seal-forming structure 3100 proximate the shell fascia portion provide good support and structural rigidity to the seal-forming structure 3100.

While thick areas proximate the fascia portion 3210 may be advantageous in providing structural rigidity, the nasal portion 3230 of the seal-forming structure 3100 still retains a degree of flexibility to enable the sides of the seal-forming structure 3100 to be pushed outwardly or pulled inwardly to accommodate noses of different widths.

For example, the non-patient facing sides or regions (e.g., anterior sides, at least partially anterior-facing sides) of the nasal portion 3230 of the seal-forming structure 3100 (particularly the non-patient contacting regions on either side of nasal portion 3230 of the seal-forming structure 3100) are thick enough to provide sufficient structural rigidity to the seal-forming structure 3100, but are thin enough so that when the seal-forming structure 3100 is donned by a patient with a long narrow nose, the downward forces exerted by the patient's nose on the superior-facing medial region 3111 are able to pull the sides of the nasal portion 3230 inwardly somewhat to bring the patient-contacting surfaces of the seal-forming structure 3100 on either side of the patient's nose into good contact with the patient's nose. Similarly, the structure of the nasal portion 3230 of the seal-forming structure 3100 is sufficiently flexible that, if a patient with a wider nose dons the seal-forming structure 3100, there are not excessive inwards forces on the sides of the patient's nose (which may occur if the seal-forming structure is too stiff to tolerate a wider nose). A number of different sizes for the seal-forming structure 3100 are also able to be provided to accommodate different ranges of nose widths.

In some examples of the present technology, the plenum chamber 3200 comprises lateral support portions 3151 on the anterior side of the nasal portion 3230 of the plenum chamber 3200. The lateral support portions 3151 may have a higher resistance to deformation than one or more adjacent portions of the seal-forming structure 3100. The lateral support portions 3151 may be stiffer than regions of the plenum chamber 3200 superior to lateral support portions 3151. Additionally, or alternatively, the lateral support portions 3151 may be stiffer than a medial region of the plenum chamber 3200. The regions of relatively greater stiffness may be in the form of fins configured to provide areas of relatively high rigidity in comparison to surrounding areas of the plenum chamber. The lateral support portions 3151 may be substantially fin shaped (e.g. having a curved superior boundary and a flatter inferior boundary). A fin shape, in particular the provision of a curved superior boundary or edge, is advantageous as the superior edge or boundary of the lateral support portion 3151 follows the curvature of the superior periphery of the nasal portion 3230. This provides a consistent height of the nasal portion 3230 above the fascia 3210, which may be useful for providing consistent or controlled stiffness to the structure of the nasal portion 3230.

In some examples of the present technology, the plenum chamber includes reinforcing at a base of the nasal portion 3230 to assist in preventing collapsing. In examples, as shown in FIG. 8-1 to 8-5, the thicker fascia portion 3210 extends along the base of anterior facing portion of the nasal portion 3230, and at least partly around the lateral sides of same. As seen in at least FIGS. 8-1, 8-3 and 8-5, in examples a portion of the fascia portion 3210 extends at least partially below the lateral support portions 3151 to provide reinforcing.

As shown in FIGS. 7-1 and 7-2 in particular, there is an oronasal transition 3275 at the periphery of the plenum chamber 3200 where the nasal portion 3230 and oral portion 3260 connect. While the periphery of the seal-forming structure 3100 should preferably be sufficiently stiff that it can support the overall shape of the seal-forming structure 3100 and prevent large creases and buckling, the shape of the periphery may be varied more than the regions that are in contact with the patient's face and the nearby regions (i.e. the thin zones and the thicker zones which prevent creases from creating leak paths past the patient's face). In any case, the oronasal transition 3275 between the nasal portion and oral portions of the seal-forming structure 3100 is relatively stiff (e.g., by being relatively thick) in comparison to low stiffness portions of the seal-forming structure 3100 such as the superior-facing medial portion 3111 in order to prevent creases or buckling from occurring and creating leaks between theses portions. Alternatively, the oronasal transition 3275 may be reinforced by any suitable means such as an undercushion, ribs, a portion of the shell or a frame or the like.

5.3.1.4.3 Oral-Region

In one form, the non-invasive patient interface 3000 comprises a seal-forming structure 3100 that forms a seal in use on an upper lip region (that is, the lip superior) of the patient's face. The seal forming structure 3100 may comprise a lip superior portion 3116 configured to form a seal to the lip superior of the patient.

In one form, the seal-forming structure 3100 includes a saddle-shaped region constructed to form a seal in use on an upper lip region of the patient's face.

In one form the non-invasive patient interface 3000 comprises a seal-forming structure 3100 that forms a seal in use around the patient's mouth at an oral portion 3260. The seal-forming structure 3100 may form a seal on a chin-region of the patient's face.

In one form, the seal-forming structure 3100 includes a saddle-shaped region constructed to form a seal in use on a chin-region of the patient's face.

In the examples of the plenum chamber 3200 shown FIGS. 7-1 to 8-5, 10 to 11-5 and 13-1 to 13-3, the seal-forming structure 3100 comprises a lip inferior portion 3118 which forms a seal against the chin region of the patient. In an example, the seal-forming structure 3100, including the lip inferior portion 3118, does not extend below the patient's chin (i.e., below the mental protuberance) in use or engage the patient's face below the chin (i.e., below the mental protuberance) in use. The lip inferior portion 3118 of the seal-forming structure may seal against the lip inferior and supramenton of the patient. Additionally, in these examples, the seal-forming structure 3100 comprises an oral hole peripheral portion 3117. The lip inferior portion 3118 may be connected to (e.g., contiguous with) the lip superior portion 3116 via the oral hole peripheral portion 3117. The seal-forming structure 3100 comprises a relatively low wall thickness at the oral hole peripheral portion 3117 and at the lip inferior portion 3118 of the seal-forming structure 3100 which lies against the chin region (in comparison to other regions). The low wall thickness in these locations assists in achieving an effective, comfortable seal. The seal-forming structure 3100 in these regions is able to readily conform to any complex geometry (e.g. the labiomandibular creases).

In these examples, the oral portion 3260 comprises posterior-facing lateral portions 3135 on the patient-contacting side of the seal-forming structure 3100. Immediately around the oral hole 3271 at the oral hole peripheral portion 3117 the wall thickness is low in comparison to other regions of the seal-forming structure 3100, however in these examples there are posterior-facing lateral portions 3135 on either lateral side of the oral hole peripheral portion 3117 which are thicker than the oral hole peripheral portion 3117. The areas that these regions contact in use, i.e., the patient's cheeks, may generally not be as sensitive as other areas of the face and therefore patients may generally tolerate the seal-forming structure 3100 having a greater wall thickness/stiffness in these areas. Additionally, the posterior-facing lateral portions 3135 of the oral portion 3260 curve away from contact with the patient's face which reduces the area of contact on the patient's face at these regions. In alternative examples the posterior-facing lateral portions 3135 of the oral portion 3260 may not be thicker and may instead be stiffened by another means, such as by reinforcing structures (e.g., ribs), a stiffer material, an undercushion or the like.

Further from contact with the patient (e.g., closer to the fascia portion 3210) than the posterior-facing lateral portions 3135 at the lateral periphery of the oral portion 3260 are lateral portions 3145 of the oral portion 3260. In these examples, the lateral portions 3145 are thicker than the posterior-facing lateral portions 3135 of the oral portions. Most, or all, of the lateral portions 3145 are unlikely to be in contact with the patient's face in use and accordingly, patient comfort is a less important design consideration for these regions and the wall thickness can be higher in these regions than in the patient-contacting regions. The higher wall thickness may provide structural rigidity to the overall shape of the oral portion 3260 of the seal-forming structure 3100. In some examples, the further away from the patient's face a particular region of the seal-forming structure 3100 is, the thicker that region is, unless there is a reason for providing flexibility to that region (e.g., to enable the sides of the nasal portion of the seal-forming structure 3100 to deform). The lateral portions 3145 define a lateral periphery of the seal-forming structure 3100 in the oral portion 3260.

In the example shown in FIG. 7-1 to 8-5, a medial portion of the oral portion 3260 inferior to the hollow protrusion 3250, between the lip inferior portion 3118 and the inferior portion 3256 of the hollow protrusion 3250, has a lower stiffness than the superior portion 3254 of the fascia portion 3210 superior to the hollow protrusion 3250. In this example, this medial portion of the oral portion 3260 has a low wall thickness which continues around the lower periphery of the seal-forming structure 3100 and into the inferior portion 3256 of the hollow protrusion 3250, which assists with encouraging the hollow protrusion 3250 to deform in an inferior direction and thereby direct the weight of the air circuit towards the chin region and improve the seal. The deformation of the hollow protrusion 3250 in this manner when the patient is in a supine position also advantageously allows the air circuit connection to move closer to the patient's face, providing a lower profile to the patient interface 3000.

5.3.1.4.4 Forehead Region

In one form, the seal-forming structure forms a seal in use on a forehead region of the patient's face. In such a form, the plenum chamber may cover the eyes in use.

5.3.1.5 Deformation Behaviour of Plenum Chamber in Examples of the Present Technology An expected effect of the configuration of plenum chambers 3200 exemplified in FIG. 7-1 to FIG. 13-2 is that the flexibility provided will allow the plenum chamber 3200 to be fitted to a wider range of patient face shapes and sizes. This may mean, for example, that only two sizes of plenum chamber 3200 may be required to fit to a particular target population where, in other more traditional cushion modules, three sizes were required. Alternatively, a set of three plenum chamber 3200 sizes may fit a wider population than a set of three more traditional cushion modules.

Another effect is that each size of the plenum chamber 3200 is expected to fit to a wider variety of facial shapes and/or features. The high level of flexibility means that the plenum chamber 3200 may be better able to accommodate unusual or particularly complex facial geometry and still form an effective and stable seal than less flexible cushions. For example, the recesses on either side of the lower portion of the nose, where the nasal ala meet the face is a difficult area to seal to due to the significant concavity that is often present. The seal-forming structure 3100 of the plenum chamber according to aspects of the present technology may be more readily able to wrap around the patient's nose and fit into these concavities.

In addition to the ability of the plenum chamber 3200 to accommodate a wide range of face shapes and sizes, the more flexible nature may make the plenum chamber 3200 more comfortable for many patients. For example, a headgear tension may be required to achieve a seal using a plenum chamber 3200 may be lower than more traditional cushion modules, meaning less force may be exerted on the face and/or head of the patient.

The most prominent effect on deformation provided by the flexible nature of the plenum chamber 3200 may be the ability to bend about the vertical axis—i.e. an axis in an inferior-superior direction. The flexibility of the fascia portion 3210 in at least the medial portion 3219 allows the lateral sides of the plenum chamber 3200 being brought together. Any headgear connections are, in the examples, provided at the lateral sides of the plenum chamber 3200, meaning the medial portion of the fascia portion 3210 is able to bend. Additionally, on the posterior side of the plenum chamber 3200, the medial portions of the seal-forming structure 3100 are relatively thin, which facilitates bending about the vertical axis. The lateral portions of the seal-forming structure 3100 are thicker than the medial portions, meaning they do not bend as easily as the medial portion does.

This can help achieve a good seal between the sides of the seal-forming structure 3100 and the face across a wider range of facial geometry and sizes. For example, the lateral sides of the seal-forming structure 3100 can bend inwardly to seal against narrow cheeks. Alternatively, the seal-forming structure 3100 can flatten out to comfortably seal against wide cheeks. Additionally, the ability to bend about the vertical axis helps the nasal portion 3230 of the seal-forming structure 3100 to wrap around the nose to fit into the recesses on either side of the nose at the base of the nose (i.e. where the ala meets the face).

The flexibility about a vertical axis may also enable the tension of the positioning and stabilising structure 3300 to have an increased effect on the seal behaviour. The positioning and stabilising structure 3300 on a more traditional patient interface pulls the seal-forming structure towards the face, whereas the positioning and stabilising structure 3300 on a plenum chamber 3200 according to the examples of the present technology may both pull the seal-forming structure 3100 into the face as well as help the seal-forming structure 3100 to wrap to conform to the facial geometry.

In addition, in embodiments where the plenum chamber 3200 is provided with a rigidiser 3500, the sealing characteristics of the patient interface may be improved, particularly at relatively higher internal pressures in the plenum chamber. For instance, the rigidiser may limit or prevent the sealing structures of the plenum chamber flaring outwardly in a way that adversely affects sealing performance. In such embodiments, the benefits of increased flexibility for fit and sealing performance are obtained, while also obtaining additional benefits for sealing performance.

Bending about a lateral axis—i.e. an axis in a left-right direction—may be used to adjust the angle of the nasal portion 3230 relative to the angle of the oral portion 3260. This may be particularly useful where separate upper and lower headgear straps are provided to the plenum chamber 3200 (for example upper straps 3310 and lower straps 3320 in the example of FIGS. 10-1 and 10-2). Some flexibility about a lateral axis may enable the upper straps 3310 and lower straps 3320 to each have distinct and independently adjustable effects on the fit of the nasal portion 3230 and the oral portion 3260.

For example, adjusting the upper straps 3310 can adjust the fit of the nasal portion 3230 independently from the fit of the oral portion 3260, and vice versa. In contrast with a traditional patient interface having a rigid shell, the flexible fascia portion 3210 in the examples of the present technology may deform due to headgear force vectors acting on flexible portions of the plenum chamber 3200. The ability to bend about a lateral axis may help the seal-forming structure 3100 to wrap to conform to facial geometry upon relative adjustment between upper straps 3310 and lower straps 3320—i.e. different relative tension in upper straps 3310 and lower straps 3320 can affect the way the seal-forming structure 3100 seals to the patient's face, since the plenum chamber 3200 can deform in response to different upper straps 3310 and lower straps 3320.

Flexibility of the plenum chamber 3200 may further allow bending about an inclined anterior-posterior axis of the nasal portion 3230 to allow the effective width of the nasal portion 3230 to change with respect to the oral portion 3260. This may enable patients with particularly wide/large noses relative to their mouths to be accommodated. Alternatively stated, this flexibility may enable a wider range of nose widths to be accommodated by the plenum chamber 3200.

The flexible nature of the plenum chamber 3200 may also allow twisting such that one lateral side can move in a posterior-anterior direction with respect to the other lateral side. The ability to twist in this manner helps the plenum chamber 3200 to accommodate torsional loads while maintaining a seal, and helps provide a decoupling effect whereby the left side of the plenum chamber 3200 is decoupled from the right side of the plenum chamber 3200 to a greater extent than traditional rigid shell configurations. This may be advantageous in preventing forces received at one side of the plenum chamber 3200 from adversely affecting the other side of the plenum chamber 3200, more particularly at the seal-forming structure 3100. A common situation when lateral forces can occur is when a patient sleeps on their side with the side of their face against the pillow. In such a situation, a rigid shell of a cushion can transfer lateral force from the pillow directly to the seal-forming structure, which can disrupt the seal. The ability to twist in this manner may also help with dynamic stability, for example if the patient moves their head from one side to the other or moves their face in a way that could disrupt the seal, the left side having a degree of decoupling from the right side may allow the seal-forming structure 3100 to have some tolerance to such disruptive forces.

5.3.2 Decoupling Portions

In examples of the present technology, the plenum chamber 3200 may include a decoupling portion between the oral portion 3260 and the nasal portion 3230. It is envisaged that this may assist in preventing tube drag and other forces (e.g. from the patient's pillow during side sleeping) received at the oral portion 3260 from being transferred to the nasal portion 3230 and affecting the seal at the nasal portion 3230.

In examples of the present technology, the plenum chamber 3200 may include a decoupling portion between the nasal portion 3230 and the fascia portion 3210.

In examples of the present technology, the plenum chamber 3200 may include a decoupling portion between the oral portion 3260 and the fascia portion 3210.

In examples of the present technology, the plenum chamber may include a decoupling portion between at least a portion of the seal forming structure 3100 and one of more plenum chamber inlet ports 3240. In the example shown in FIG. 7-1 to FIG. 8-5 the construction of the hollow protrusion may already provide a decoupling effect, as discussed above, however this may be improved by an additional decoupling portion In examples, a decoupling portion may be provided by one or more of: one or more gusset portions, and one or more pleats, one or more concertina portions.

5.3.3 Surface Finishes

In examples, at least a portion of the seal-forming structure 3100 may have a first surface finish, and other portions of the plenum chamber 3200 may have a second surface finish different from the first surface finish.

In examples, the first surface finish is provided in portions of the seal-forming structure 3100 in contact with the patient's face in use, wherein the first surface finish provides a greater coefficient of friction than the second surface finish. In examples, the first surface finish may be a polished finish. The polished surface finish may have a grippy, sticky feel to it so that there is higher friction acting against movement of the seal-forming structure 3100 against the patient's face. This is generally desired as it helps prevent movement of the plenum chamber 3200 when donned by a patient, thereby assisting in maintaining a seal.

In some examples, different regions of the seal-forming structure 3100 may have different surface finishes.

In examples, the second surface finish may be smoother to the touch than the first surface finish. A smooth finish may feel more comfortable to touch and can give the patient the impression that the mask is comfortable, which may improve the patient's compliance with therapy.

In examples, the second surface finish may be a textured surface finish. A textured surface may assist with providing a textile-like feel and/or appearance, which may help the patient interface to look and feel more like bedclothes than medical equipment and therefore may improve the patient's compliance with therapy. For example, the second surface finish may be flocked, whereby fibres (such as those used in forming textiles), can be included in the plenum chamber 3200. In examples, other parts of the patient interface 3000, such as headgear connections, could also be flocked to have the look and feel of textile material.

In alternative examples, a textured surface finish may be produced by textured features in tooling used in forming the plenum chamber; the textured surface finish may be provided by etching (for example, laser etching).

5.3.4 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap.

FIGS. 10-1 and 10-2 show a patient interface 3000 according to one example of the present technology having a positioning and stabilising structure 3300 and a plenum chamber 3200 having a seal forming structure 3100. The positioning and stabilising structure 3300 in this example includes a plurality of headgear straps connected to the headgear support 3302.

The plenum chamber 3200 of the exemplary patient interface 3000 shown in FIGS. 10-1 and 10-2 is the plenum chamber 3200 shown in FIGS. 7-1 to 8-5, although the positioning and stabilising structure 3300 may also be used with other plenum chambers 3200 in alternative examples of the present technology.

The positioning and stabilising structure 3300 may comprise a plurality of straps or strap portions connecting to the headgear supports 3302 and passing around the patient's head in order to support the plenum chamber 3200 in sealing position against the patient's face. It will be understood that a single "strap" may be formed by multiple lengths of material(s) that have been cut or formed separately and then joined together at their ends to create a longer length or single "strap" may be a single length of material(s).

In the example illustrated in FIGS. 10-1 and 10-2 the positioning and stabilising structure 3300 comprises a pair of upper straps 3310. Each upper strap 3310 is configured to pass between a respective eye and ear of the patient. Additionally, the positioning and stabilising structure 3300 comprises a pair of lower straps 3320 configured to lie over the patient's cheeks below the patient's cheekbones. In this example, the plenum chamber 3200 is held in position via a four-point connection to headgear straps via the headgear supports 3302.

The headgear supports 3302 comprise a pair of opposed upper strap connection points 3315 to which the upper straps 3310 connect. In this example, each upper strap connection point 3315 comprises an aperture. Each upper strap 3310 is able to connect to a respective upper strap connection point 3315 by passing through the aperture, looping back onto itself and securing to itself. Each upper strap 3310 may secured to itself via hook and loop materials configured to releasably bind to each other upon contact. In alternative examples, each upper strap 3310 may pass through a respective aperture, loop back onto itself and be secured onto itself with a band, clip or the like. In further alternative examples, the upper straps 3310 may connect to the headgear supports 3302 via side release buckle connections.

The headgear supports 3302 also comprise a pair of opposed lower strap connection points 3325 to which the lower straps 3320 connect. In this example, each lower strap connection point 3325 comprises a magnet. Each lower strap 3320 comprises a lower strap clip 3326 comprising a magnet or material that is attracted to the magnet at the lower strap connection point 3325. In this example, each lower strap clip 3326 comprises an aperture through which the end of a respective lower strap 3320 and is able to pass and then loop back and be secured onto itself, for example with hook and loop material, a band, a clip or the like. In alternative examples, the lower straps 3320 may connect to the headgear supports 3302 via side release buckle connections, onto hooks or via any other suitable connection.

In an example, the headgear supports 3302 and upper strap connection points 3315 are structured and arranged to direct a force/tension provided by the upper straps 3310 into a partially superior and partially posterior force vector applied to the plenum chamber 3200. The partially superior and partially posterior force vector urges, in particular, the nasal portion 3230 of the seal forming structure 3100 into sealing contact with the lower periphery of the patient's nose and the patient's upper lip.

The upper straps 3310 may each by selectively adjustable. For example, the effective length of each of the upper straps 3310 may be varied by changing how much of the upper strap 3310 is passed through the aperture at the respective upper strap connection point 3315 and looped back on itself. Passing more of the upper strap 3310 through the aperture effectively reduces the length of the upper strap 3310, allowing the force vectors to be modified and the fit of the patient interface 3000 to be adjusted.

In an example, the headgear supports 3302 and the lower strap connection points 3325 are structured and arranged to direct a force/tension provided by the lower straps 3320 into a partially posterior and partially inferior force vector applied to the plenum chamber 3200. The partially posterior and partially inferior force vector urges, in particular, the oral portion 3260 into sealing contact with the patient's face around the periphery of the patient's mouth. The partially inferior force applied by the lower straps 3320 may balances the partially superior force applied by the upper straps 3310 along with any inferiorly directed force that the patient's nose may apply onto the seal forming structure 3100.

The lower straps 3320 may each by selectively adjustable. For example, the effective length of each of the lower straps 3320 may be varied by changing how much of each lower strap 3310 is passed through the aperture in the respective lower strap clip 3326 and looped back on itself. Passing more of each lower strap 3320 through the aperture effectively reduces the length of the lower strap 3320, allowing the force vectors to be modified and the fit of the patient interface 3000 to be adjusted.

The positioning and stabilising structure 3300 may also comprise one or more of a top crown strap 3330, a pair of lateral crown straps 3332 and a neck strap 3334. In the example illustrated in FIG. 10-2, the upper straps 3310 and lower straps 3320 are connected to ends of a top crown strap 3330. The top crown strap 3330 is configured to pass around the patient's head and lie against superiorly and posteriorly facing surfaces. The top crown strap 3330 may be configured to overlie the parietal bone of the patient's skull. Each end of the top crown strap 3330 connects to a respective one of the upper straps 3310 and also to a respective one of a pair of lateral crown straps 3332. Each one of the lateral crown straps 3332 connects between the upper strap 3310 and the lower strap 3320 on a respective side of the patient's head. The inferior ends of the lateral crown straps 3332 are connected to each other by a neck strap 3334. The neck strap 3334 may be configured to pass across the sagittal plane and lie against inferior and/or posterior facing surfaces of the patient's head or lie against the back of the patient's neck. The neck strap 3334 may overlie, or lie inferior to, the occipital bone of the patient's skull.

The length of the top crown strap 3330 may be selectively adjustable. In the example illustrated in FIG. 10-2 the top crown strap 3330 is formed by two strap portions which are connected by a link having a pair of apertures. Each of the two strap portions forming the top crown strap 3330 is able to pass through a respective one of the apertures then loop back and secure to itself, for example via hook and loop material, a further clip, a band or the like. The amount of each top strap portion that passes through the link can be varied to adjust the length of the top crown strap 3330 and in turn adjust the fit of the positioning and stabilising structure 3300.

Once all the headgear straps have been adjusted and the desired fit of the patient interface 3000 has been achieved, the magnetic clip connection provided by the lower strap clips 3326 enables the lower straps 3320 to be quickly disengaged from the lower strap connection points 3325, allowing the patient interface 3000 to be removed from the patient without adjustment of straps. Similarly, when the patient dons the patient interface again, the lower strap clips 3326 can be quickly engaged at the lower strap connection points 3325 to fit the patient interface 3000 without the need to adjust straps. Further advantages and features of a positioning and stabilising structure comprising magnetic clips are described in WO 2014/110622, the entire contents of which are incorporated herein by reference.

In examples of the present technology, the ability to independently adjust left and right straps, and/or upper and lower straps (for example, upper straps 3310 may assist with shaping and adjusting the seal-forming structure 3100 to achieve a desired fit.

In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

FIGS. 13-1 to 13-3, and more particularly FIG. 13-3, show a patient interface 3000 comprising the plenum chamber 3200 shown in FIGS. 11-1 to 11-5. The patient interface 3000 in this example also comprises a positioning and stabilising structure 3300 to hold the plenum chamber 3200 in sealing position on the patient's face in use. The positioning and stabilising structure 3300 in this example comprises a pair of headgear tubes 3340. The pair of headgear tubes 3340 are connected to each other at their superior ends and are each configured to lie against superior and lateral surfaces of the patient's head in use. Each of the headgear tubes 3340 may be configured to lie between and eye and an ear of the patient in use. The inferior end of each headgear tube 3340 is configured to fluidly connect to the plenum chamber 3300. In this example, the inferior end of each headgear tube 3340 connects to a headgear tube connector 3344. The headgear tube connector 3344 may be permanently or releasably connected to a headgear connector 3246 configured to connect to the inlet port 3240 of the lateral insert 3214 in the fascia portion 3210 of the plenum chamber 3200. The interior rim 3215 of the lateral insert 3214 includes locating features to secure the headgear connector 3246 in place. The positioning and stabilising structure 3300 comprises a conduit headgear inlet 3390 at the junction of the two headgear tubes 3340. The conduit headgear inlet 3390 is configured to receive a pressurised flow of gas, for example via an elbow comprising a connection port 3600, and allow the flow of gas into hollow interiors of the headgear tubes 3340. The headgear tubes 3340 supply the pressurised flow of gas to the plenum chamber 3200.

The positioning and stabilising structure 3300 may comprise one or more straps in addition to the headgear tubes 3340. In this example the positioning and stabilising structure 3300 comprises a pair of upper straps 3310 and a pair of lower straps 3320. The posterior ends of the upper straps 3310 and lower straps 3320 are joined together. The junction between the upper straps 3310 and lower strap 3320 is configured to lie against a posterior surface of the patient's head in use, providing an anchor for the upper strap 3310 and lower straps 3320. Anterior ends of the upper straps 3310 connect to the headgear tubes 3340. In this example each headgear tube 3340 comprises a tab 3342 having an opening through which a respective upper strap 3310 can be passed through and then looped back and secured onto itself to secure the upper headgear strap 3310 to the headgear tube 3340. The positioning and stabilising structure 3300 also comprises a lower strap clip 3326 provided to the anterior end of each of the lower straps 3320. Each of the lower strap clip 3326 is configured to connect to a lower connection point 3325 on the plenum chamber 3200—in the example of FIG. 13-1 to 13-3, the lower connection point 3325 is provided on the headgear connector 3246. In this example, the lower strap clips 3326 are secured magnetically to the lower connection points 3325. In some examples, there is also a mechanical engagement between the lower strap clips 3326 and the lower connection points 3325.

The headgear tube connectors 3344 may be configured to allow the patient to breathe ambient air in the absence of pressure within the plenum chamber 3200. Each headgear tube connector 3344 may comprise an anti-asphyxia valve (AAV). The AAV in each headgear tube connector 3344 may be configured to open in the absence of pressure within the plenum chamber 3200 in order to allow a flow of air between the interior of the plenum chamber 3200 and ambient. Each AAV may be biased into a configurations which blocks the flow of air from the interior of the plenum chamber 3200 into a respective headgear tube 3340 but allows for the exchange of air between the plenum chamber 3200 and ambient. When the headgear tubes 3340 are pressurised the AAV in each headgear tube connector 3344 may prevent the exchange of air between the interior of the plenum chamber 3200 and ambient but allow for a flow of air from the respective headgear tube 3340 into the plenum chamber 3204 breathing by the patient.

The examples shown in FIG. 10 and FIG. 13-1 to 13-3 have a common support base for the upper and lower headgear connectors. That is, on each side of the plenum chamber 3200, the upper headgear strap 3310 (or headgear tube 3340) and the lower headgear strap 3320 both connect to a common rigid connector. However, in some examples the plenum chamber 3200 may have separated upper and lower headgear connectors. It is envisaged that differences in tension between the upper headgear straps and the lower headgear straps influence deformation of the plenum chamber 3200, and behaviour of the seal-forming structure 3100. Separate upper and lower headgear connections (i.e. upper and lower headgear connections that are able to move relative to one another when the cushion flexes) may allow some bending about the horizontal axis to assist with achieving a suitable fit with a wider range of patients, while also allowing that bending to be adjustable to further improve the fit range and the extent to which the patient interface 3000 may be adjusted to achieve a more comfortable and effective fit. As discussed in relation to the headgear supports 3302, separated headgear connectors may be used to assist with providing at least a part of requisite rigidity to the fascia portion 3210.

5.3.5 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200, more particularly in the fascia portion 3210. Alternatively, the vent 3400 is located in a component provided to the plenum chamber 3200, for example a decoupling structure (e.g. a swivel). In examples, the patient interface may include a swivel elbow assembly having vents substantially as described in International Publication No. WO 2017/049357 A1, the entire contents of which are incorporated herein by reference.

In the example illustrated in FIGS. 10-1 and 10-2, the patient interface 3000 comprises a vent 3400. The vent 3400 in this example comprises holes forming part of the vent 3400 around the periphery of the inlet connection port 3600.

5.3.6 Decoupling Structure(s)

In one form the patient interface 3000 includes at least one decoupling structure, for example, a swivel or a ball and socket.

5.3.7 Connection Port

Connection port 3600 allows for connection to the air circuit 4170.

In the example shown in FIG. 9, an inlet connection port 3600 is rigid, and generally tubular in construction, having a first end 3602 and a second end 3604. An annular groove 3606 is provided around its exterior at the first end 3602, configured to receive the connection port ridge 3608 (as shown in FIG. 7-6) to locate the inlet connection port 3600 relative to the plenum chamber 3200.

The inlet connection port 3600 includes a conduit connection portion 3610 at the second end 3604, to which the air circuit 4170 is connected. A vent 3400 is provided in the form of a plurality of holes around the periphery of the inlet connection port 3600 between the annular groove 3606 and the conduit connection portion 3610.

5.3.8 Forehead Support

In one form, the patient interface 3000 includes a forehead support 3700 such as that shown in FIG. 3A. In other examples, e.g., as shown in FIGS. 7-1 to 13-3, the patient interface 3000 may exclude a forehead support. Furthermore, the patient interface 3000 may be configured not to contact the patient's forehead at all.

5.3.9 Anti-Asphyxia Valve

In one form, the patient interface 3000 includes an anti-asphyxia valve.

As described above, the patient interface 3000 may comprise one or more headgear tubes 3340 connected to a plenum chamber 3200 via a headgear tube connector 3344 comprising an anti-asphyxia valve. Alternatively, or additionally, the patient interface 3000 may comprise a swivel elbow configured to connect to a supply conduit, the swivel elbow comprising an anti-asphyxia valve. In other examples, an anti-asphyxia valves may be built into a plenum chamber 3200, for example by being provided to the fascia portion 3210 of the plenum chamber 3200.

5.3.10 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 Second Embodiment of a Patient Interface

Referring now to FIGS. 16 to 31 which show an embodiment of a patient interface 6000 according to an aspect of the technology. The patient interface 6000 generally comprises a seal forming structure 6100 and a plenum chamber 6200 as are discussed below.

5.4.1 Sealing Mechanisms

In one form, the seal-forming structure 6100 includes a sealing flange utilizing a pressure assisted sealing mechanism. In use, the sealing flange can readily respond to a system positive pressure in the interior of the plenum chamber 6200 acting on its underside to urge it into tight sealing engagement with the face. The pressure assisted mechanism may act in conjunction with elastic tension in the positioning and stabilising structure.

In one form, the seal-forming structure 6100 comprises a sealing flange and a support flange. The sealing flange comprises a relatively thin member with a thickness of less than about 1 mm, for example about 0.25 mm to about 0.45 mm, which extends around the perimeter of the plenum chamber 6200. Support flange may be relatively thicker than the sealing flange. The support flange is disposed between the sealing flange and the marginal edge of the plenum chamber 6200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.4.1.1 Nasal Region

Referring next to FIGS. 16 to 27, in certain forms of the present technology, the second seal forming structure 6102 comprises a central portion 6110 configured to seal to surfaces of the patient's nose in use. The central portion may seal to an inferior periphery of the patient's nose (e.g. surrounding the patient's nares) and to the patient's lip superior. In examples a portion of the seal forming structure may engage the patient's septum. The second seal forming structure 6102 may further comprise lateral portions 6111 on lateral sides of the central portion 6110. In examples, the seal forming structure 6102 may be configured to contact the patient's face below the bridge of the nose or below the pronasale.

As best seen in FIGS. 19 and 25-28, posterior surfaces 6112 of the lateral portions 6111 slope forward in a superior/anterior direction from the boundary 6103 of the first and second seal forming structures 6101, 6102 such that in profile the posterior side of the nasal part of the mask slopes forward.

In embodiments provided with a ridge 6120 (as described further below), the posterior surfaces 6112 of the lateral portions 6111 may slope forward from the ridge 6120.

In some forms of the technology the posterior surfaces 6112 of the lateral portions 6111 form an angle with a mid-contact plane of the mask of between 20° and 90°.

As shown in FIG. 26, in some embodiments the lateral portions 6111 are configured such that no part of the patient interface 6000 contacts the patient's alar crest point 1020 when in use.

Configuring the lateral portions 6111 to slope in this way results in a smaller portion of the nasal part of the interface 6000 extending over the sides of the ala than some similar interfaces of the prior art. In some forms of the technology this results in the portion of the ala which is in contact with the interface 6100 being reduced relative to interfaces with lateral portions which slope backward, toward the patient's face, thereby reducing the proportion of the ala which can be deformed and occluded by the interface 6100, for example when the patient sleeps on their side with the interface in contact with a pillow.

5.4.1.2 Boundary of Oral and Nasal Regions

With particular reference to FIGS. 16, 18, 25 and 27, in one form of the technology the boundary between the first sealing forming structure 6101 and the second seal forming structure 6102 forms or comprises a corner or ridge 6120. In use, the corner or ridge 6120 may engage the patient's face above the lip superior and immediately below the nose.

In embodiments the corner or ridge 6120 forms a sharper angle than the equivalent portion or area of some oro-nasal masks of the prior art, for example those described in PCT application No. PCT/AU2019/050278.

The sharper angle reduces the likelihood of creases forming in the first and/or second seal forming structures 6101, 6102 on or adjacent the corner or ridge 3120 when the mask is donned and therapy is applied. Some oro-nasal patient interfaces which do not use such a structure may require a very thin, rounded formation in this area which may be less resistant to creasing. By contrast, the corner or ridge 6120 may be stiffer, and may hold its shape better, than such interfaces and may therefore seal better against the concavities and creases present around the patient's nose. This effect may be enhanced in embodiments which are provided with support portions, for example support portions 6260 as described herein, which resist or oppose compression of this region.

In some forms of the technology the radius of the corner or ridge 6120 may be less than 2 mm, for example around 1.75 mm. In one form of the technology the radius may vary from approximately 1.75 mm in the centre of the ridge to approximately 0.75 mm at the lateral portions.

The angle formed by the first and second sealing structures may be between 20 degrees and 90 degrees, for example 36 degrees.

In some forms of the technology, the corner or ridge 6120 may extend across substantially an entire boundary 6103 between the first seal forming structure 6101 and the second seal forming structure 6102. In embodiments the corner or ridge 6120 may engage the patient's face at least approximate the entrances to the nares, for example where the ala meets the face above the lip superior, as indicated by areas 1010 in FIG. 29.

5.4.1.3 Oral Region

As is described above, in one form the non-invasive patient interface 6000 comprises a first seal-forming structure 6101 that forms a seal in use around the patient's mouth. The first seal forming structure 6101 may form a seal on a chin-region of the patient's face.

In one form, the seal-forming structure includes a saddle-shaped region constructed to form a seal in use on a chin-region of the patient's face.

The seal forming structure 6100 comprises a lip inferior portion 6130 which forms a seal against the chin region of the patient and/or the lip inferior and/or supramenton of the patient. The lip inferior portion 6130 may be connected to (e.g. contiguous with) a lip superior portion 6131 via an oral hole peripheral portion 6132, as shown in FIG. 25.

The seal forming structure 6100 comprises a relatively low wall thickness (compared to other portions of the interface), for example less than 0.7 mm, at the oral hole peripheral portion 6132, the lip inferior portion 6130 of the seal forming structure which lies against the chin region, and at least the centre of the lip inferior portion 6130. The low wall thickness in these locations assists in achieving an effective, comfortable seal. The seal forming structure in these regions is able to readily conform to any complex geometry.

In some forms of the technology the oral hole 6133 is substantially trapezoidal rather than oval or elliptical. This shape of oral hole may allow the interface 6000 to be particularly compact.

5.4.2 Plenum Chamber

In some forms, the plenum chamber 6200 (or at least a portion of the plenum chamber 6200) and the seal-forming structure 6100 are formed from a single homogeneous piece of material.

5.4.2.1 Angle of Nasal Portion is Adjustable

With particular reference to FIGS. 17, 19 and 25 to 27, in one form of the technology a first anterior wall portion 6240 of the nasal portion 6202 of the plenum chamber 6200 is more flexible than an immediately adjacent region of the oral portion 6201. The first anterior wall portion 3240 may be provided adjacent a boundary 6241 of the nasal and oral portions of the plenum chamber 3200. In embodiments the first anterior wall portion 6240 may be symmetrical about the mid-sagittal plane and may extend across at least 50% of the width of the nasal portion 6202 of the plenum chamber, for instance at least 80%. In some embodiments the first anterior wall portion 6240 may extend across substantially the entire width of the nasal portion 6202 of the plenum chamber.

In some forms of the technology a second anterior wall portion 6242 is less flexible than the immediately adjacent portions of the anterior wall. In some embodiments the second anterior wall portion 6242 is immediately adjacent the first anterior wall portion 6240 on an opposite side to the boundary 6241 of the of the nasal and oral portions of the plenum chamber. In embodiments the second anterior wall portion 6242 may be symmetrical about the mid-sagittal plane and may extend across at least 50% of the width of the nasal portion 6202 of the plenum chamber, for instance at least 80%. In some embodiments the second anterior wall portion 6242 may extend across substantially the entire width of the nasal portion 6202 of the plenum chamber.

The flexible first anterior wall portion 6240 may allow the patient contacting portions 6110 of the second seal forming structure 6102 to pivot or hinge about a region on the posterior side of the interface 3000. This may assist in allowing the interface to accommodate patients with a variety of angles between the bottom of the nose and the top lip (i.e. nasiolabial angles).

In embodiments featuring a corner or ridge 6120 between the first and second seal forming structures 6101, 6102, such as have been described above, the patient contacting portions 6110 may pivot or hinge about an area at or adjacent the corner or ridge 6120. In embodiments provided with one or more support portions 6260 (described further below), the hinging or pivoting region may be immediately superior to the support portions 6260.

As shown in FIG. 18, the first anterior wall portion 6240 may have a superior boundary 6243 and an inferior boundary 6244. One or both of the superior and inferior boundaries 6243, 6244 may be curved, for example such that a central portion of the boundary is inferior to the lateral portions, as shown. The first anterior wall portion 6240 may be substantially the same height across its width (i.e., the superior and inferior boundaries may be substantially parallel) or the height may vary across the width, for example such that the height of a central portion of the first anterior wall portion 6240 is greater than the height of the lateral portions, as shown in the embodiment in FIG. 18. Varying the curvature of one or both of the boundaries 6243, 6244 and/or the height of the first anterior wall portion 6240 may change the stiffness of the first anterior wall portion 6240, that is, its resistance to collapsing or folding in response to forces on the patient-contacting portions 6110 of the second seal forming means 6102.

Similarly, the second anterior wall portion 6242 may have a superior boundary 6247 and an inferior boundary 6248. In some forms of the technology the inferior boundary 6248 of the second anterior wall portion 6242 is the same as the superior boundary 6243 of the first anterior wall portion 6240. Both the superior and inferior boundaries 6247, 6248 of the second anterior wall portion 6242 may be curved, for example such that a central portion of the boundary is inferior to the lateral portions. The second anterior wall portion 6242 may be substantially the same height across its width (i.e., the superior and inferior boundaries may be substantially parallel) or the height may vary across the width, for example such that the height of a central portion of the second anterior wall portion 6242 is less than the height of the lateral portions.

In some forms of the technology other ways of configuring the first anterior wall portion 6240 to have a required stiffness may be used, in addition to or alternatively to curved boundaries. For example, the thickness of the first anterior wall portion 6240 may be selected to provide a required stiffness. In examples the first anterior wall portion 6240 may be thinner than the immediately adjacent portions of the plenum chamber wall. Additionally and/or alternatively, the first anterior wall portion 6240 may extend in a superior direction around a lateral edge of the second anterior wall portion 6242, as shown in FIG. 29, thereby providing a reduced stiffness/resistance to compression or collapse compared to embodiments in which the first anterior wall portion 6240 is not shaped this way.

The second anterior wall portion 6242 may assist in preventing collapse of the nasal portion 6202, and may provide support for the patient-contacting portions 6110 of the second seal forming means 6102, which are typically relatively thin. Insufficiently supported patient contacting portions may suffer from blowout of the sealing engagement with the patient's face. In one form the second anterior wall portion 6242 is thicker than the immediately adjacent portions of the plenum chamber wall. In certain forms the second anterior wall portion 6242 is provided as a thickened band of material, as shown in FIGS. 25-27. The first and second anterior wall portions 6241, 6242 may be made from the same material, for example as part of an integrally moulded shell 6250.

5.4.2.2 Flexible Shell

In some forms of the technology the shell 6250 may be made from a rigid material such as polycarbonate. However, in other forms of the technology the shell 6250, or portions of the shell 6250, may be somewhat flexible. For example, in examples the shell 6250 may be formed from a material which has a Young's modulus of 0.4 GPa or lower, for example foam. In some forms of the technology the shell 6250 may be made from a material having Young's modulus of 0.1 GPa or lower, for example rubber. In other forms of the technology the shell 6250 may be made from a material having a Young's modulus of 0.7 MPa or less, for example between 0.7 MPa and 0.3 MPa. An example of such a material is silicone.

In examples, the shell 6250 and one or both of the first and second seal forming structures 6101, 6102 may be formed from the same material.

In some forms of the technology, the shell 6250 may be sufficiently flexible that one or more components are added to provide a required stiffness in one or more areas or regions of the shell 6250. For example, one or more of a vent module; a headgear connector; a headgear connector connected to a rigidising arm and a rigidising member may be connected to the shell 6250 in such a way as to increase the stiffness of the plenum chamber 6200 in the area adjacent the component, for example as described further below. In some forms of the technology such components may be releasably connectable to the flexible shell 6250. Additionally or alternatively one more components may be permanently connected to the shell 6250, for example by bonding and/or overmoulding.

In some forms of the technology the shell 6250 may be generally flexible but may comprise stiffening portions having greater thickness than immediately adjacent portions of the shell 6250. Such stiffening portions may be configured as ribs or bands, for example extending laterally across the shell and/or extending in a superior-inferior direction, although many other configurations are possible. In some forms the shell may comprise a substantially rigid portion, for example manufactured from polycarbonate, as well as a somewhat flexible portion.

In some forms of the technology it may be preferable for a central portion 6251 of the anterior side of the oral portion 6201 of the plenum chamber to have a greater stiffness than the remainder of the plenum chamber 6200. In some forms of the technology the area of increased stiffness may be immediately inferior to the nasal portion 202, as shown in FIG. 29 and described further below, and/or immediately superior to the oral portion 6201. In one form of the technology, a portion of, or the entirety of, the first anterior wall portion 6240 may be an area of increased stiffness, rather than an area of increased flexibility. Providing increased stiffness in one or more of these areas may provide shape stability and may limit the extent to which the shell 6250 deforms as a result of headgear forces. Excessive deformation may result in the second seal forming structure 6102 occluding the nares. Avoiding such deformation may be particularly advantageous to patients with relatively wide noses, and may be less important, or in some cases undesirable, for patients with narrow noses. In addition, the areas of increased stiffness described may assist in reducing torsional deformation of the interface which may otherwise result in one side of the second seal forming structure 3102 losing contact with the patient's nose, thereby creating a leak path.

As shown in FIG. 29, in one form of the technology the shell 6250 may be provided with a rigid portion 6263, or at least a portion which is more rigid than the remainder of the shell, to which one or more connection ports 6600 are provided, e.g. moulded. In one form of the technology a rigid portion 6263 may be made from polycarbonate. This may provide more rigidity than a shell made exclusively of silicone. In one form the technology holes forming a vent 6400 are moulded into the rigid portion 6263. In some forms of the technology connectors 6310 for a positioning and stabilising structure are mounted on arms 6320 which provide some rigidity to the shell.

In one form of the technology the rigid portion 6263 extends laterally across the anterior of the plenum chamber near a superior boundary of the first anterior wall portion 6240, for example immediately below the second anterior wall portion 6242. The rigid portion 6263 may extend continuously between the connection ports 6600.

In some forms of the technology the connection ports 6600 may have a substantially elliptical shape in cross-section. The connection ports 6600 may be orientated such that a centreline of each port is substantially parallel to an exterior surface of the plenum chamber adjacent the port.

In some forms of the technology the rigid portion 6263 may protrude in an anterior direction relative to an adjacent face of the first anterior wall portion 6240, and may be shaped to increase resistance to bending.

In some forms of the technology the connectors 6310 and arms 6320 are provided inferior of the connection ports 6600, toward the lateral edges of the plenum chamber 6200. The connectors 6310 may be provided at lateral ends of the arms 6320.

FIG. 31 shows a plenum chamber 6200 with a vent mounting aperture 6410 into which a suitable vent portion or module may be inserted. The vent portion may be made from a relatively stiff material to increase the stiffness of the plenum chamber. In some forms of the technology the vent mounting aperture 6410 may be substantially elliptical in shape, with the minor axis of the ellipse being substantially parallel to a sagittal plane.

In the embodiment shown in FIG. 31 the vent mounting aperture is provided toward a superior border of the oral portion of the superior chamber 6201.

The embodiment shown in FIG. 31 is provided with connectors 6310 for a positioning and stabilising structure. The connectors 6310 may be mounted in relatively thicker regions of the shell 6250. In the embodiment shown the connectors 6310 are inferior of the vent mounting aperture 6410 and toward the lateral sides of the plenum chamber 6200. In some forms of the technology the connectors 6310 are substantially circular magnetic headgear connectors.

While inlet ports are not shown in the drawings of the plenum chamber shown in FIGS. 16-28, those skilled in the art will appreciate that in practice one or more inlet ports will be provided, for example inlet ports 6600 as shown in FIGS. 30 and 31. The inlet ports 6600 allow connection of the interface to an air circuit 4170, as described further herein. In some forms of the technology one or more components of the air circuit 4170 may also act as components of a positioning and stabilising structure.

In certain forms of the present technology, the plenum chamber 6200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 6200 is constructed from a translucent material, e.g. translucent silicone. The use of a translucent material can reduce the obtrusiveness of the patient interface, and help improve compliance with therapy.

5.4.3 Support Portions

As best seen in FIGS. 21 and 23-27, in one form of the technology support portions 6260 are provided on opposite sides of the interface 6000 between the second seal forming structure 6102 and an anterior wall of the plenum chamber 6200. As shown in FIG. 21, in an example each support portion 6260 extends to a lateral edge of the interface 6000.

The support portions 6260 are configured to resist or hinder compression in the anterior-posterior direction, and thereby support or stiffen a portion of the second seal forming structure 6102 which engages the patient's lip superior, in particular the portions in an area 1010 proximate the entrances to the nares where the ala meets the area above the lip superior, as shown in FIG. 29.

The support portions 6260 assist in ensuring that creases do not form in the seal forming structure 6100, particularly where the seal forming structure seals against the area 1010 of the patient's face. The support portions 6260 may be particularly advantageous when the seal forming structure is configured to create a corner or ridge 6120 as described herein.

As seen in FIGS. 23-25 in particular, in one form of the technology the support portions 6260 are connected to the anterior side of the oral portion 6201 of the plenum chamber adjacent the boundary 6241 of the oral portion 6201 and the nasal portion 6202. In some embodiments the support portion 6260 may be curved when viewed in cross-section parallel to a sagittal plane (as shown in FIGS. 25-27) and/or when viewed in cross-section parallel to a frontal plane (as shown in FIGS. 23 and 24). The curvature may be positive or negative. In some examples, a lateral side wall portion 6245 of the plenum chamber 6200 may curve inwardly adjacent the boundary 6241 with the nasal portion 6202, and the support portion 6260 may be substantially contiguous with an adjacent lateral side wall portion 6245. As shown in FIG. 27, when viewed in cross-section parallel to a sagittal plane, at least a portion of the support portion 6260 may reduce in thickness between a first end 6261 adjacent the anterior wall of the plenum chamber 6200 and a second end 6262 adjacent the seal forming structure 6100.

As seen in particular in FIGS. 23 and 24, in one form of the technology the support portion 6260 is connected to the oral portion 6201 of the plenum chamber adjacent a boundary of a lateral side wall portion 6245 of the oral portion 6201 and a lateral side wall portion 6246 of the nasal portion 6202.

In some forms of the technology, the support portions 6260 are shaped to provide a substantially clear flow path from the oral portion 6201 of the plenum chamber to the nasal aperture(s) 6135 during inspiration. In some forms of the technology no part of either support portion 6260 is directly inferior to the nasal aperture(s) 6135.

5.4.4 Other Components

The patient interface of FIGS. 16 to 31 may comprise other components as described above with respect to FIGS. 7 to 15 e.g. at least a connection port 3600, forehead support 3700, anti-asphyxia valve, a vent, a decoupling structure, ports, or a positioning and stabilising structure.

While no vent structures are shown in FIGS. 16 to 27, embodiments of the technology shown in FIGS. 16 to 25 may be provided with a suitable vent structure, for example in the plenum chamber 6200 (one example of which is shown in FIG. 30).

5.5 RPT Device

An RPT device 4000 in accordance with one aspect of the present technology comprises mechanical, pneumatic, and/or electrical components and is configured to execute one or more algorithms, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10$cmH_2O$, or at least 20 cmH2O·RPT device algorithms The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors and flow rate sensors.

As mentioned above, in some forms of the present technology, the central controller may be configured to implement one or more algorithms expressed as computer programs stored in a non-transitory computer readable storage medium, such as memory. The algorithms are generally grouped into groups referred to as modules.

The RPT device 4000 may have an electrical power supply 4210, one or more input devices 4220, a central controller, a therapy device controller, a pressure generator 4140, one or more protection circuits, memory, transducers 4270, data communication interface and one or more output devices 4290. Electrical components 4200 may be mounted on a single Printed Circuit Board Assembly (PCBA) 4202. In an alternative form, the RPT device 4000 may include more than one PCBA 4202.

An RPT device in accordance with one form of the present technology may include an air filter 4110, or a plurality of air filters 4110.

In one form, an outlet air filter 4114, for example an antibacterial filter, is located between an outlet of the pneumatic block 4020 and a patient interface 3000.

An RPT device in accordance with one form of the present technology may include a muffler 4120, or a plurality of mufflers 4120.

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.6 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.6.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.7 Humidifier

5.7.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

As shown in FIG. 5C, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

5.7.2 Humidifier Components

5.7.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.7.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.7.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.7.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.7.2.5 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller and/or the humidifier controller 5250. In some forms, a humidifier transducer may be located externally to the humidifier 5000 (such as in the air circuit 4170) while communicating the output signal to the controller.

5.8 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time cccTi 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.9 Respiratory Pressure Therapy Modes

Various respiratory pressure therapy modes may be implemented by the RPT device 4000 depending on the values of the parameters A and Po in the treatment pressure equation used by the therapy parameter determination algorithm in one form of the present technology.

5.10 Glossary

For the purposes of the present technology disclosure, in certain forms of the present technology, one or more of the following definitions may apply. In other forms of the present technology, alternative definitions may apply.

5.10.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. ‘Flow rate’ is sometimes shortened to simply ‘flow’ or ‘airflow’.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient’s face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.10.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.10.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

- 'Soft' materials may include silicone or thermo-plastic elastomer (TPE), and may, e.g. readily deform under finger pressure.
- 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.10.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.10.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

5.10.4 Anatomy

5.10.4.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bonyframework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

*Glabella*: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labialfold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittalplane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.10.4.2 Anatomy of the Skull Frontal bone: The frontal bone includes a large vertical portion, the squama *frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.10.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.10.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.10.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.10.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the pointp they must walk downhill). See FIG. 3E (relatively small negative curvature compared to FIG. 3F) and FIG. 3F (relatively large negative curvature compared to FIG. 3E). Such curves are often referred to as convex.

5.10.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.10.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 30).

Osculating plane: The plane containing the unit tangent vector and the unit principal normal vector. See FIGS. 30 and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 30), a space curve turning towards the direction of the left-hand binormal may be considered as having a left-hand positive torsion (e.g. a left-hand helix). Hence left-hand positive is equivalent to right-hand negative. See FIG. 3T.

5.10.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.11 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms “a”, “an”, and “the” include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms “comprises” and “comprising” should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms “first” and “second” may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.12 REFERENCE SIGNS LIST

| | |
|---|---|
| Patient | 1000 |
| bed partner | 1100 |
| patient interface | 3000 |
| seal - forming structure | 3100 |
| superior - facing medial portion | 3111 |
| medial saddle portion | 3112 |
| anterior - facing medial portion | 3115 |
| lip superior portion | 3116 |
| oral hole peripheral portion | 3117 |
| lip inferior portion | 3118 |
| superior - facing intermediate portion | 3121 |
| anterior facing intermediate portion | 3125 |
| posterior - facing lateral portion | 3135 |
| lateral portions | 3145 |
| lateral support portion | 3151 |
| plenum chamber | 3200 |
| Chord | 3209 |
| fascia portion | 3210 |
| lateral headgear support recess | 3212 |
| lateral insert | 3214 |
| interior rim | 3215 |
| exterior rim | 3216 |
| locating features | 3217 |
| insert openings | 3218 |
| medial portion | 3219 |
| superior point | 3220 |
| inferior point | 3229 |
| nasal portion | 3230 |
| lateral portions | 3231 |
| Base | 3232 |
| inlet port | 3240 |
| hollow protrusion | 3250 |
| Rim | 3252 |
| superior portion | 3254 |
| inferior portion | 3256 |
| oral portion | 3260 |
| oral hole | 3271 |
| nasal holes | 3272 |
| oronasal transition | 3275 |
| positioning and stabilising structure | 3300 |
| headgear connection support | 3302 |
| upper strap | 3310 |
| upper strap connection point | 3315 |
| lower strap | 3320 |
| lower connection point | 3325 |
| lower strap clip | 3326 |
| top crown strap | 3330 |
| lateral crown strap | 3332 |
| neck strap | 3334 |
| headgear tube | 3340 |
| Tab | 3342 |
| headgear tube connector | 3344 |
| headgear connector | 3246 |
| conduit headgear inlet | 3390 |
| Vent | 3400 |
| connection port | 3600 |
| first end | 3602 |
| second end | 3604 |
| annular groove | 3606 |
| Ridge | 3608 |
| conduit connection portion | 3610 |
| forehead support | 3700 |
| RPT device | 4000 |
| external housing | 4010 |

-continued

| 5.12 REFERENCE SIGNS LIST | |
|---|---|
| upper portion | 4012 |
| lower portion | 4014 |
| Panel | 4015 |
| Chassis | 4016 |
| Handle | 4018 |
| pneumatic block | 4020 |
| air filter | 4110 |
| inlet air filter | 4112 |
| outlet air filter | 4114 |
| Muffler | 4120 |
| inlet muffler | 4122 |
| outlet muffler | 4124 |
| pressure generator | 4140 |
| Blower | 4142 |
| Motor | 4144 |
| anti - spill back valve | 4160 |
| air circuit | 4170 |
| heated air circuit | 4171 |
| supplemental oxygen | 4180 |
| electrical components | 4200 |
| Printed Circuit Board Assembly (PCBA) | 4202 |
| electrical power supply | 4210 |
| input devices | 4220 |
| Transducers | 4270 |
| output devices | 4290 |
| Humidifier | 5000 |
| humidifier inlet | 5002 |
| humidifier outlet | 5004 |
| humidifier base | 5006 |
| Reservoir | 5110 |
| conductive portion | 5120 |
| humidifier reservoir dock | 5130 |
| locking lever | 5135 |
| water level indicator | 5150 |
| humidifier transducer | 5210 |
| air pressure sensor | 5212 |
| air flow rate transducer | 5214 |
| temperature sensor | 5216 |
| heating element | 5240 |
| humidifier controller | 5250 |
| central humidifier controller | 5251 |
| heating element controller | 5252 |
| air circuit controller | 5254 |

The invention claimed is:

1. A patient interface comprising:

a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient;

a first seal-forming structure connected to an oral portion of the plenum chamber, the first seal-forming structure constructed and arranged to form a seal with a region of the patient's face surrounding an entrance to the patient's mouth such that the flow of air at said therapeutic pressure is delivered to the mouth, the first seal-forming structure constructed and arranged to maintain said therapeutic pressure in the plenum chamber throughout the patient's respiratory cycle in use;

a second seal-forming structure connected to a nasal portion of the plenum chamber, the second seal-forming structure constructed and arranged to form a seal with a region of the patient's face surrounding an entrance to the patient's nose such that the flow of air at said therapeutic pressure is delivered to the nose, the second seal-forming structure constructed and arranged to maintain said therapeutic pressure in the plenum chamber throughout the patient's respiratory cycle in use; and a vent structure to allow a continuous flow of gases exhaled by the patient from an interior of the plenum chamber to vent to ambient, said vent structure being sized and shaped to maintain the therapeutic pressure in the plenum chamber in use, wherein the second seal-forming structure comprises a pair of lateral portions respectively disposed at lateral sides of the second seal-forming structure, wherein posterior surfaces of the lateral portions of the second seal forming structure slope in a superior-anterior direction from a boundary of the first and second seal forming structures, wherein a boundary between the first seal-forming structure and the second seal-forming structure comprises a ridge, and wherein the ridge forms a convex shape along patient-contacting surfaces of the patient interface.

2. The patient interface of claim 1, wherein the slope of each lateral portion forms an angle of between 20 degrees and 90 degrees with a mid-contact plane of the mask.

3. The patient interface of claim 1, wherein no part of the patient interface is configured to contact the patient's alar crest point, in use.

4. The patient interface of claim 1, wherein at least a portion of the oral portion of the plenum chamber comprises a flexible shell.

5. The patient interface of claim 4, wherein the flexible shell is formed from a material having a Young's modulus of less than 0.4 GPa.

6. The patient interface of claim 4, wherein the material of the flexible shell is the same as a material that forms the first seal-forming structure and the second seal-forming structure.

7. The patient interface of claim 4, wherein a rigidizing member is connected to the shell.

8. The patient interface of claim 1, wherein the plenum chamber is at least partially formed by a shell and the vent structure is provided to the shell.

9. The patient interface of claim 1, wherein the ridge is configured to engage the patient's face at least proximate an entrance to the patient's nares, in use.

10. The patient interface of claim 1, wherein the ridge extends across an entire boundary between the first seal-forming structure and the second seal-forming structure.

11. The patient interface of claim 1, wherein, in use, the ridge is configured to engage the patient's face proximate the entrances to the patient's nares where each of the patient's ala meets the face above the patient's lip superior.

12. The patient interface of claim 1, wherein the ridge forms a corner, the first seal-forming structure extending directly from the corner on a first side thereof and the second seal-forming structure extending directly from the corner on a second side thereof.

13. The patient interface of claim 12, wherein, during use, the corner is configured to resist the formation of creases in portions of the first seal-forming structure and/or the second seal forming structure adjacent the corner.

14. The patient interface of claim 1, wherein, in use, the second seal-forming structure extends directly from the ridge in a superior-anterior direction.

15. The patient interface of claim 1, wherein the ridge forms an angle between the first seal-forming structure and the second seal-forming structure.

16. The patient interface of claim 15, wherein the angle formed by the first seal-forming structure and second seal-forming structure is in the range of 20 degrees to 90 degrees.

17. The patient interface of claim 1, wherein, in use, the ridge is configured to allow patient-contacting portions of the second seal-forming structure to pivot or hinge about an area at or adjacent the ridge.

18. The patient interface of claim 1, wherein the ridge extends only across a posterior patient-contacting side of the patient interface and is not present on an anterior non-patient-contacting side of the patient interface.

19. The patient interface of claim 1, wherein the second seal-forming structure includes a pair of nasal apertures configured to, in use, deliver the flow of air to the patient's nose.

20. A patient interface comprising:

a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient;

a first seal-forming structure connected to an oral portion of the plenum chamber, the first seal-forming structure constructed and arranged to form a seal with a region of the patient's face surrounding an entrance to the patient's mouth such that the flow of air at said therapeutic pressure is delivered to the mouth, the first seal-forming structure constructed and arranged to maintain said therapeutic pressure in the plenum chamber throughout the patient's respiratory cycle in use;

a second seal-forming structure connected to a nasal portion of the plenum chamber, the second seal-forming structure constructed and arranged to form a seal with a region of the patient's face surrounding an entrance to the patient's nose such that the flow of air at said therapeutic pressure is delivered to the nose, the second seal-forming structure constructed and arranged to maintain said therapeutic pressure in the plenum chamber throughout the patient's respiratory cycle in use; and a vent structure to allow a continuous flow of gases exhaled by the patient from an interior of the plenum chamber to vent to ambient, said vent structure being sized and shaped to maintain the therapeutic pressure in the plenum chamber in use, wherein the second seal-forming structure comprises a pair of lateral portions respectively disposed at lateral sides of the second seal-forming structure, wherein posterior surfaces of the lateral portions of the second seal forming structure slope in a superior-anterior direction from a boundary of the first and second seal forming structures, wherein a boundary between the first seal-forming structure and the second seal-forming structure comprises a ridge, and wherein the ridge forms a corner, the first seal-forming structure extending directly from the corner on a first side thereof and the second seal-forming structure extending directly from the corner on a second side thereof.

21. A patient interface comprising:

a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient;

a first seal-forming structure connected to an oral portion of the plenum chamber, the first seal-forming structure constructed and arranged to form a seal with a region of the patient's face surrounding an entrance to the patient's mouth such that the flow of air at said therapeutic pressure is delivered to the mouth, the first seal-forming structure constructed and arranged to maintain said therapeutic pressure in the plenum chamber throughout the patient's respiratory cycle in use;

a second seal-forming structure connected to a nasal portion of the plenum chamber, the second seal-forming structure constructed and arranged to form a seal with a region of the patient's face surrounding an entrance to the patient's nose such that the flow of air at said therapeutic pressure is delivered to the nose, the second seal-forming structure constructed and arranged to maintain said therapeutic pressure in the plenum chamber throughout the patient's respiratory cycle in use; and a vent structure to allow a continuous flow of gases exhaled by the patient from an interior of the plenum chamber to vent to ambient, said vent structure being sized and shaped to maintain the therapeutic pressure in the plenum chamber in use, wherein the second seal-forming structure comprises a pair of lateral portions respectively disposed at lateral sides of the second seal-forming structure, wherein posterior surfaces of the lateral portions of the second seal forming structure slope in a superior-anterior direction from a boundary of the first and second seal forming structures, wherein a boundary between the first seal-forming structure and the second seal-forming structure comprises a ridge, and wherein the ridge extends only across a posterior patient-contacting side of the patient interface and is not present on an anterior non-patient-contacting side of the patient interface.

* * * * *